US008244478B2

(12) United States Patent
Takahashi et al.

(10) Patent No.: US 8,244,478 B2
(45) Date of Patent: Aug. 14, 2012

(54) METHOD OF CLASSIFYING GENE EXPRESSION STRENGTH IN LUNG CANCER TISSUES

(75) Inventors: Takashi Takahashi, Nagoya (JP); Shuta Tomita, Nagoya (JP); Tetsuya Mitsudomi, Nagoya (JP); Yasushi Yatabe, Nagoya (JP); Nobuhiko Ogura, Ashigarakami-gun (JP); Masato Some, Ashigarakami-gun (JP)

(73) Assignees: Aichi Prefecture, Nagoya (JP); FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/942,770

(22) Filed: Nov. 9, 2010

(65) Prior Publication Data

US 2011/0081652 A1 Apr. 7, 2011

Related U.S. Application Data

(62) Division of application No. 11/008,265, filed on Dec. 10, 2004, now Pat. No. 7,856,318.

(30) Foreign Application Priority Data

Dec. 12, 2003 (JP) ................................ 2003-415119

(51) Int. Cl.
*G06F 7/00* (2006.01)

(52) U.S. Cl. .............. 702/19; 702/20; 703/11; 707/700; 536/24.5; 435/6.1

(58) Field of Classification Search ........................ None
See application file for complete search history.

(56) References Cited

U.S. PATENT DOCUMENTS

| | | | | |
|---|---|---|---|---|
| 6,812,339 | B1 | 11/2004 | Venter et al. | |
| 7,856,318 | B2 * | 12/2010 | Takahashi et al. | 702/19 |
| 2003/0104499 | A1 | 6/2003 | Pressman et al. | |
| 2003/0219760 | A1 | 11/2003 | Gordon et al. | |
| 2009/0104617 | A1 | 4/2009 | Gordon et al. | |

FOREIGN PATENT DOCUMENTS

| | | | |
|---|---|---|---|
| WO | 02/44331 | A2 | 6/2002 |
| WO | 03/029273 | A2 | 4/2003 |
| WO | 2004/005891 | A2 | 1/2004 |
| WO | 2006/053442 | A1 | 5/2006 |

OTHER PUBLICATIONS

Robert Ginsberg et al. "section 2: non-small cell lung cancer", Cancer of the Lung, Chapter 30.2 pp. 858-911; 2004.*

European Search Report issued Mar. 2, 2005, in EP Application No. 04029389.6.

Ganbunshi Hyouteki Chiryou, 2003, 1(1): 72-77.

T.R. Golub et al., "Molecular Classification of Cancer: Class Discovery and Class Prediction by Gene Expression Monitoring", Science, 1999, 286: 531-537.

Helen Han et al., "Prognostic Value of Immunohistochemical Expressions of p53, HER-2/*neu*, and bcl-2 in Stage I Non-Small-Cell Lung Cancer", Human Pathology, 2002, 33(1):105-110.

Yoshitsugu Horio et al., "Prognostic Significance of p53 Mutations and 3p Deletions in Primary Resected Non-Small Cell Lung Cancer", Cancer Research, 1993, 53: 1-4.

Japanese Office Action issued May 19, 2009, in JP Application No. 2003-415119.

Judit Moldvay et al., "P53 Expression in Stage I Squamous Cell Lung Cancer", Pathology Oncology Research, 1998, 4(1): 8-13.

Partial European Search Report issued May 14, 2007, in EP Application No. 07006700.4.

Manfred Volm et al., "Prognostic Value of Vascular Endothelial Growth Factor and its Receptor Flt-1 in Squamous Cell Lung Cancer", Int. J. Cancer (Pred. Oncol.), 1997, 74: 64-68.

Dennis A. Wigle et al., "Molecular Profiling of Non-Small Cell Lung Cancer and Correlation with Disease-free Survival", Cancer Research, 2002, 62: 3005-3008.

T. Yoshida et al., "The clinical significance of Cyclin B1 and Wee1 expression in non-small-cell lung cancer", Annals of Oncology, 2004, 15: 252-256.

Extended European Search Report issued in EP Application No. 10182585.9, dated Jan. 21, 2011 (in the name of Aichi Prefecture, et al.).

* cited by examiner

*Primary Examiner* — Mary Zeman
(74) *Attorney, Agent, or Firm* — Sughrue Mion, PLLC

(57) ABSTRACT

The present invention provides a method of confirming the gene expression, useful in the decision of a five year survival rate of a patient with lung cancer and the use of a DNA probe kit in the method. A method useful in the decision of a survival rate of a patient with non-small cell lung cancer comprising confirming the expression strength of at least one gene in lung cancer tissues isolated from the patient.

1 Claim, 6 Drawing Sheets

METHOD OF CLASSIFYING GENE EXPRESSION STRENGTH IN LUNG CANCER TISSUES

CROSS-REFERENCE TO RELATED APPLICATIONS

This is a divisional of U.S. patent application Ser. No. 11/008,265, filed Dec. 10, 2004 (presently allowed). The entire disclosure of the prior application is considered part of the disclosure and is hereby incorporated by reference.

TECHNICAL FIELD

The present invention relates to a method of confirming the expression of a specific gene in lung cancer tissues, used in a technique of predicting a five year survival rate of a patient with lung cancer with high accuracy.

BACKGROUND OF THE INVENTION

When various therapies are applied to patients with cancer (carcinoma), a five year survival rate is often used as a measure of cure. That is, a five year survival rate is a probability that a patient who underwent a cancer diagnosis or therapy will be survival over five years thereafter. By this probability, a progressive level (stage) of cancer, a therapeutic effect and the like are represented.

Until now, the TNM classification comprising the combination of the size of tumor (tumor meter, represented by T), the range where metastasis to lymphonodi are observed (represented by N) and the presence or absence of distant metastasis (represented by M), each of which is determined by clinical method, has been mainly used ("Cancer of the lung," written by Robert Ginsberg et al., 5th edition, pp. 858 to 910, Lippincott-Raven (1997)). For example, patients judged to be in stage I under the TNM classification means those having a progressive level such that a little over 60% of the patients could be survival for five years if cancer is resected by surgery. Patients judged to be in stage III means those having a progressive level such that at most 20% the patients could be survival even under the same condition.

Recently, focusing on one or two genes specifically expressed in cancer patients or cancer tissues, a therapeutic effect is often predicted by determining the difference in the expression of said gene(s) between patients showing superior therapeutic effect and patients showing poor therapeutic effect (Horio et al, Cancer Research, Vol. 54, pp. 1 to 4, Jan. 1, 1993).

SUMMARY OF THE INVENTION

However, the TNM classification cannot be applied unless outcomes of many clinical tests are accumulated. Thus, this classification is not be said to be simple and its accuracy is not satisfactory at all. And, in a method of predicting a therapeutic effect by confirming the expression of a specific gene, the correlation between the gene expression in patients with lung cancer and a five year survival rate of the patients has not been reported.

An object of the present invention is to accurately decide a survival rate of patients especially with lung cancer. In the present invention, the expression of a specific gene in lung Cancer tissues is confirmed.

Accordingly, the present invention relates to a method useful in the decision of a survival rate of a patient with non-small cell lung cancer comprising confirming the expression strength of at least one gene selected from the group consisting of WEE1 (AA039640), MYC (AA464600), TITF1 (T60168), FOSL1 (T82817), LYPLA1 (H00817), SSBP1 (R05693), SFTPC (AA487571), THBD (H59861), NICE-4 (AA054954), PTN (AA001449), SNRPB (AA599116), NAP1L1 (R93829) CTNND1 (AA024656), CCT3 (R60933), DSC2 (AA074677), SPRR1B (AA447835), COPB (AA598868), ARG1 (AA453673), ARCN1 (AA598401), MST1 (T47813), SERPINE1 (N75719), SERPINB1 (AA486275), EST fragment (N73201), ACTR3 (N34974), PTP4A3 (AA039851), ISLR (H62387), ANXA1 (H63077), GJA1 (AA487623), HSPE1 (AA448396) and PSMA5 (AA598815) in lung cancer tissues isolated from the patient.

And, the present invention provides a method useful in the decision of a survival rate of a patient with squamous cell lung cancer comprising confirming the expression strength of at least one gene selected from the group consisting of FLJ20619 (R74480), SPC12 (R19183), EST fragment (R96358), KRT5 (AA160507), PTP4A3 (AA039851), SPRR1B (AA947835), LOC339324 (W23522), MYST4 (AA057313), SPARCL1 (AA990694), IGJ (T70057), EIF4A2 (H05919), EST fragment (AA115121), ID2 (H82706), THBD (H59861), MGC15476 (W72525), ZFP (H53499), COPB (AA598868), ZYG (AA453289) CACNA1I (N52765), FLJ4623 (N71473), CSTB (H22919), EPB41L1 (R71689), MGC4549 (AA455267), EST fragment (T64878), DSC2 (AA074677), EST fragment (H79007), EST fragment (W84776), IFI30 (AA630800), EST fragment (T81155) and IL1RN(T72877) in lung cancer tissues isolated from the patient.

Further, the present invention provides a method useful in the decision of the survival rate of a patient with non-squamous cell lung cancer comprising confirming the expression strength of at least one gene selected from the group Consisting of NICE-4 (AA054954), WEE1 (AA039640) SSBP1 (R05693), WFDC2 (AA451904), ACTA2 (AA634006), G22P1 (AA486311), MST1 (T47813), PHB (R60946), DRPLA (H08642), SNRBP (AA599116), GJA1 (AA487623), SFTPC (AA487571), ACTR1A(R40850), MYC (AA464600), RAD23B (A2489678), CCT3(R60933), SERPINE1 (N75719), LAMP1 (H29077), IRAK1 (AA683550), BIRC2 (R19628), LMAN1 (H73420), HSPE1 (AA448396), TMSB4X (AA634103), EEF1G (R43973), EST fragment (H05820), LYPLA1 (H00817), SOD1 (R52548), ARG1 (AA453673), KRT25A (W73634) and FOSL1 (T82817) in lung cancer tissues isolated from the patient.

Another aspect of the present invention relates to the use in the above method of a DNA probe comprising a nucleic acid sequence specifically hybridizing to at least one gene targeted in this method.

All genes which expression is to be confirmed in the present invention are known genes. The nucleotide sequence of each gene is registered in "UniGene", one of the public databases provided by NCBI, with its abbreviated name and its accession number represented by the combination of alphabet (such as AA) and numeral. In the present specification including claims, all of the genes to be confirmed in the method of the present invention are represented with the abbreviated names and the accession numbers registered in "UniGene" on Nov. 19, 2003. Since a gene can be specified with the abbreviated name and the accession number registered in "UniGene", those skilled in the art easily confirm a gene in question and its detailed nucleotide sequence by referring to "UniGene" and conduct the present invention. Similarly, as to a nucleic acid sequence of a DNA prove specific for each gene used in the method of the present invention, those skilled in the art can easily determine some candidate sequences for each gene based on the nucleic acid sequence registered in the above database using a homology searching program or the like. Especially, the nucleic acid sequence of the probe of the present invention is not limited unless it is selected such that the probe can be specifically hybridized to a gene corresponding therefor. It is not necessarily to restrict or limit to one nucleic acid sequence. Such a procedure can be made by those skilled in the art without having a need of any specific effort.

The present inventors studied to search for genes specifically expressed in lung cancer tissues of patients who were underwent non-small cell lung cancer diagnosis or therapy and who were dead within five years thereafter or survival over five or more years thereafter. As the result, they found that there is a specific tendency between a five year survival rate and a gene expression pattern.

Focusing on genes whose expression amounts were specifically increased or decreased in cancer tissues of the group of patients who were dead within five years after operation or diagnosis as compared with the group of patients who were survival over five years after operation or diagnosis, the present inventors selected predictive genes capable of distinguishing both groups efficiently using a signal-to-noise metrics (Golub et al., Science, Vol. 286, pp. 531 to 537 (1999)). Briefly, if a prognosis favorable patient and a prognosis fatal patient are defined to belong to class 0 and class 1 respectively, a signal-to-noise statistic (Sx) for gene x is calculated as follows:

$$Sx=(\mu\text{class }0-\mu\text{class }1/\delta\text{class }0+\delta\text{class }1)$$

As to each gene, μclass 0 means an average of data on total expression strength of patients belonging to class 0 (a group of prognosis favorable patients) and δclass 0 means a standard deviation of data on total expression strength of patients belonging to class 0 (a group of prognosis favorable patients). Using the thus-calculated absolute value of Sx, genes ranked higher, i.e. genes showing a significant difference in expression strength between the group of prognosis favorable patients and the group of prognosis fatal patients, were selected.

In order to assay a statistical significance of a marker gene specific for a different type of cancer, a temple level (prognosis favorable or fatal) of each patient used in the analysis in association with a set of data on gene expression strength were randomly labeled and then the signal-to-noise value (Sx value) was recalculated in accordance with the labels after randomizing. This procedure was repeated 10,000 times. P values were assigned to every genes based on the extent so that Sx value obtained by randomizing the labels was better than Sx value obtained actually.

When genes to be judged that they are significantly related to a survival rate of patients with a different type of lung cancer, i.e. predictive genes, were searched for among genes expressed in cancer tissues of the patients, the following correlation became clear.

Thus, an expression pattern such that in many lung cancer tissues of patients who were underwent non-small cell lung cancer diagnosis or therapy and dead within five years thereafter, the expression of each of WEE1 (AA039640), MYC (AA464600), FOSL1 (T82817), LYPLA1 (H00817), SSBP1 (R05693), THEM (H59861), NICE-4 (AA054954), PTN (AA001449), SNRPB (AA599116), NAP1L1 (R93829), CTNND1 (AA024656), CCT3 (R60933), DSC2 (AA074677), SPRR1B (AA447835), COPB (AA598868), ARG1 (AA453673), ARCN1 (AA598401), MST1 (T47813), SERPINE1 (N75719), SERPINB1 (AA486275), ACTR3 (N34974), PTP4A3 (AA039851), ISLR (H62387), ANXA1 (1163077), GJA1 (AA487623), HSPE1 (AA448396) and PSMA5 (AA598815) was significantly increased and the expression of each of TITF1 (T60168), SFTPC (AA487571) and EST fragment (N73201) was significantly lowered was observed. Hereinafter, the group comprising the above genes is referred to be a gene group 1.

Accordingly, by extracting total RNAs from cancer tissues of a patient who was underwent a non-small cell lung cancer diagnosis and confirming the expression strength of at least one gene belonging to the gene group 1, it is possible to predict a five year survival rate of the patient whether the patient would be dead within five years or survival over five or more years.

For example, when PTP4A3 (AA039851, fatal) is selected as a gene and a five year survival rate is predicted based on the outcome obtained by confirming the expression strength of this gene, an accuracy of 64% can be expected. When WEE1 (AA039640, fatal) or ACTR3 (N34974, fatal) is selected as a gene in addition to PTP4A3 (AA039851, fatal) and a five year survival rate is predicted based on the outcomes obtained by confirming the expression strength of these genes, an accuracy will be 66% or 7.4%. And, based on the outcomes obtained by confirming the expression strength of all genes constituting the gene group 1, an accuracy will reach 82%. The above outcomes have reliability higher than that of the prior method.

Although non-small cell lung cancer is further classified squamous cell cancer (SQ) and non-squamous cell cancer (non-SQ), the gene group 1 is useful as a gene group selected when a five year survival rate is decided without subdividing the type of lung cancer cells.

On the other-hand, the present inventors confirmed the gene expression strength for squamous cell cancer (SQ) and non-squamous cell cancer (non-SQ) and as the result, they found that a five year survival rate can be decided more accurately by using a gene group different from the gene group 1 as targets.

Thus, an expression pattern such that in many lung cancer tissues of patients who were underwent squamous cell cancer diagnosis of therapy and dead within five years thereafter, the expression of each of KRT5 (AA160507), PTP4A3 (AA039851), SPRR1B (AA447835), MYST4 (AA057313), SPARCL1 (AA490694), IGJ (T70057), EST fragment (M115121), 102 (H82706), THBD (H59861), MGC15476 (W72525), COPB (AA598868), ZYG (AA453289), CACNA1I (N52765), CSTB (1122919), EPB41L1 (R71689), MGC4549 (AA455267), DSC2 (AA074677), IFI30 (AA630800), EST fragment (T81155) and IL1RN (T72877) was significantly increased and the expression of each of FLJ20619 (R74480), SPC12 (R19183), EST fragment (R96358), LOC339324 (W23522), EIF4A2 (H05919), ZFP (H53499), FLJ4623 (N71473), EST fragment (T64878), EST fragment (H79007) and EST fragment (W84776) was significantly lowered was observed. Hereinafter, the group comprising the above genes is referred to be a gene group 2.

Accordingly, by extracting total RNAs from cancer tissues of a patient who was underwent a squamous cell cancer diagnosis and confirming the expression strength of at least one gene belonging to the gene group 2, it is possible to predict a five year survival rate of the patient whether the patient would be dead within five years or survival over five or more years.

For example, when CACNAII (N52765, fatal) is selected as a gene and a five year survival rate is predicted based on the outcome obtained by confirming the expression strength of this gene, an accuracy of 81% can be expected. When FLJ20619 (R74480, favorable) is selected as a gene in addition to CACNAII (N52765, fatal) and a five year survival rate is predicted based on the outcomes obtained by confirming the expression strength of these genes, an accuracy will be 75% or 81%. And, based on the outcomes obtained by confirming the expression strength of all genes constituting the gene group 2, an accuracy will reach 100%.

And, an expression pattern such that in many lung cancer tissues of patients who were underwent non-squamous cell cancer diagnosis or therapy and dead within five years thereafter, the expression of each of NICE-4 (AA054954), WEE1 (AA039640), SSBP1 (R05693), G22P1 (AA486311), MST1 (T47813) PHB (R60946), DRPLA (H08642), SNRBP (AA599116), GJA1 (AA487623), ACTR1A (R40850), MYC (AA464600), RAD23B (AA489678), CCT3 (R60933), SERPINE1 (N75719), BIRC2 (R19628), LMAN1 (H73420) HSPE1 (AA448396), EEF1G (R43973), EST fragment (1405820), LYPLA1 (H00817), SOD1 (R52548), ARG1 (AA453673), KRT25A (W73634) and FOSL1 (T82817) was significantly increased and the expression of each of WFDC2 (AA451904), ACTA2 (AA634006), SFTPC (AA487571), LAMP1 (H29077), IRAK1 (AA683550) and TMSB4X (AA634103) was significantly lowered was observed. Hereinafter, the group comprising the above genes is referred to be a gene group 3.

Accordingly, by extracting total RNAs from cancer tissues of a patient who was underwent a non-squamous cell cancer and confirming the expression strength of at least one gene belonging to the gene group 3, it is possible to predict a five year survival rate of the patient whether the patient would be dead within five years or survival over five or more years.

For example, when SFTPC (AA487571, favorable) is selected as a gene and a five year survival rate is predicted based on the outcome obtained by confirming the expression strength of this gene, an accuracy of 56% can be expected. When NICE-4 (AA054954, fatal) or GJA1 (AA487623, fatal) is selected as a gene in addition to SFTPC (AA487571, favorable) and a five year survival rate is predicted based on the outcomes obtained by the expression strength of these genes, an accuracy will be 79% or 76%. And, based on the outcomes obtained by the expression strength of all genes constituting the gene group 3, an accuracy will reach 91%.

As mentioned above, it is preferable to select two or more genes, more preferably all genes belonging to each gene group as targets although only one gene may be freely selected from each gene group and used it.

Further, the present invention provides information about samples γobtained from cancer tissues of new patients for deciding whether the patients will be survival or dead based on the above correlation.

In order to decide whether new patients with lung cancer (test samples γ) will be prognostic favorable or fatal after five years, Vx may be calculated for each gene contained in a set of predictive genes from the equation: $Vx=Sx(Gx^{\gamma}-bx)$ wherein Sx is the above-mentioned signal-to-noise statistic; $Gx^{\gamma}$ represents the expression strength of each gene x contained in the set of predictive genes; and bx is calculated from the equation: $bx=(\mu class\ 0+\mu class\ 1)/2$. When the sum of Vx ($\Sigma Vx$) for the genes contained in the set of predictive genes is calculated to be plus (+), the patient in question is decided to be “prognosis favorable”. When $\Sigma Vx$ is calculated to be minus (−), the patient in question is decided to be “prognosis fatal”.

EFFECT OF THE INVENTION

Figure 1:
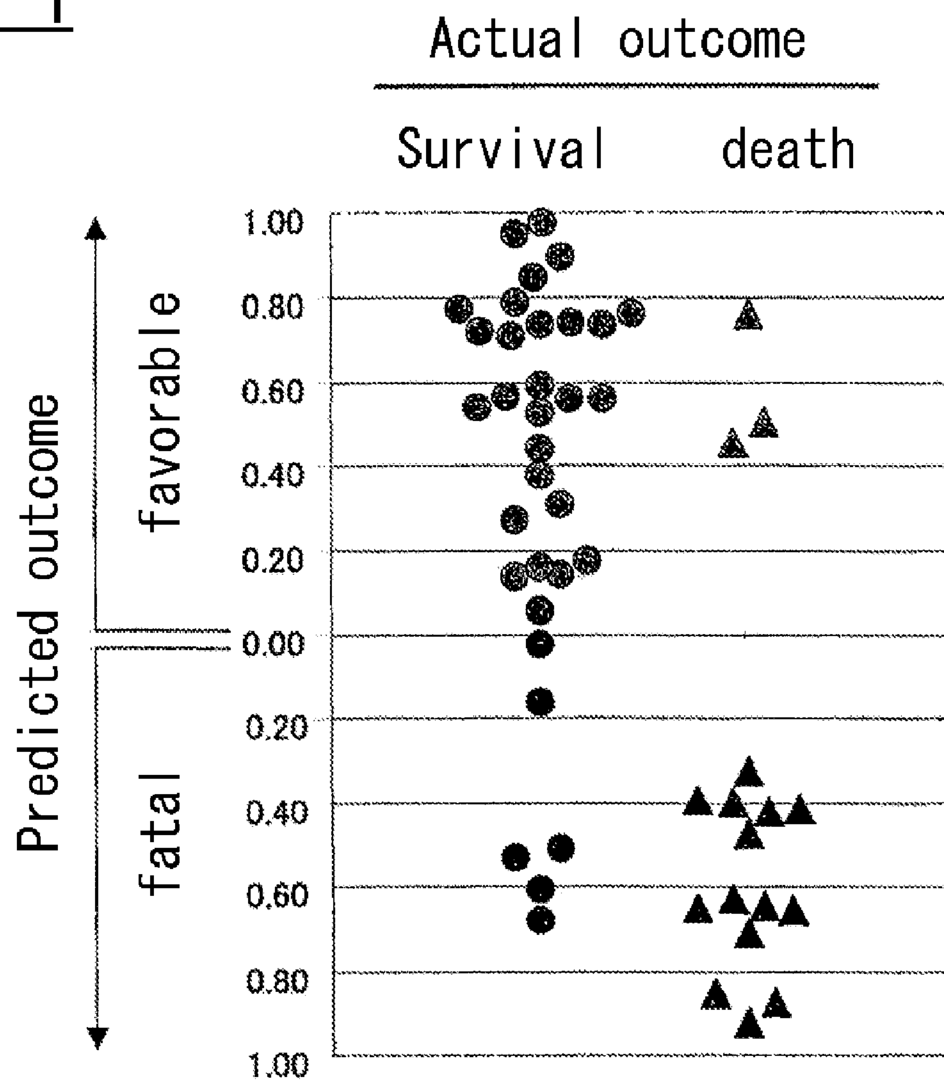
FIG. 1 represents the outcomes obtained by predicting patients with non-squamous cell lung cancer using 25 predictive genes in a weighted-voting model.

By using the method of the present invention, a five year survival rate of patients with lung cancer can be predicted with high accuracy. Therefore, it is possible according to the present invention to predict whether or not a patient with a different type of lung cancer could be survival over five or more years with high accuracy by Confirming that a specified gene group is expressed in cancer tissues of the patient.

DISCLOSURE OF THE INVENTION

Expression strength of each gene belonging to the gene group specified in the present invention can be confirmed by providing a specific probe every nucleotide sequence and conducting PCR or hybridization. The nucleotide sequence of each gene can be easily confirmed from the database “UniGene”. And, conditions such as the design of a probe specifically hybridizing to each gene, its synthesis, hybridization and the like can be suitably determined by those skilled in the art without having a need of any specific effort.

The probe can be synthesized as a set of probes capable of subjecting to PCR reaction for each gene, i.e. PCR primers. The expression strength may be confirmed by conducting PCR reaction using these primers.

Upon practice of the present method, the expression of a gene is preferably confirmed in the so-called microarray. As an microarray, a glass substrate on which probe DNAs are spotted; a membrane on which probe DNAs are spotted; beads on which probe DNAs are spotted; a glass substrate on which probes are directly synthesized; and the like have been developed. Examples of the microarray include a membrane microarray available from Invitrogen (GeneFilters™, Mammalian Microarrays; Catalog #GF200 or GF201). This membrane microarray contains 11168 spots in total of probe DNA corresponding to 8644 independent genes. It is confirmed by Blast search that the sequence of each probe does not occur the so-called cross hybridization even when gene (s) closely related to each sequence is (are) present, otherwise the expression of such gene (s) is detected erroneously.

Examples of the microarray available in the present invention include cDNA or oligo-arrays available from Affimetrix, Agilent and other companies, in addition to the membrane microarray available from Invitrogen.

It is desirable in the present invention to immediately frozen cancer tissues isolated from a patient with lung cancer during thoractomy or by biopsy with an endoscope or the like to prepare a slice, prepare a tissue section by hollowing out minutely regions rich in cancer cells in the slice, extract RNAs from the tissue section according to any standard method and transform all mRNAs expressed in the tissue into a cDNA by acting a reverse transcriptase thereto. In this case, the targeted gene group can be labeled by adding to the cDNA a suitable radioisotope such as $^{33}P$ and the like or a fluorochrome such as Cy3, Cy5 and the like during the preparation of the cDNA via the reaction with a reverse transcriptase.

According to the present invention, based on the information about the nucleotide sequence of the gene contained in each gene group, the expression strength of the gene to be detected can be confirmed by hybridization or real time PCR using an oligoDNA specific for each gene to be detected. Preferably the expression of each gene group to be detected is confirmed more easily by combining cDNAs prepared with a reverse transcriptase and a suitable label with a microarray.

The expression strength of a gene group targeted in the present invention can be confirmed easily by hybridizing a labeled cDNA and a microarray under suitable conditions and then confirming the expression of the genes and their amounts as an index of the label. The expression strength is confirmed by quantifying the strength of a signal produced from the label by a suitable method.

For example, when a radioactive label is used, a signal strength can be quantified by exposing a hybridized array to an imaging plate (Fuji Photo Film), scanning and imaging using a bioimaging analyzer BAS 5000 (Fuji Photo Film), processing images of the hybridized array using L Process (Fuji Photo Film) and then analyzing using an analytical soft Array Gauge (Fuji Photo Film). Alternatively, the strength of a radioactive label can be quantified using a phospho-imager (Amersham). And, the strength of a fluorescent label can be quantified using a microarray reader (Agilent) or the like.

The thus-obtained data on label strength are converted to data on hybridization strength, respectively by using, for example, the method of Tseng et al. (Nucleic Acids Res., Vol., 29, pp. 2549 to 2557). Thereafter, a reproducibility in expression is evaluated after normalization, preparation of scatter plots for each gene and the like. Thus, a significant increase or decrease in expression amount of a targeted gene may be evaluated.

EXAMPLES

The present invention will be described in more detail by referring to the following examples which are not to be construed as limiting the scope of the invention.

Example 1

In the following example, all procedures using commercially available kits were conducted under conditions as recommended by the manufactures unless otherwise stated.

1) Extraction of Total RNAs from Lung Cancer Tissue

From each of 50 patients (15 females and 35 males; between the ages of 43 and 76, average age of 63) with non-small cell lung cancer, specifically 30 patients with glandular lung cancer, 16 patients with squamous cell lung cancer and 4 patients with large cell lung cancer (23 patients with stage I, 11 patients with stage II and 16 patients with stage III), lung cancer tissues (0.5 g in average) were isolated. The tissues were embedded in OCT compound and frozen at −80° C., thereby a frozen sample of 7 μm in thickness was prepared. Then, a region rich in cancer cells was carefully excised from the sample to obtain a section having cancer cells accounted for 75.4% in average of cells contained therein. From this section, total RNAs (12 μg in average) were extracted using RNAeasy (Quiagen) and a purity thereof was confirmed using RNA 600 nanoassay kit and 2100 Bioanalyzer (Agilent).

2) Hybridization to Microarray 5 micrograms of the total RNAs as prepared in the above 1) was transformed into cDNA using oligo-dT primer (Invitrogen) and Superscript II reverse transcriptase (Invitrogen) by adding 10 μCi of [$^{32}P$] dCTP. GeneFilters (Invitrogen) was prehybridized in 10 ml of AlkPhos DIRECT hybridization buffer (Amersham) containing 0.5 μg/ml of poly-dA (Invitrogen) and 0.5 μg/ml of Cot-1 DNA (Invitrogen) at 51° C. for 2 hours and then hybridized with a modified radiolabeled probe cDNA for 17 hours.

After hybridizing, the microarray was washed with a solution containing 2M urea, 0.1% SDS, 50 mM sodium phosphate buffer solution (pH 7.0), 150 mM NaCl, 1 mM $MgCl_2$ and 0.2% AlkPhos DIRECT blocking reagent (Amersham) twice, a solution containing 2 mM $MgCl_2$, 50 mM Tris and 100 mM NaCl twice ands solution containing 2 mM $MgCl_2$, 50 mM Tris and 15 mM NaCl twice successively. The microarray was exposed to an imaging plate (Fuji Photo Film) for 2 hours and then the imaging plate was scanned and imaged using a bioimaging analyzer BAS 5000 (Fuji Photo Film) with resolution of 25 μm. The image of the hybridized array was processed with L Process (Fuji Photo Film) and then a signal strength was quantified using an analytical soft Array Gauge (Fuji Photo Film).

3) Data Processing

The data on signal strength obtained in the above 2) was converted to data on hybridization strength, respectively. First, the method of Tseng et al. (Nucleic Acids Res., Vol. 29, pp. 2549 to 2557) was employed for selecting genes used in the fitting of a non-linear nomralization curve. After normalization, scatter plots of 50 sets of replication data on each gene were prepared and a reproducibility of expression between replication pairs was evaluated. Genes showing a Pearson correlation coefficient of 0.85 or higher were selected. An average of the first hybridization and the second hybridization was used for further analysis. In addition, genes not showing a double or half change at least an expression level were excluded. Genes having a median intensity of less than 0.3 were excluded from the following analysis.

4) Isolation of Gene for Five Year Survival

Predictive genes distinguishing patients who would be dead within five years after operation or diagnosis (prognosis fatal patients) and patients who would be survival over five years after operation or diagnosis (prognosis favorable patients) most efficiently were selected using a signal-to noise metrics (Golub et al., Science, Vol. 286, pp. 531 to 537 (1999)). Briefly, if a prognosis favorable patient and a prognosis fatal patient are defined to belong to class 0 and class 1 respectively, a signal-to-noise statistic (Sx) is calculated as follows:

$$Sx=(\mu\text{class } 0-\mu\text{class } 1/\delta\text{class } 0+\delta\text{class } 1)$$

As to each gene, μclass 0 means an average of data on total expression strength of patients belonging to class 0 (the group of prognosis favorable patients) and δclass 0 means a standard deviation of data on total expression strength of patients belonging to class 0 (the group of prognosis favorable patients).

Genes ranked higher based on the absolute value of Sx were selected. In order to predict the outcomes using the thus-selected genes, a weighted-voting Classification algorithm was employed. The thus-obtained outcome classifiers were tested using a leave-one-out cross validation. In this scheme, the algorithm can be employed to find decision boundaries between class average and bx=(μclass 0+μclass 1)/2 for each gene, in addition to the calculation of Sx.

5) Permutation Test

In order to assay a statistical significance of a marker gene specific for a different type of cancer, a sample level (survival or dead) of each patient used in the analysis together with a set of data on gene expression strength were labeled randomly and then the signal-to-noise value (Sx value) for each gene was recalculated in accordance with the labels after randomizing. This procedure was repeated 10,000 times. P values were assigned to every genes based on the extent so that Sx value obtained by randomizing the labels was better than Sx value obtained actually.

Since our final goal was to develop outcome classifiers at patient level, a supervised learning method was employed. Thus, weighted-voting outcome classifiers were constructed based on the predictive genes preselected using the signal-to-noise metrics. A learning error against each model while increasing the number of predictive genes used was calculated by a leave-one-out cross validation. Among 30 genes constituting the outcome classifiers for non-small cell cancer (Table 1), the weighted-voting model using 25 predictive genes ranked top 25 revealed the highest accuracy such that 41 patients (82%) of 50 patients revealed the outcomes as predicted individually (FIG. 1).

TABLE 1

| Non-small cell cancer | | | | | | | | |
|---|---|---|---|---|---|---|---|---|
| Rank | Gene | Description | accession No. | expression in lung cancer | P | bx | Sx | SEQ ID NO. |
| 1 | WEE1 | WEE1 homolog | AA039640 | Up | 0.0027 | 0.483 | 0.483 | SEQ ID NO: 1 |
| 2 | MYC | v-myc viral oncogene homolog | AA464600 | Up | 0.0057 | 0.479 | 0.441 | SEQ ID NO: 2 |
| 3 | TITF1 | thyroid transcription factor 1 | T60168 | Down | 0.0085 | 0.452 | 0.416 | SEQ ID NO: 3 |
| 4 | FOSL1 | FOS-like antigen 1 (Fra-1) | T82817 | Up | 0.0062 | 0.330 | 0.411 | SEQ ID NO: 4 |
| 5 | LYPLA1 | lysophospholipase I | H00817 | Up | 0.0081 | 0.460 | 0.408 | SEQ ID NO: 5 |
| 6 | SSBP1 | single-stranded DNA binding protein | R05693 | Up | 0.0199 | 0.495 | 0.406 | SEQ ID NO: 6 |
| 7 | SFTPC | surfactant, pulmonary-associated protein C | AA487571 | Down | 0.0113 | 0.322 | 0.405 | SEQ ID NO: 7 |
| 8 | THBD | thrombomodulin | H59861 | Up | 0.0099 | 0.466 | 0.403 | SEQ ID NO: 8 |
| 9 | NICE-4 | NICE-4 protein | AA054954 | Up | 0.0099 | 0.514 | 0.403 | SEQ ID NO: 9 |
| 10 | PTN | pleiotrophin (heparin binding growth factor 8) | AA001449 | Up | 0.0100 | 0.500 | 0.401 | SEQ ID NO: 10 |
| 11 | SNRPB | small nuclear ribonucleoprotein polypeptides B and B1 | AA599116 | Up | 0.0115 | 0.657 | 0.394 | SEQ ID NO: 11 |
| 13 | CTNND1 | catenin delta 1 | R93829 | Up | 0.0120 | 0.513 | 0.393 | SEQ ID NO: 12 |
| 12 | NAP1L1 | nucleosome assembly protein 1-like 1 | AA024656 | Up | 0.0131 | 0.483 | 0.384 | SEQ ID NO: 13 |
| 14 | CCT3 | chaperonin containing TCP1, subunit 3 | R60933 | Up | 0.0186 | 0.566 | 0.378 | SEQ ID NO: 14 |
| 15 | DSC2 | desmocollin 2 | AA074677 | Up | 0.0160 | 0.533 | 0.374 | SEQ ID NO: 15 |
| 16 | SPRR1B | small proline-rich protein 1B (cornifin) | AA447835 | Up | 0.0209 | 0.421 | 0.370 | SEQ ID NO: 16 |
| 17 | COPB | coatomer protein complex, subunit beta | AA598868 | Up | 0.0195 | 0.466 | 0.369 | SEQ ID NO: 17 |
| 18 | ARG1 | arginase type I (liver) | AA453673 | Up | 0.0193 | 0.581 | 0.369 | SEQ ID NO: 18 |
| 19 | ARCN1 | archain 1 (coatomer protein complex, subunit delta) | AA598401 | Up | 0.0169 | 0.412 | 0.367 | SEQ ID NO: 19 |
| 20 | MST1 | macrophage stimulating 1 | T47813 | Up | 0.0193 | 0.462 | 0.366 | SEQ ID NO: 20 |
| 21 | SERPINE1 | serine (or cysteine) proteinase inhibitor, clade E member 1 | N75719 | Up | 0.0194 | 0.495 | 0.366 | SEQ ID NO: 21 |
| 22 | SERPINB1 | serine (or cysteine) proteinase inhibitor, clade B member 1 | AA486275 | Up | 0.0205 | 0.556 | 0.362 | SEQ ID NO: 22 |
| 23 | ESTs | | N73201 | Down | 0.0205 | 0.494 | 0.360 | SEQ ID NO: 23 |
| 24 | ACTR3 | actin-related protein 3 homolog (ARP3) | N34974 | Up | 0.0229 | 0.496 | 0.358 | SEQ ID NO: 24 |
| 25 | PTP4A3 | protein tyrosine phosphatase type 4A, member 3 | AA039851 | Up | 0.0199 | 0.478 | 0.357 | SEQ ID NO: 25 |
| 26 | ISLR | immunoglobulin superfamily containing leucine-rich repeat | H62387 | Up | 0.0228 | 0.478 | 0.356 | SEQ ID NO: 26 |
| 27 | ANXA1 | annexin A1 | H63077 | Up | 0.0262 | 0.367 | 0.354 | SEQ ID NO: 27 |
| 28 | GJA1 | gap junction protein, alpha 1 | AA487623 | Up | 0.0230 | 0.406 | 0.354 | SEQ ID NO: 28 |
| 29 | HSPE1 | heat shock 10 kD protein 1 | AA448396 | Up | 0.0273 | 0.444 | 0.352 | SEQ ID NO: 29 |
| 30 | PSMA5 | proteasome (prosome, macropain) subunit, alpha type, 5 | AA598815 | Up | 0.0265 | 0.545 | 0.346 | SEQ ID NO: 30 |

6) Construction of Model Predicting Survival Rate of Patients with Non-Small Cell Cancer In order to develop an outcome prediction classifier of each patient, a signal-to-noise metrics was employed for selecting a gene distinguishing prognosis favorable patients from prognosis fatal patients most clearly. As the outcomes of a non-supervised hierarchical clustering algorithm using spots ranked top 100 corresponding to unique 98 genes, two major branches representing prognosis favorable patients and prognosis fatal patients were obtained. Among 21 patients with non-small cell cancer, 19 patients (left frame), i.e. the favorable branch, were survival over five years after operation. On the other hand, among 29 patients with non-small cell cancer, 15 patients (right frame),i.e. the fatal branch, were dead within five years after operation. The Kaplan-Meier survival curve reveals statistically significant difference.

Figure 2:
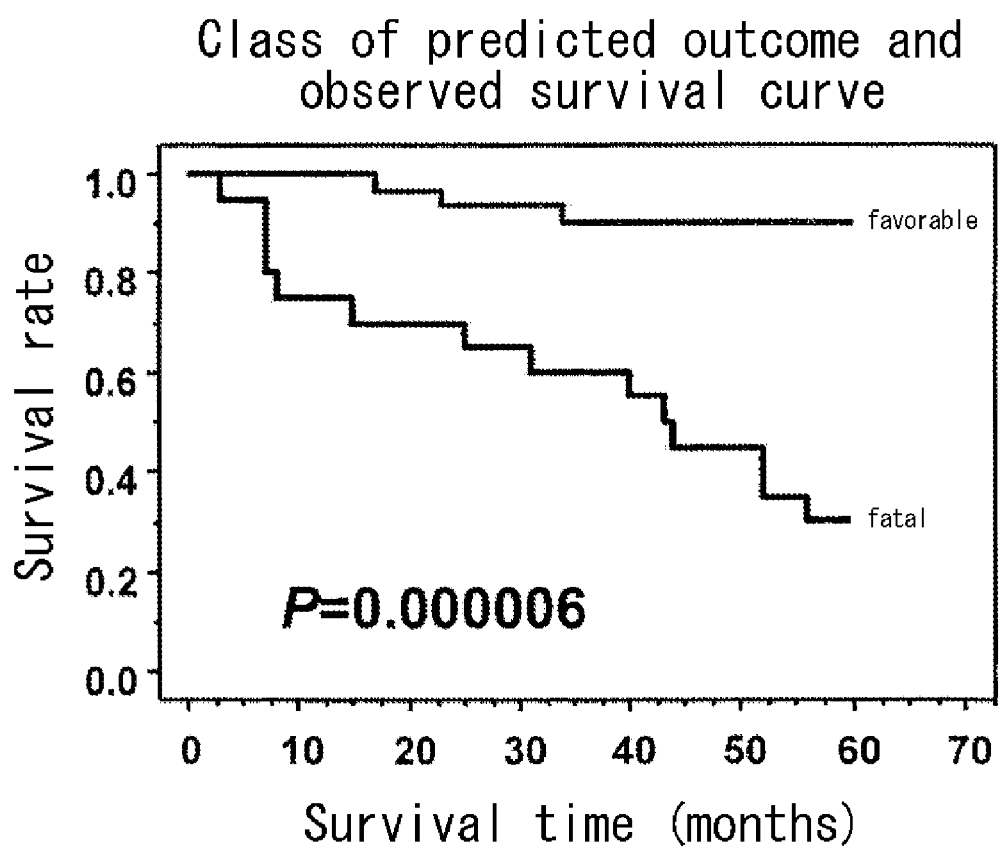
FIG. 2 is a survival curve showing the prognosis “favorable” or “fatal” of patients with non-small cell lung cancer.

As to these classifiers, 27 patients of 33 patients (82%) practically survival over five or more years after operation were decided to be "prognosis favorable" and 14 patients of 17 patients (82%) practically dead within five years after operation were decided to be "prognosis fatal". A survival curve of patients for the prediction of "prognosis favorable" or "prognosis fatal" is shown in FIG. 2. This figure reveals the difference between two groups ($P=6.0\times10^{-6}$).

With the increase in the number of the above genes, another supervised learning algorithm including Support vector machine and k-nearest neighbors was employed. The accuracy of the model is comparable with that of the weighted-voting outcome classifiers, but the latter showed the highest accuracy.

In order to decide whether new patients with lung cancer (test samples γ) could be prognosis favorable or fatal after five years, Vx may be calculated for each gene contained in the set of predictive genes from the equation: $Vx=Sx\ (Gx^{Y}-bx)$ wherein Sx is the above-mentioned signal-to-noise statistic; $GX^{Y}$ represents an expression strength of each gene x contained in the set of predictive genes; and bx is calculated from $bx=(\mu class\ 0+\mu class\ 1)/2$. When the sum of VX ($\Sigma Vx$) for genes contained in the set of predictive genes is calculated to be plus (+), the patient in question is decided to be "prognosis favorable". When $\Sigma Vx$ is calculated to be minus (−), the patient in question is decided to be "prognosis fatal".

With the increase in the number of the above genes, another supervised learning algorithm including Support vector machine and k-nearest neighbors was employed. The accuracy of the model is comparable with that of the weighted-voting outcome classifiers, but the latter showed the highest accuracy.

7) Construction of Model Predicting Survival Rate Specific for Each of Squamous Cell Cancer and Non-Squamous Cell Cancer Squamous cell cancer and non-squamous cell cancer are recognized as diseases distinguishable clinicopathologically each other. Thus, using predictive genes for each subtype selected with the weighted-voting algorithm and the signal-to-noise metrics, outcome prediction classifiers for a different type of cancer were constructed.

Among 30 genes constituting the outcome classifiers for a different type of cancer (Tables 2 and 3), 12 genes (Table 2) for non-squamous cell cancer and 19 genes (Table 3) for squamous cell cancer revealed the highest accuracy by a leave-one-out cross validation including the increase in the number of predictive genes ranked higher.

TABLE 2

| Non-squamous cell cancer | | | | | | | | |
|---|---|---|---|---|---|---|---|---|
| Rank | Gene | Description | accession No. | expression in lung cancer | P | bx | Sx | SEQ ID NO. |
| 1 | NICE-4 | NICE-4 protein | AA054954 | Up | 0.0036 | 0.567 | 0.604 | SEQ ID NO: 9 |
| 2 | WEE1 | WEE1 homolog | AA039640 | Up | 0.0039 | 0.485 | 0.567 | SEQ ID NO: 1 |
| 3 | SSBP1 | single-stranded DNA binding protein | R05693 | Up | 0.0122 | 0.466 | 0.500 | SEQ ID NO: 6 |
| 4 | WFDC2 | WAP four-disulfide core domain 2 | AA451904 | Down | 0.0155 | 0.544 | 0.489 | SEQ ID NO: 56 |
| 5 | ACTA2 | actin, alpha 2, smooth muscle, aorta | AA634006 | Down | 0.0149 | 0.684 | 0.487 | SEQ ID NO: 57 |
| 6 | G22P1 | thyroid autoantigen 70 kDa (Ku70) | AA486311 | Up | 0.0176 | 0.519 | 0.482 | SEQ ID NO: 58 |
| 7 | MST1 | macrophage stimulating 1 | T47813 | Up | 0.0153 | 0.462 | 0.481 | SEQ ID NO: 20 |
| 8 | PHB | prohibitin | R60946 | Up | 0.0219 | 0.419 | 0.472 | SEQ ID NO: 59 |
| 9 | DRPLA | dentatorubral-pallidoluysian atrophy | H08642 | Up | 0.0238 | 0.478 | 0.455 | SEQ ID NO: 60 |
| 10 | SNRPB | small nuclear ribonucleoprotein polypeptides B and B1 | AA599116 | Up | 0.0192 | 0.615 | 0.455 | SEQ ID NO: 11 |
| 11 | GJA1 | gap junction protein, alpha 1 | AA487623 | Up | 0.0268 | 0.332 | 0.446 | SEQ ID NO: 61 |
| 12 | SFTPC | surfactant, pulmonary-associated protein C | AA487571 | Down | 0.0313 | 0.350 | 0.445 | SEQ ID NO: 7 |
| 13 | ACTR1A | actin-related protein 1 homolog A | R40850 | Up | 0.0256 | 0.626 | 0.444 | SEQ ID NO: 62 |
| 14 | MYC | v-myc viral oncogene homolog | AA464600 | Up | 0.0294 | 0.385 | 0.434 | SEQ ID NO: 2 |
| 15 | RAD23B | RAD23 homolog B | AA489678 | Up | 0.0276 | 0.495 | 0.434 | SEQ ID NO: 63 |
| 16 | CCT3 | chaperonin containing TCP1, subunit 3 | R60933 | Up | 0.0305 | 0.548 | 0.431 | SEQ ID NO: 14 |
| 17 | SERPINE1 | serine (or cysteine) proteinase inhibitor, clade E member 1 | N75719 | Up | 0.0338 | 0.473 | 0.424 | SEQ ID NO: 21 |
| 18 | LAMP1 | lysosomal-associated membrane protein 1 | H29077 | Down | 0.0374 | 0.382 | 0.418 | SEQ ID NO: 64 |
| 19 | IRAK1 | interleukin-1 receptor-associated kinase 1 | AA683550 | Down | 0.0355 | 0.199 | 0.414 | SEQ ID NO: 65 |
| 20 | BIRC2 | baculoviral IAP repeat-containing 2 | R19628 | Up | 0.0362 | 0.359 | 0.411 | SEQ ID NO: 66 |
| 21 | LMAN1 | lectin, mannose-binding, 1 | H73420 | Up | 0.0339 | 0.409 | 0.411 | SEQ ID NO: 67 |
| 22 | HSPE1 | heat shock 10 kD protein 1 | AA448396 | Up | 0.0411 | 0.406 | 0.410 | SEQ ID NO: 68 |
| 23 | TMSB4X | thymosin, beta 4, X chromosome | AA634103 | Down | 0.0440 | 0.585 | 0.404 | SEQ ID NO: 69 |
| 24 | EEF1G | eukaryotic translation elongation factor 1 gamma | R43973 | Up | 0.0450 | 0.638 | 0.404 | SEQ ID NO: 70 |
| 25 | ESTs | | H05820 | Up | 0.0492 | 0.570 | 0.403 | SEQ ID NO: 71 |
| 26 | LYPLA1 | lysophospholipase I | H00817 | Up | 0.0488 | 0.456 | 0.401 | SEQ ID NO: 5 |
| 27 | SOD1 | superoxide dismutase 1 | R52548 | Up | 0.0477 | 0.609 | 0.397 | SEQ ID NO: 72 |
| 28 | ARG1 | arginase type I (liver) | AA453673 | Up | 0.0454 | 0.541 | 0.396 | SEQ ID NO: 18 |
| 29 | KRT25A | type I inner root sheath specific keratin 25 irs1 | W73634 | Up | 0.0534 | 0.584 | 0.394 | SEQ ID NO: 75 |
| 30 | FOSL1 | FOS-like antigen 1 (Fra-1) | T82817 | Up | 0.0366 | 0.309 | 0.391 | SEQ ID NO: 4 |

TABLE 3

| Squamous cell cancer | | | | | | | | |
|---|---|---|---|---|---|---|---|---|
| Rank | Gene | Description | accession No. | expression in lung cancer | P | bx | Sx | SEQ ID NO. |
| 1 | FLJ20619 | hypothetical protein | R74480 | Down | 0.0068 | 0.507 | 0.882 | SEQ ID NO: 31 |
| 2 | SPC12 | signal peptidase 12 kDa | R19183 | Down | 0.0087 | 0.521 | 0.859 | SEQ ID NO: 32 |
| 3 | ESTs | | R96358 | Down | 0.0034 | 0.448 | 0.835 | SEQ ID NO: 33 |
| 4 | KRT5 | keratin 5 | AA160507 | Up | 0.0046 | 0.841 | 0.789 | SEQ ID NO: 34 |
| 5 | PTP4A3 | protein tyrosine phosphatase type 4A, member 3 | AA039851 | Up | 0.0104 | 0.438 | 0.753 | SEQ ID NO: 25 |
| 6 | SPRR1B | small proline-rich protein 1B | AA447835 | Up | 0.0147 | 0.695 | 0.730 | SEQ ID NO: 16 |
| 7 | LOC339324 | hypothetical protein LOC339324 | W23522 | Down | 0.0171 | 0.536 | 0.693 | SEO ID NO: 35 |
| 8 | MYST4 | MYST histone acetyltransferase 4 | AA057313 | Up | 0.0188 | 0.573 | 0.691 | SEQ ID NO: 36 |
| 9 | SPARCL1 | SPARC-like 1 | AA490694 | Up | 0.0210 | 0.454 | 0.682 | SEQ ID NO: 37 |
| 10 | IGJ | immunoglobulin J polypeptide | T70057 | Up | 0.0143 | 0.385 | 0.681 | SEQ ID NO: 38 |
| 11 | EIF4A2 | eukaryotic translation initiation factor 4A, isoform 2 | H05919 | Down | 0.0233 | 0.750 | 0.679 | SEQ ID NO: 39 |

TABLE 3-continued

| Squamous cell cancer | | | | | | | | |
|---|---|---|---|---|---|---|---|---|
| Rank | Gene | Description | accession No. | expression in lung cancer | P | bx | Sx | SEQ ID NO. |
| 12 | ESTs | | AA115121 | Up | 0.0226 | 0.412 | 0.672 | SEQ ID NO: 40 |
| 13 | ID2 | inhibitor of DNA binding 2 | H82706 | Up | 0.0214 | 0.608 | 0.670 | SEQ ID NO: 41 |
| 14 | THBD | thrombomodulin | H59861 | Up | 0.0077 | 0.636 | 0.669 | SEQ ID NO: 8 |
| 15 | MGC15476 | Thymus expressed gene 3-like | W72525 | Up | 0.0231 | 0.412 | 0.665 | SEQ ID NO: 42 |
| 16 | ZFP | zinc finger protein | H53499 | Down | 0.0217 | 0.632 | 0.659 | SEQ ID NO: 43 |
| 17 | COPB | coatomer protein complex, subunit beta | AA598868 | Up | 0.0272 | 0.527 | 0.648 | SEQ ID NO: 17 |
| 18 | ZYG | ZYG homolog | AA453289 | Up | 0.0237 | 0.349 | 0.647 | SEQ ID NO: 44 |
| 19 | CACNA1I | calcium channel, voltage-dependent, alpha 1I subunit | N52765 | Up | 0.0312 | 0.495 | 0.636 | SEQ ID NO: 45 |
| 20 | FLJ4623 | hypothetical protein | N71473 | Down | 0.0309 | 0.457 | 0.632 | SEQ ID NO: 46 |
| 21 | CSTB | cystatin B | H22919 | Up | 0.0286 | 0.762 | 0.631 | SEQ ID NO: 47 |
| 22 | EPB41L1 | erythrocyte membrane protein band 4.1-like 1 | R71689 | Up | 0.0482 | 0.690 | 0.613 | SEQ ID NO: 48 |
| 23 | MGC4549 | hypothetical protein | AA455267 | Up | 0.0327 | 0.410 | 0.606 | SEQ ID NO: 49 |
| 24 | ESTs | | T64878 | Down | 0.0406 | 0.457 | 0.600 | SEQ ID NO: 50 |
| 25 | DSC2 | desmocollin 2 | AA074677 | Up | 0.0407 | 0.656 | 0.592 | SEQ ID NO: 15 |
| 26 | ESTs | | H79007 | Down | 0.0415 | 0.363 | 0.590 | SEQ ID NO: 51 |
| 27 | ESTs | | W84776 | Down | 0.0364 | 0.665 | 0.587 | SEQ ID NO: 52 |
| 28 | IFI30 | interferon, gamma-inducible protein 30 | AA630800 | Up | 0.0415 | 0.336 | 0.587 | SEQ ID NO: 53 |
| 29 | ESTs | | T81155 | Up | 0.0552 | 0.633 | 0.583 | SEQ ID NO: 54 |
| 30 | IL1RN | interleukin 1 receptor antagonist | T72877 | Up | 0.0431 | 0.573 | 0.578 | SEQ ID NO: 55 |

Figure 3:
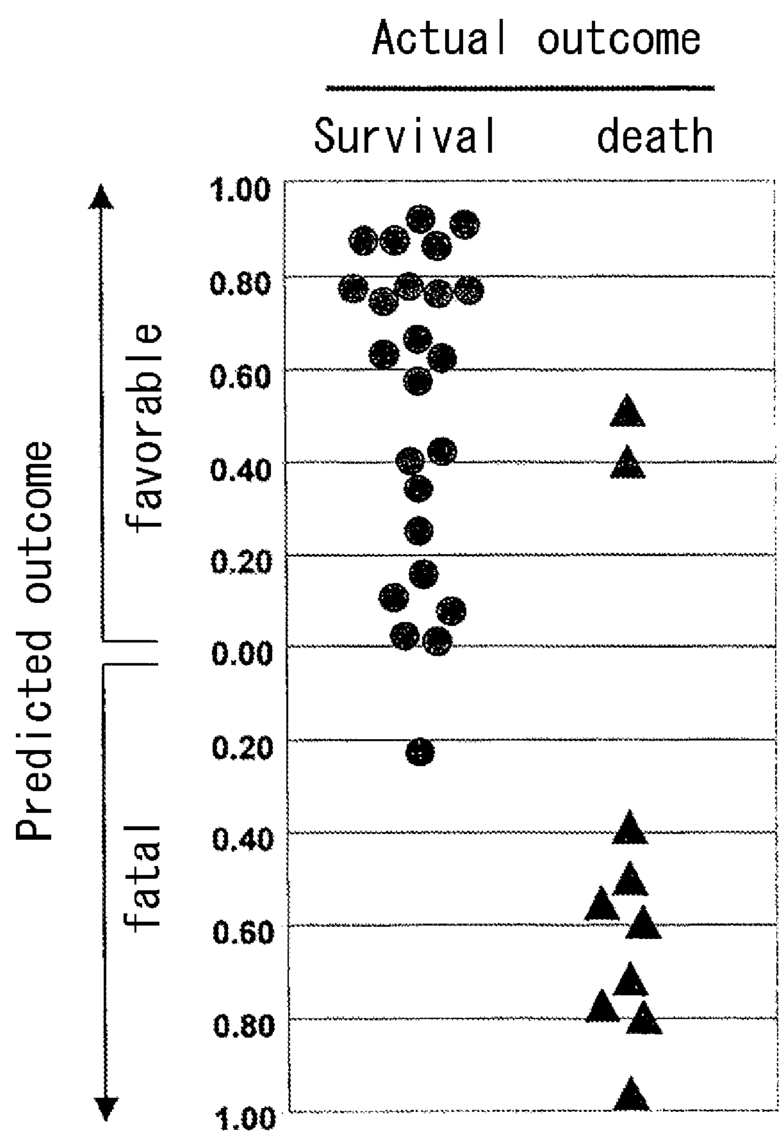
FIG. 3 represents the outcomes obtained by predicting patients with non-squamous cell lung cancer using 12 predictive genes in a weighted-voting model.
Figure 4:
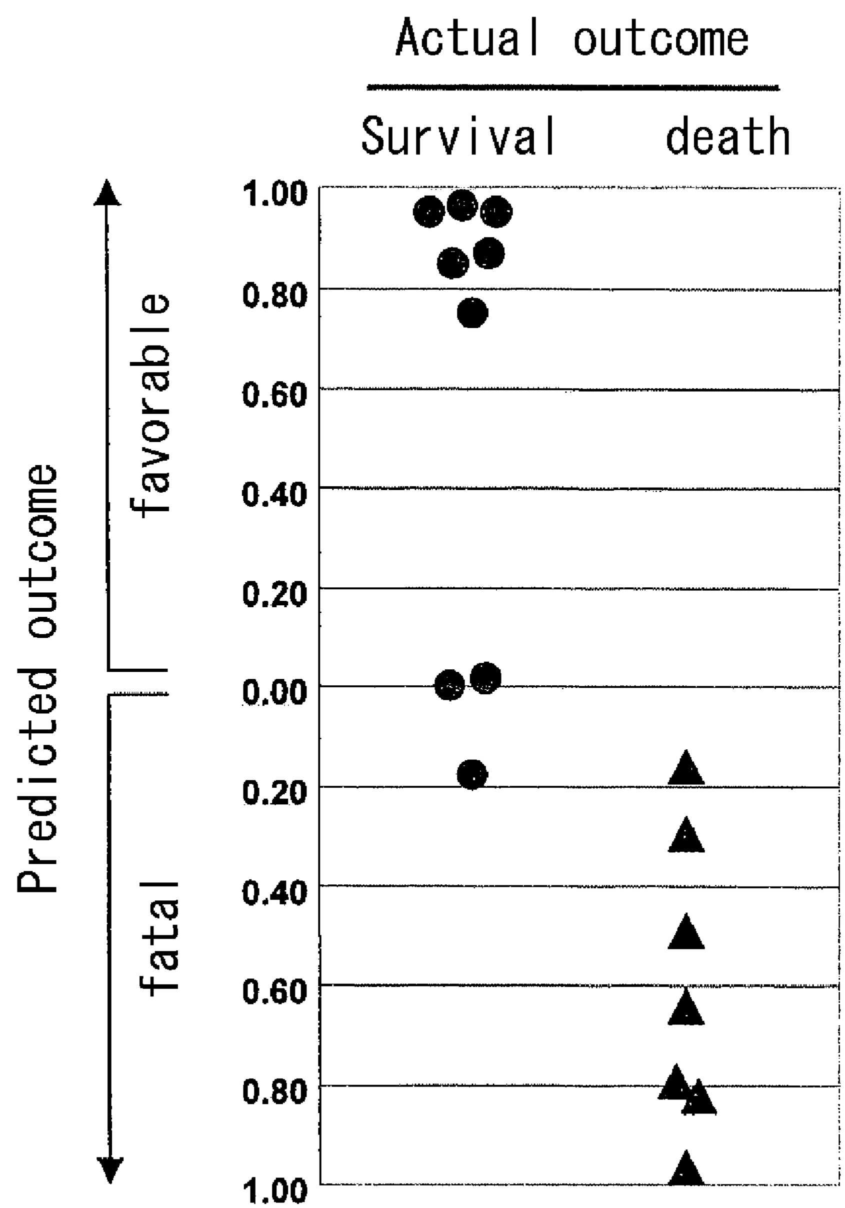
FIG. 4 represents the outcomes obtained by predicting patients with squamous cell lung cancer using 19 predictive genes in a weighted-voting model.
Figure 5:
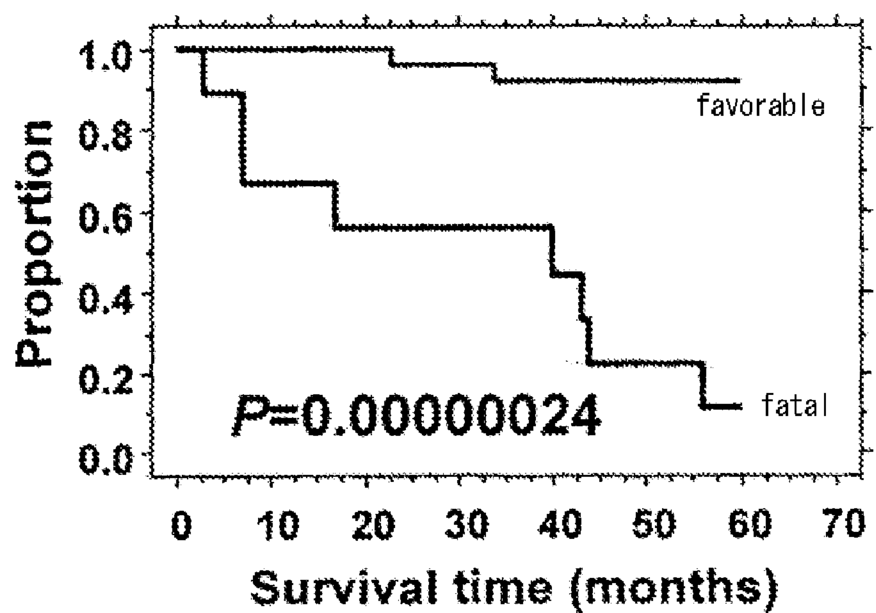
FIG. 5 is a survival curve showing the prognosis “favorable” or “fatal” of patients with non-squamous cell lung cancer.
Figure 6:
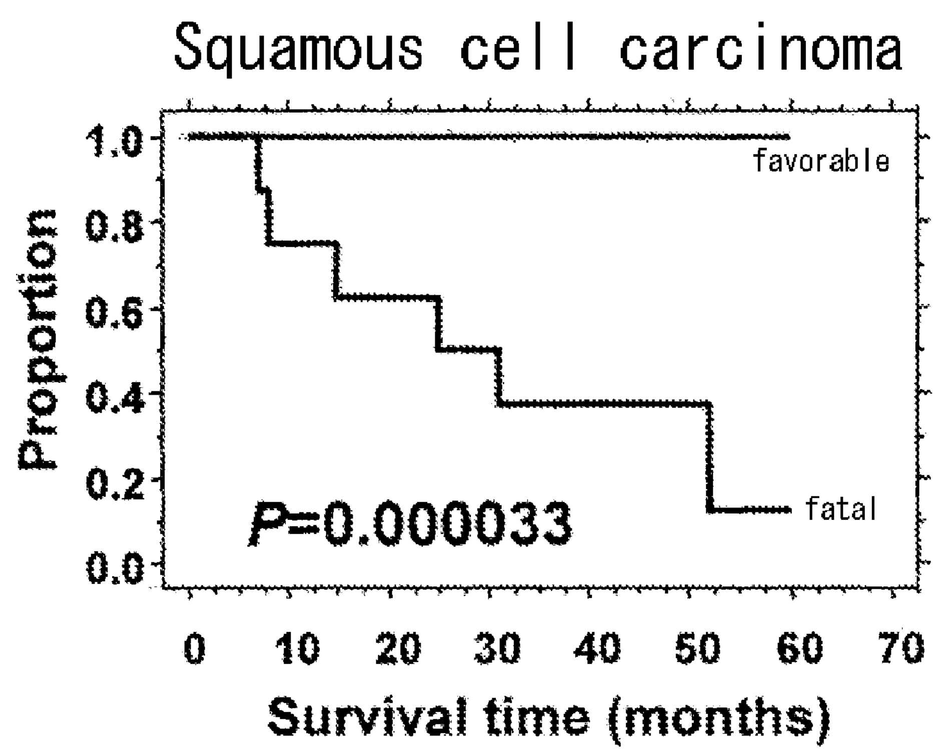
FIG. 6 is a survival curve showing the prognosis “favorable” or “fatal” of patients with squamous cell lung cancer.

These outcomes show that among 34 patients with non-squamous cell cancer, a five year survival rate after operation of 31 patients (91%) was accurately predicted (FIG. 3). Specifically, among 25 patients who were predicted to be "prognosis favorable", 23 patients (92%) were actually survival over five years after operation. Among 9 patients who were decided to be "prognosis fatal", only one patient was survival over five years. The difference between the survival curve of 25 patients who were decided to be "prognosis favorable" and that of 9 patients who were predicted to be "prognosis fatal" was very significant.

What is claimed is:

1. A method for predicting a survival rate of a patient with squamous cell lung cancer, said method comprising the steps of:

(a) isolating a cancer tissue section or a plurality of tissue sections from said patient;

(b) extracting mRNAs from said tissue section or plurality of tissue sections;

(c) transforming said mRNAs from step (b) into cDNAs, wherein said cDNAs are Labeled;

(d) determining the expression strengths of all sequences from Group A, consisting of SEQ ID NO: 34, SEQ ID NO: 25, SEQ ID NO: 16, SEQ ID NO: 36, SEQ ID NO: 37, SEQ ID NO: 38, SEQ ID NO: 40, SEQ ID NO: 41, SEQ ID NO: 8, SEQ ID NO: 42, SEQ ID NO: 17, SEQ ID NO: 44, SEQ ID NO: 45, SEQ ID NO: 47, SEQ ID NO: 48, SEQ ID NO: 49), SEQ ID NO: 15, SEQ ID NO: 53, SEQ ID NO: 54 and SEQ ID NO: 55 and Group B consisting of SEQ ID NO: 31, SEQ ID NO: 32, SEQ ID NO: 33, SEQ ID NO: 35, SEQ ID NO: 39, SEQ ID NO: 43, SEQ ID NO: 46, SEQ ID NO: 50, SEQ ID NO: 51, and SEQ ID NO: 52, and (e) predicting a favorable prognosis when the expression of the sequences of Group A are collectively increased while the expression of the sequences of Group B are collectively decreased, or predicting a fatal prognosis when the expressions of the sequences of Group A are collectively decreased while the expressions of the sequences of Group B are collectively increased.

* * * * *

SEQUENCE LISTING

```
<160> NUMBER OF SEQ ID NOS: 73

<210> SEQ ID NO 1
<211> LENGTH: 4232
<212> TYPE: DNA
<213> ORGANISM: Homo sapiens

<400> SEQUENCE: 1

aaaattgcgt ttgagtttgc cgcgagccgg gccaatcggt tttgccaacg catgcccacg      60

tgctggcgaa caaatgtaaa cacggagatc gtgtgccggg cacttggttt cgtggtgggc     120

aactgtgctg ctgtttcttt tggccgcgga caaggtcggc agaggtggac ccctgcttgg     180

gagagctctt ctcgctgtgc tgacacccgc ccctaacagt cacccacccc ggggaaataa     240

tggggctcgg aggcctcctc ccagccagtg tccagcctaa gcacatcggc tcccgcagtt     300

cagaaaggtc ccgaggcccg agtcaccatt tccggctcag acctcgaccc ggaacgtggc     360

tgcccactgc cacgcccact acgccccagt ggctcgcccc aggggacgag gggcaagaag     420

cggcctccga gggcagcggc cgaaggccat tcggtccctg gctcttccca gctcgcagag     480

acccggaagc gctgcccggc cgcctgcccc tcttcagatc cccagcacc ggaggagcag      540

cgagggggct gcgtccaggc cggctttcgg gtcggcttag gcgaatccag ctctcttttg     600

cccctcccag aaggcccagc cccgtccggg cggtgttcgg gcggcgccgg gccgggcccc     660

ccgccgcccc aggctcgctc ataggcccgg aacaccacag cccgcccaga cttggctggc     720

gccgagccgg gggtggagcc agcgggttcc cgccaaaatc gcgtagctgg tccttccccc     780

gcgggctacg tcgcgccctc cttttttttt caaacccgga gctgcactgg gattggtgga     840

ctgggcactc acgtggttaa cggtcgcggg aagccgcgga gcccgaacct gagactggac     900
```

-continued

```
ctgaggagac ctcagcctcg gtgctcgggc cgccccgcct ctgccggaaa gtccgcgccg    960
ccgctgccgc caccgtccgc agcccgagcg ccccggagcc gcaggccgcc gccgcgcaga   1020
gacgccgcgg ctgcgactag gcgcgcccag ccgcacgtgg cggacccgcc cccaggcccg   1080
cagtgtcctg gaccccgcag gcctccgctc tcctgtcctc ggccccgtcc ccagggccgc   1140
gatgagcttc ctgagccgac agcagccgcc gccaccccgc cgcgccgggg cggcctgcac   1200
cttgcggcag aagctgatct tctcgccctg cagcgactgt gaggaggagg aagaagagga   1260
ggaggaggag ggcagcggcc acagcaccgg ggaggactcg gcctttcaag agcccgactc   1320
gccgctgccg cccgcgcgga gccccacgga gcccgggccc gagcgccgcc gctcgcccgg   1380
gccggccccc gggagccccg gcgagctgga ggaggacctg ttgctgcccg gcgcctgccc   1440
gggcgcggac gaggcgggcg gtggggcgga gggcgactcg tgggaggagg agggcttcgg   1500
ctcctcgtcg ccggtcaagt cgccggcggc cccctacttc ctgggtagct ctttctcgcc   1560
ggtgcgctgc ggcggcccag gagatgcgtc gccgcggggt tgcggggcgc gccgggcggg   1620
cgaaggccgc cgctcgccgc ggccggacca cccgggcacc ccgccacaca agaccttccg   1680
caagctgcga ctcttcgaca ccccgcacac gcccaagagt ttgctctcca aagctcgggg   1740
aattgattcc agctctgtta aactccgggg tagttctctc ttcatggata cagaaaaatc   1800
aggaaaaagg gaatttgatg tgcgacagac tcctcaagtg aatattaatc cttttactcc   1860
ggattctttg ttgcttcatt cctcaggaca gtgtcgtcgt agaaagagaa cgtattggaa   1920
tgattcctgt ggtgaagaca tggaagccag tgattatgag cttgaagatg aaacaagacc   1980
tgctaagaga attacaatta ctgaaagcaa tatgaagtcc cggtatacaa cagaatttca   2040
tgagctagag aaaatcggct ctggagaatt tggttctgta tttaagtgtg tgaagaggct   2100
ggatggatgc atttatgcca ttaagcgatc aaaaaagcca ttggcgggct ctgttgatga   2160
gcagaacgct ttgagagaag tatatgctca tgcagtgctt ggacagcatt ctcatgtagt   2220
tcgatatttc tctgcgtggg cagaagatga tcatatgctt atacagaatg aatattgtaa   2280
tggtggaagt ttagctgatg ctataagtga aaactacaga atcatgagtt actttaaaga   2340
agcagagttg aaggatctcc ttttgcaagt tggccgaggc ttgaggtata ttcattcaat   2400
gtctttggtt cacatggata taaaacctag taatattttc atatctcgaa cctcaatccc   2460
aaatgctgcc tctgaagaag gagacgaaga tgattgggca tccaacaaag ttatgtttaa   2520
aataggtgat cttgggcatg taacaaggat ctccagtcca caagttgaag agggcgatag   2580
tcgttttctt gcaaatgaag ttttacagga gaattatacc catctaccaa aagcagatat   2640
ttttgcgctt gccctcacag tggtatgtgc tgctggtgct gaacctcttc cgagaaatgg   2700
agatcaatgg catgaaatca gacagggtag attacctcgg ataccacaag tgctttccca   2760
agaatttaca gagttgctaa aagttatgat tcatccagat ccagagagaa gaccttcagc   2820
aatggcactg gtaaagcatt cagtattgct gtccgcttct agaaagagtg cagaacaatt   2880
acgaatagaa ttgaatgccg aaaagttcaa aaattcactt ttacaaaaag aactcaagaa   2940
agcacagatg gcaaaagctg cagctgagga aagagcactc ttcactgacc ggatggccac   3000
taggtccacc acccagagta atagaacatc tcgacttatt ggaaagaaaa tgaaccgctc   3060
tgtcagcctt actatatact gagctactcc tttcccacct ccccctgaac actgtgacaa   3120
gaggaagcta ggttgaaatc actgatagaa tccagtttgc aattactttc tcgattggtg   3180
tcagtagttt tactgattag gacttttatt gtgaattaca gttgaaagct gtattttgat   3240
gattgctatg tcaggctttc atctaatctt accagtctgt cttctgtagg atgtgtcact   3300
```

-continued

```
gttggatgtt acaccagcct ttccagggtt aaccactgtg gtggtgtgct gcttatagtt   3360

tgctgttgca ttgtaataaa aggtgtcttt ccctgtagtg acctgtaaaa agtactcaag   3420

ggctttatta cagacatacc ctccctttga aaagggacat gctaaaagac tcattactac   3480

tcagccttca atgtacctgt gtgtccatct tatatttctt tttttttttt aattgtgaat   3540

tagacttgta tatcccactg ggagcacttt gtaggcattg catgaaccat gggatgatga   3600

ttctgtggag gtattgcctt gtgaatttgc tgctatttta gttttgtctt tgctgtaaac   3660

ttgtagcatt aaacaatcat tgttgttaat aggtcttctt tttgaaacaa ttatgtgaaa   3720

tgtatagctg cttttgatga aaagcagcta tttgcctttt ttttttttcc tttgaacttt   3780

gaagctagtg cattggaaaa atgcaccctt tccctccttt ggaatgctgt attaatgtag   3840

tataataatt actggttttg taacttgttc tggtaatgtc cttcccggac tctttttaaa   3900

tgtctccccc taagttttat acttgattgt attattagtc tgtttttaaa tgttttgccc   3960

ggtttttctc ttcaatattt gtgtatataa accgatcttc gtgatactgt acatagctgt   4020

ttgaaatgcc agaatgactt ctgacattcc aagtttttca caaaatatat tttatctgtg   4080

attagccatt tgactaataa tactggctaa cagatgttga aaaaaattgt ctgtttgttt   4140

tctcattaat tttggtctaa aacatgtttg cacttgtctt tgacttgtgt tttattaaca   4200

ttgattggca tattaaaagt cactctgagc tt                                 4232
```

```
<210> SEQ ID NO 2
<211> LENGTH: 2189
<212> TYPE: DNA
<213> ORGANISM: Homo sapiens

<400> SEQUENCE: 2

gcagagggag cgagcgggcg gccggctagg gtggaagagc cgggcgagca gagctgcgct     60

gcgggcgtcc tgggaaggga gatccggagc gaataggggg cttcgcctct ggcccagccc    120

tcccgctgat cccccagcca gcggtccgca acccttgccg catccacgaa actttgccca    180

tagcagcggg cgggcacttt gcactggaac ttacaacacc cgagcaagga cgcgactctc    240

ccgacgcggg gaggctattc tgcccatttg gggacacttc cccgccgctg ccaggacccg    300

cttctctgaa aggctctcct tgcagctgct tagacgctgg atttttttcg ggtagtggaa    360

aaccagcagc ctcccgcgac gatgcccctc aacgttagct tcaccaacag gaactatgac    420

ctcgactacg actcggtgca gccgtatttc tactgcgacg aggaggagaa cttctaccag    480

cagcagcagc agagcgagct gcagcccccg gcgcccagcg aggatatctg gaagaaattc    540

gagctgctgc ccaccccgcc cctgtcccct agccgccgct ccgggctctg ctcgccctcc    600

tacgttgcgg tcacaccctt ctcccttcgg ggagacaacg acggcggtgg cgggagcttc    660

tccacggccg accagctgga gatggtgacc gagctgctgg gaggagacat ggtgaaccag    720

agtttcatct gcgacccgga cgacgagacc ttcatcaaaa acatcatcat ccaggactgt    780

atgtggagcg gcttctcggc cgccgccaag ctcgtctcag agaagctggc ctcctaccag    840

gctgcgcgca aagacagcgg cagcccgaac cccgcccgcg gccacagcgt ctgctccacc    900

tccagcttgt acctgcagga tctgagcgcc gccgcctcag agtgcatcga cccctcggtg    960

gtcttcccct accctctcaa cgacagcagc tcgcccaagt cctgcgcctc gcaagactcc   1020

agcgccttct ctccgtcctc ggattctctg ctctcctcga cggagtcctc cccgcagggc   1080

agccccgagc ccctggtgct ccatgaggag acaccgccca ccaccagcag cgactctgag   1140

gaggaacaag aagatgagga agaaatcgat gttgtttctg tggaaaagag gcaggctcct   1200
```

```
ggcaaaaggt cagagtctgg atcaccttct gctggaggcc acagcaaacc tcctcacagc   1260

ccactggtcc tcaagaggtg ccacgtctcc acacatcagc acaactacgc agcgcctccc   1320

tccactcgga aggactatcc tgctgccaag agggtcaagt tggacagtgt cagagtcctg   1380

agacagatca gcaacaaccg aaaatgcacc agccccaggt cctcggacac cgaggagaat   1440

gtcaagaggc gaacacacaa cgtcttggag cgccagagga ggaacgagct aaaacggagc   1500

tttttgccc tgcgtgacca gatcccggag ttggaaaaca atgaaaaggc ccccaaggta   1560

gttatcctta aaaaagccac agcatacatc ctgtccgtcc aagcagagga gcaaaagctc   1620

atttctgaag aggacttgtt gcggaaacga cgagaacagt tgaaacacaa acttgaacag   1680

ctacggaact cttgtgcgta aggaaaagta aggaaaacga ttccttctaa cagaaatgtc   1740

ctgagcaatc acctatgaac ttgtttcaaa tgcatgatca aatgcaacct cacaaccttg   1800

gctgagtctt gagactgaaa gatttagcca taatgtaaac tgcctcaaat tggactttgg   1860

gcataaaaga actttttat gcttaccatc tttttttttt ctttaacaga tttgtattta   1920

agaattgttt ttaaaaaatt ttaagattta cacaatgttt ctctgtaaat attgccatta   1980

aatgtaaata actttaataa aacgtttata gcagttacac agaatttcaa tcctagtata   2040

tagtacctag tattataggt actataaacc ctaatttttt ttatttaagt acattttgct   2100

ttttaaagtt gatttttttc tattgttttt agaaaaaaata aaataactgg caaatatatc   2160

attgagccaa aaaaaaaaaa aaaaaaaaa                                     2189


<210> SEQ ID NO 3
<211> LENGTH: 2352
<212> TYPE: DNA
<213> ORGANISM: Homo sapiens

<400> SEQUENCE: 3

gaaacttaaa ggtgtttacc ttgtcatcag catgtaagct aattatctcg ggcaagatgt     60

aggcttctat tgtcttgttg ctttagcgct tacgccccgc ctctggtggc tgcctaaaac    120

ctggcgccgg gctaaaacaa acgcgaggca gcccccgagc ctccactcaa gccaattaag    180

gaggactcgg tccactccgt tacgtgtaca tccaacaaga tcggcgttaa ggtaacacca    240

gaatatttgg caaagggaga aaaaaaaagc agcgaggctt cgccttcccc ctctcccttt    300

tttttcctcc tcttccttcc tcctccagcc gccgccgaat catgtcgatg agtccaaagc    360

acacgactcc gttctcagtg tctgacatct tgagtcccct ggaggaaagc tacaagaaag    420

tgggcatgga gggcggcggc ctcggggctc cgctggcggc gtacaggcag ggccaggcgg    480

caccgccaac agcggccatg cagcagcacg ccgtggggca ccacggcgcc gtcaccgccg    540

cctaccacat gacggcggcg ggggtgcccc agctctcgca ctccgccgtg gggggctact    600

gcaacggcaa cctgggcaac atgagcgagc tgccgccgta ccaggacacc atgaggaaca    660

gcgcctctgg ccccggatgg tacggcgcca acccagaccc gcgcttcccc gccatctccc    720

gcttcatggg cccggcgagc ggcatgaaca tgagcggcat gggcggcctg ggctcgctgg    780

gggacgtgag caagaacatg gccccgctgc caagcgcgcc gcgcaggaag cgccgggtgc    840

tcttctcgca ggcgcaggtg tacgagctgg agcgacgctt caagcaacag aagtacctgt    900

cggcgccgga gcgcgagcac ctggccagca tgatccacct gacgcccacg caggtcaaga    960

tctggttcca gaaccaccgc tacaaaatga agcgccaggc caaggacaag gcggcgcagc   1020

agcaactgca gcaggacagc ggcggcggcg ggggcggcgg gggcaccggg tgcccgcagc   1080

agcaacaggc tcagcagcag tcgccgcgac gcgtggcggt gccggtcctg gtgaaagacg   1140
```

```
gcaaaccgtg ccaggcgggt gcccccgcgc cgggcgccgc cagcctacaa ggccacgcgc   1200

agcagcaggc gcagcaccag gcgcaggccg cgcaggcggc ggcagcggcc atctccgtgg   1260

gcagcggtgg cgccggcctt ggcgcacacc cgggccacca gccaggcagc gcaggccagt   1320

ctccggacct ggcgcaccac gccgccagcc ccgcggcgct gcagggccag gtatccagcc   1380

tgtcccacct gaactcctcg ggctcggact acggcaccat gtcctgctcc accttgctat   1440

acggtcggac ctggtgagag gacgccgggc cggccctagc ccagcgctct gcctcaccgc   1500

ttccctcctg cccgccacac agaccaccat ccaccgctgc tccacgcgct tcgacttttc   1560

ttaacaacct ggccgcgttt agaccaagga acaaaaaaac cacaaaggcc aaactgctgg   1620

acgtctttct tttttcccc ccctaaaatt tgtgggtttt ttttttaaa aaaagaaaat   1680

gaaaaacaac caagcgcatc caatctcaag gaatctttaa gcagagaagg gcataaaaca   1740

gctttggggt gtcttttttt ggtgattcaa atgggttttc cacgctaggg cggggcacag   1800

attggagagg gctctgtgct gacatggctc tggactctaa agaccaaact tcactctggg   1860

cacactctgc cagcaaagag gactcgcttg taaataccag gatttttttt tttttttgaa   1920

gggaggacgg gagctgggga gaggaaagag tcttcaacat aacccacttg tcactgacac   1980

aaaggaagtg ccccctcccc ggcaccctct ggccgcctag gctcagcggc gaccgccctc   2040

cgcgaaaata gtttgtttaa tgtgaacttg tagctgtaaa acgctgtcaa aagttggact   2100

aaatgcctag tttttagtaa tctgtacatt ttgttgtaaa aagaaaaacc actcccagtc   2160

cccagccctt cacatttttt atgggcattg acaaatctgt gtatattatt tggcagtttg   2220

gtatttgcgg cgtcagtctt tttctgttgt aacttatgta gatatttggc ttaaatatag   2280

ttcctaagaa gcttctaata aattatacaa attaaaaaga ttcttttctt gattaaaaaa   2340

aaaaaaaaaa aa                                                        2352
```

```
<210> SEQ ID NO 4
<211> LENGTH: 431
<212> TYPE: DNA
<213> ORGANISM: Homo sapiens
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t

<400> SEQUENCE: 4

cagcagcgga gacccatcct ctgacccccct tggctctcca accctcctcg ctttgtgagg     60

cacccgagcc ttactccctg caggtgccac cctaagcaac gtctgctccc cttcccccac    120

cagtccagct ggcctggaca gtatcccata cccaactcca gcagctgctt ctccatccct    180

ctaatgagac taaccatatt gtgcttcaca gtagagccag cttggggcca ccaaagctgc    240

ccattgtttc tctaggagct gggcctctct aggcacaatt tggcactaaa tcaggaggac    300

aaaatatttt cccatttctg gccggaggaa ttccggggga ggcccaggag gantttgtta    360

ggattcctta ggagggtcct ctggggaggc cctaaaccct ttccagattc attggccaca    420

tttttcccnt c                                                         431
```

```
<210> SEQ ID NO 5
<211> LENGTH: 292
<212> TYPE: DNA
<213> ORGANISM: Homo sapiens
<220> FEATURE:
```

<221> NAME/KEY: misc_feature
<222> LOCATION: (286)..(286)
<223> OTHER INFORMATION: n is a, c, g, or t

<400> SEQUENCE: 5

```
gtttttgatg cagacataaa aatagcaatc attttaaatt gtcaaaattt ccagattact     60

ggtaaaaatt atttgaaaac aaacttatgg gtaataaagg ctagtcagaa ccctatacca    120

taaagtgtag ttaccataca gattaatatg tagcaaaaat gtatgcttga tatttctcaa    180

ctgtgttaat ttttctgctg tattccagct gaccaaaaca atattaagaa tgcatcttta    240

taaatggggt gctaattgat aatgggaaat aatttaggta atgggnctat ac            292
```

<210> SEQ ID NO 6
<211> LENGTH: 400
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (350)..(350)

<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t

<400> SEQUENCE: 6
ngaagggata gccagcgcga aggaagtnct ggagtcgtgt gttttggctg cgcgtgatcc 60
tgcgtgggtc gggaggtgtt tctgtgtagg tntctggccc tttnatcagt cgtgcggagg 120
accgcgtgat ttccttccag ttctnctcgg ntttcangaa aagcctaaag attagactnt 180
aagaaaagan aatagaagcc atgtttcgaa gacctgtatt acaggtactt cgtcagtttc 240
taagacatga gtcccganac aactaccagt ttggttcttn gaaagatccc tggaatgcac 300
tttnctttng gcccaggtng ggtcagggac cctgtctttt taggacaggn tcggaaggga 360
aaaaaatccc agttcacaat anttttntc ttaggcaact 400

<210> SEQ ID NO 7
<211> LENGTH: 859
<212> TYPE: DNA
<213> ORGANISM: Homo sapiens

<400> SEQUENCE: 7
acaggagagc atagcacctg cagcaagatg gatgtgggca gcaaagaggt cctgatggag 60
agcccgccgg actactccgc agctccccgg ggccgatttg gcattccctg ctgcccagtg 120
cacctgaaac gccttcttat cgtggtggtg gtggtggtcc tcatcgtcgt ggtgattgtg 180
ggagccctgc tcatgggtct ccacatgagc cagaaacaca cggagatggt tctggagatg 240
agcattgggg cgccggaagc ccagcaacgc ctggccctga gtgagcacct ggttaccact 300
gccaccttct ccatcggctc cactggcctc gtggtgtatg actaccagca gctgctgatc 360
gcctacaagc cagcccctgg cacctgctgc tacatcatga agatagctcc agagagcatc 420
cccagtcttg aggctctcaa tagaaaagtc cacaacttcc agatggaatg ctctctgcag 480
gccaagcccg cagtgcctac gtctaagctg ggccaggcag aggggcgaga tgcaggctca 540
gcaccctccg gaggggaccc ggccttcttg ggcatggccg tgaacaccct gtgtggcgag 600
gtgccgctct actacatcta ggacgcctcc ggtgagcagg gtcagtggaa gccccaacgg 660
gaaaggaaac gccccgggca aagggtcttt tgcagctttt gcagacgggc aagaagctgc 720
ttctgcccac accgcaggga caaaccctgg agaaatggga gcttggggag aggatgggag 780
tgggcagagg tggcacccag gggcccggga actcctgcca caacagaata aagcagcctg 840
atttgaaaag caaaaaaaa 859

<210> SEQ ID NO 8
<211> LENGTH: 4050
<212> TYPE: DNA
<213> ORGANISM: Homo sapiens

<400> SEQUENCE: 8
cttgcaatcc aggctttcct tggaagtggc tgtaacatgt atgaaaagaa agaaaggagg 60
accaagagat gaaagagggc tgcacgcgtg ggggcccgag tggtgggcgg ggacagtcgt 120
cttgttacag ggtgctggc cttccctggc gcctgcccct gtcggccccg cccgagaacc 180
tccctgcgcc agggcagggt ttactcatcc cggcgaggtg atcccatgcg cgagggcggg 240

-continued

```
cgcaagggcg gccagagaac ccagcaatcc gagtatgcgg catcagccct tcccaccagg    300
cacttccttc cttttcccga acgtccaggg agggagggcc gggcacttat aaactcgagc    360
cctggccgat ccgcatgtca gaggctgcct cgcaggggct gcgcgcacgg caagaagtgt    420
ctgggctggg acggacagga gaggctgtcg ccatcggcgt cctgtgcccc tctgctccgg    480
cacggccctg tcgcagtgcc cgcgctttcc ccggcgcctg cacgcggcgc gcctgggtaa    540
catgcttggg gtcctggtcc ttggcgcgct ggccctggcc ggcctggggt tccccgcacc    600
cgcagagccg cagccgggtg gcagccagtg cgtcgagcac gactgcttcg cgctctaccc    660
gggccccgcg accttcctca atgccagtca gatctgcgac ggactgcggg gccacctaat    720
gacagtgcgc tcctcggtgg ctgccgatgt catttccttg ctactgaacg gcgacggcgg    780
cgttggccgc cggcgcctct ggatcggcct gcagctgcca cccggctgcg gcgaccccaa    840
gcgcctcggg cccctgcgcg gcttccagtg ggttacggga gacaacaaca ccagctatag    900
caggtgggca cggctcgacc tcaatggggc tcccctctgc ggcccgttgt gcgtcgctgt    960
ctccgctgct gaggccactg tgcccagcga gccgatctgg gaggagcagc agtgcgaagt   1020
gaaggccgat ggcttcctct gcgagttcca cttcccagcc acctgcaggc cactggctgt   1080
ggagcccggc gccgcggctg ccgccgtctc gatcacctac ggcaccccgt tcgcggcccg   1140
cggagcggac ttccaggcgc tgccggtggg cagctccgcc gcggtggctc ccctcggctt   1200
acagctaatg tgcaccgcgc cgcccggagc ggtccagggg cactgggcca gggaggcgcc   1260
gggcgcttgg gactgcagcg tggagaacgg cggctgcgag cacgcgtgca atgcgatccc   1320
tggggctccc cgctgccagt gcccagccgg cgccgccctg caggcagacg ggcgctcctg   1380
caccgcatcc gcgacgcagt cctgcaacga cctctgcgag cacttctgcg ttcccaaccc   1440
cgaccagccg ggctcctact cgtgcatgtg cgagaccggc taccggctgg cggccgacca   1500
acaccggtgc gaggacgtgg atgactgcat actggagccc agtccgtgtc cgcagcgctg   1560
tgtcaacaca cagggtggct tcgagtgcca ctgctaccct aactacgacc tggtggacgg   1620
cgagtgtgtg gagcccgtgg acccgtgctt cagagccaac tgcgagtacc agtgccagcc   1680
cctgaaccaa actagctacc tctgcgtctg cgccgagggc ttcgcgccca ttccccacga   1740
gccgcacagg tgccagatgt tttgcaacca gactgcctgt ccagccgact gcgaccccaa   1800
cacccaggct agctgtgagt gccctgaagg ctacatcctg gacgacggtt tcatctgcac   1860
ggacatcgac gagtgcgaaa acggcggctt ctgctccggg gtgtgccaca acctccccgg   1920
taccttcgag tgcatctgcg ggcccgactc ggcccttgcc cgccacattg gcaccgactg   1980
tgactccggc aaggtggacg gtggcgacag cggctctggc gagcccccgc ccagcccgac   2040
gcccggctcc accttgactc ctccggccgt ggggctcgtg cattcgggct tgctcatagg   2100
catctccatc gcgagcctgt gcctggtggt ggcgcttttg gcgctcctct gccacctgcg   2160
caagaagcag ggcgccgcca gggccaagat ggagtacaag tgcgcggccc cttccaagga   2220
ggtagtgctg cagcacgtgc ggaccgagcg gacgccgcag agactctgag cggcctccgt   2280
ccaggagcct ggctccgtcc aggagctgtg cctcctcacc cccagctttg ctaccaaagc   2340
accttagctg gcattacagc tggagaagac cctccccgca ccccccaagc tgttttcttc   2400
tattccatgg ctaactggcg agggggtgat tagagggagg agaatgagcc tcggcctctt   2460
ccgtgacgtc actggaccac tgggcaatga tggcaatttt gtaacgaaga cacagactgc   2520
gatttgtccc aggtcctcac taccgggcgc aggagggtga gcgttattgg tcggcagcct   2580
tctgggcaga ccttgacctc gtgggctagg gatgactaaa atatttattt tttttaagta   2640
```

```
tttaggtttt tgtttgtttc ctttgttctt acctgtatgt ctccagtatc cactttgcac   2700

agctctccgg tctctctctc tctacaaact cccacttgtc atgtgacagg taaactatct   2760

tggtgaattt ttttttccta gccctctcac atttatgaag caagccccac ttattcccca   2820

ttcttcctag ttttctcctc ccaggaactg ggccaactca cctgagtcac cctacctgtg   2880

cctgacccta cttcttttgc tcatctagct gtctgctcag acagaacccc tacatgaaac   2940

agaaacaaaa acactaaaaa taaaaatggc catttgcttt ttcaccagat ttgctaattt   3000

atcctgaaat ttcagattcc cagagcaaaa taattttaaa caaagggttg agatgtaaaa   3060

ggtattaaat tgatgttgct ggactgtcat agaaattaca cccaaagagg tatttatctt   3120

tacttttaaa cagtgagcct gaattttgtt gctgttttga tttgtactga aaaatggtaa   3180

ttgttgctaa tcttcttatg caatttcctt ttttgttatt attacttatt tttgacagtg   3240

ttgaaaatgt tcagaaggtt gctctagatt gagagaagag acaaacacct cccaggagac   3300

agttcaagaa agcttcaaac tgcatgattc atgccaatta gcaattgact gtcactgttc   3360

cttgtcactg gtagaccaaa ataaaaccag ctctactggt cttgtggaat tgggagcttg   3420

ggaatggatc ctggaggatg cccaattagg gcctagcctt aatcaggtcc tcagagaatt   3480

tctaccattt cagagaggcc ttttggaatg tggcccctga acaagaattg gaagctgccc   3540

tgcccatggg agctggttag aaatgcagaa tcctaggctc caccccatcc agttcatgag   3600

aatctatatt taacaagatc tgcagggggt gtgtctgctc agtaatttga ggacaaccat   3660

tccagactgc ttccaatttt ctggaataca tgaaatatag atcagttata agtagcaggc   3720

caagtcaggc ccttattttc aagaaactga ggaattttct ttgtgtagct ttgctctttg   3780

gtagaaaagg ctaggtacac agctctagac actgccacac agggtctgca aggtctttgg   3840

ttcagctaag ctaggaatga aatcctgctt cagtgtatgg aaataaatgt atcatagaaa   3900

tgtaactttt gtaagacaaa ggttttcctc ttctattttg taaactcaaa atatttgtac   3960

atagttattt atttattgga gataatctag aacacaggca aaatccttgc ttatgacatc   4020

acttgtacaa aataaacaaa taacaatgtg                                    4050
```

```
<210> SEQ ID NO 9
<211> LENGTH: 466
<212> TYPE: DNA
<213> ORGANISM: Homo sapiens
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t

<400> SEQUENCE: 9

tttttttttt tttttttttt taagtctcct tctttattat taggaaaaca acaacaacaa     60

caaacaaaaa aatggcgtca tgaatatgaa cagcattgtc agatgaatta gttgaagtgg    120

tttttttttt gttttttttt tttttttgt actgngtcct caaatttaat ggattaatgt    180

gtcttgtata tataaaaaga aaacctctac cttcagcctc tgcctattct tgctccgtct    240

aggacatccn caatttcgtc gatgaccagc ttggtgaata agtattactg taccaactgg    300

gcctcctcta gcaggcccct gaaggcagtg gaataaaatg aaatcttcgc cctttaagaa    360
```

```
ctcctgacct taatgtggta gtagtatctt gtccttgagg ggatttcctt cccctcaccc    420

ctaagacttt cacaacctgg tgactggaaa gaaccaccac naatcc                   466


<210> SEQ ID NO 10
<211> LENGTH: 470
<212> TYPE: DNA
<213> ORGANISM: Homo sapiens
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t

<400> SEQUENCE: 10

aacaaatgct tctgccaaag tgaaagaatt ttatgtctta atgcttttct ttaaaaaaaa     60

aaaaagtcaa cattgaacta ggacatgctc tgcttcccca cccccatttt gctgactaca    120

ttttaaaaaa tctattggca gaaaacaaga tattttcttc aaatagagtg attatgtttt    180

attgctattt tgtttagtat atattttnct caattgggaa aaaaatctag gtgaaaaaaa    240

ttacctaaca agagaagtag tttacatagt cataacattt aaatttgctg cccaaaaaat    300

gtaaaanaat ttnaatgtaa aatgtcacat antttcaaaa aacttacctc aattgtctat    360

catttatcat gtactataag tcaacttcct aaataagatt cagtccttta ttataagccc    420

ctactggtac catngtatac attaaaaacg ctnctccaaa atttcctggc               470


<210> SEQ ID NO 11
<211> LENGTH: 1007
<212> TYPE: DNA
<213> ORGANISM: Homo sapiens

<400> SEQUENCE: 11

aactccaggg ctagtgagct ggaccggaag taggtttcta cccgaccgca ttttacgtgg     60

tgctgcattt ccggtagcgg cggcgggaaa tcggctgtgg gagagaggct aggcctctga    120

ggaggcgaat ccggcgggta tcagagccat cagaaccgcc accatgacgg tgggcaagag    180

cagcaagatg ctgcagcata ttgattacag gatgaggtgc atcctgcagg acggccggat    240

cttcattggc accttcaagg cttttgacaa gcacatgaat ttgatcctct gtgactgtga    300

tgagttcaga aagatcaagc caaagaactc caaacaagca gaaagggaag agaagcgagt    360

cctcggtctg gtgctgctgc gaggggagaa tctggtctca atgacagtag agggacctcc    420

tcccaaagat actggtattg ctcgagttcc acttgctgga gctgccgggg gcccagggat    480

cggcagggct gctggcagag gaatcccagc tggggttccc atgccccagg ctcctgcagg    540

acttgctggg ccagtccgtg ggttggcgg gccatcccaa caggtgatga ccccacaagg     600
```

```
aagaggtact gttgcagccg ctgcagctgc tgccacagcc agtattgccg gggctccaac    660

ccagtaccca cctggccgtg gggtcctcc cccacctatg ggccgaggag cacccccctcc    720

aggcatgatg ggcccacctc ctggtatgag acctcctatg ggtcccccaa tggggatccc    780

ccctggaaga gggactccaa tgggcatgcc ccctccggga atgcggcctc ctccccctgg    840

gatgcgaggg ccccctcccc cgggaatgcg cccaccaagg ccctagactc atcttggccc    900

tcctcagctc cctgcctgtt tcccgtaagg ctgtacatag tccttttatc tccttgtggc    960

ctatgaaact ggtttataat aaactcttaa gagaacatta taattgc                 1007
```

<210> SEQ ID NO 12
<211> LENGTH: 3582
<212> TYPE: DNA
<213> ORGANISM: Homo sapiens

<400> SEQUENCE: 12

```
ctgctcgcgg cgccgcctcc tgctcctccc gctgctgctg ccgctgccgc cctgagtcac      60

tgcctgcgca gctccggccg cctggctccc catactagtc gccgatattt ggagttctta    120

caacatggca gacattgaca acaaagaaca gtctgaactt gatcaagatt tggatgatgt    180

tgaagaagta gaagaagagg aaactggtga agaaacaaaa ctcaaagcac gtcagctaac    240

tgttcagatg atgcaaaatc ctcagattct tgcagccctt caagaaagac ttgatggtct    300

ggtagaaaca ccaacaggat acattgaaag cctgcctagg gtagttaaaa gacgagtgaa    360

tgctctcaaa aacctgcaag ttaaatgtgc acagatagaa gccaaattct atgaggaagt    420

tcacgatctt gaaaggaagt atgctgttct ctatcagcct ctatttgata agcgatttga    480

aattattaat gcaatttatg aacctacgga agaagaatgt gaatggaaac cagatgaaga    540

agatgagatt tcggaggaat tgaaagaaaa ggccaagatt gaagatgaga aaaaggatga    600

agaaaaagaa gaccccaaag gaattcctga attttggtta actgttttta agaatgttga    660

cttgctcagt gatatggttc aggaacacga tgaacctatt ctgaagcact tgaaagatat    720

taaagtgaag ttctcagatg ctggccagcc tatgagtttt gtcttagaat ttcactttga    780

acccaatgaa tattttacaa atgaagtgct gacaaagaca tacaggatga ggtcagaacc    840

agatgattct gatccctttt cttttgatgg accagaaatt atgggttgta cagggtgcca    900

gatagattgg aaaaaaggaa agaatgtcac tttgaaaact attaagaaga agcagaaaca    960

caagggacgt gggacagttc gtactgtgac taaaacagtt tccaatgact ctttctttaa   1020

ctttttgcc cctcctgaag ttcctgagag tggagatctg gatgatgatg ctgaagctat   1080

ccttgctgca gacttcgaaa ttggtcactt tttacgtgag cgtataatcc caagatcagt   1140

gttatatttt actggagaag ctattgaaga tgatgatgat gattatgatg aagaaggtga   1200

agaagcggat gaggaagggg aagaagaagg agatgaggaa aatgatccag actatgaccc   1260

aaagaaggat caaaacccag cagagtgcaa gcagcagtga agcaggatgt atgtggcctt   1320

gaggataacc tgcactgtaa tagcctaaac acaactctta tttacttaca gccttatgtt   1380

tttgtatttt cttggtagac taggtaattt ttttttaaag gacaggaaac tgatatttta   1440

aagaccaatt tgttctacct agcattttaa ctagtttttc tgccagctat gttgaatgca   1500

caaattctgt cacgcatgtt cattcattgc tacataattt ggttcttctg gaatattttt   1560

atgtagctct tggagtacag ctatgaaaat taacaactgt taaaggaaat accttttttt   1620

tttttttgta attttttcct tgaagaacca aagtattttt tcagctggtt gttgaatagg   1680

gttaagtccg cttggattag ctgtgccttt cattactttg ttacagaaat gcagtgactt   1740
```

```
atactaagac aatttattgt ttaaaaaaaa aattggcaag acaactatat ggttaagaat   1800

ttccagtatg accacaccca ataactgtta ttagagtgtt aatggattat tgtgttttag   1860

gtgacatagt taactgtaaa gtaacctgac tcagtatagt tactggtacc acagtgaggt   1920

gaataaaacg ggattttcag aagttagcct gaatttaact gtatttttaa atttaacctc   1980

cattaactaa gcatcttttc tttgtggtag ggtctacctt ctgcttccct ggaaaggatg   2040

aatttacatc atttgacaag cctattttca agttatttgt tgtttgtttg cttgtttttg   2100

tttttgcagc taaaataaaa atttcaaata caattttagt tcttacaaga taatgtctta   2160

attttgtacc aattcaggta gaagtagagg cctaccttga attaagggtt atactcagtt   2220

tttaacacat tgttgaagaa aaggtaccag ctttggaacg agatgctata ctaataagca   2280

agtgtaaaaa aaaaaaaaaa agaggaagaa aatcttaagt gattgatgct gttttctttt   2340

aaaaaaaaaa aaaaaaattc attttctttg ggttagagct agagagaagg ccccaagctt   2400

ctatggtttc ttctaattct tattgcttaa agtatgagta tgtcacttac ccgtgcttct   2460

gtttactgtg taattaaaat gggtagtact gtttacctaa ctacctcatg gatgtgttaa   2520

ggcatattga gttaaatctc atataatgtt tctcaatctt gttaaaagct caaaattttg   2580

ggcctatttg taatgccagt gtgacactaa gcattttgtt cacaccacgc tttgataact   2640

aaactggaaa acaaaggtgt taagtacctc tgttctggat ctgggcagtc agcactcttt   2700

ttagatcttt gtgtggctcc tatttttata gaagtggagg gatgcactat ttcacaaggt   2760

ccaagatttg ttttcagata tttttgatga ctgtattgta aatactacag ggatagcact   2820

atagtattgt agtcatgaga cttaaagtgg aaataagact atttttgaca aaagatgcca   2880

ttaaatttca gactgtagag ccacatttac aatacctcag gctaattact gttaattttg   2940

gggttgaact ttttttgaca gtgagggtgg attattggat tgtcattaga ggaaggtcta   3000

gatttcctgc tcttaataaa attacattga attgattttt agaggtaatg aaaacttcct   3060

ttctgagaag ttagtgttaa ggtcttggaa tgtgaacaca ttgtttgtag tgctatccat   3120

tcctctcctg agattttaac ttactactgg aaatccttaa ccaattataa tagctttttt   3180

tctttatttt caaaatgatt tcctttgctt tgattagaca ctatgtgctt ttttttttta   3240

accatagttc atcgaaatgc agctttttct gaacttcaaa gatagaatcc catttttaat   3300

gaactgaagt agcaaaatca tctttttcat tctttaggaa atagctattg ccaaagtgaa   3360

ggtgtagata atacctagtc ttgttacata aaggggatgt ggtttgcaga agaattttct   3420

ttataaaatt gaagttttaa gggacgtcag tgtttatgcc atttttccag ttccaaaatg   3480

attccattcc attctagaaa tttgaagtat gtaacctgaa atccttaata aaatttggat   3540

ttaattttat aaaaaaaaaa aaaaaaaaaa aaaaaaaaaa aa                     3582
```

<210> SEQ ID NO 13
<211> LENGTH: 6232
<212> TYPE: DNA
<213> ORGANISM: Homo sapiens

<400> SEQUENCE: 13

```
ctgccagatc agtttgtcac cacccaggct cccttgcctt tggctgggtg caacttccat     60

tttaggtgtt ggatctgagg gggaaaaaaa agagagaggg agagagagag aaagaagagc    120

aggaaagatc ccgaaaggag gaagaggtgg cgaaaaatca actgccctgc tggatttgtc    180

tttctcagca ccttggcgaa gccttgggtt tctttcttaa aggactgatt tttagaactc    240

cacatttgag gtgtgtggct tttgaagaaa atgtatgtac tgacgggaaa aggaagataa    300
```

```
gcaagtcgaa tttttgtctt acgctctctc cttcctgctt cctccttgct gtggtggctg    360
ggatgctcct tccatgattt tttgaatcta gactgggctg ttctctgtgt taaaccaatc    420
agttgcgacc ttctcttaac agtgtgaagt gagggggtct ctctccctcc ttctccttcc    480
tctgtgattc accttccttt ttaccctgcc ctgcggcggc tccgcccctt accttcatgg    540
acgactcaga ggtggagtcg accgccagca tcttggcctc tgtgaaggaa caagaggccc    600
agtttgagaa gctgacccgg gcgctggagg aggaacggcg ccacgtctcg gcgcagctgg    660
aacgcgtccg ggtctcacca caagatgcca acccactcat ggccaacggc acactcaccc    720
gccggcatca gaacggccgg tttgtgggcg atgctgacct tgaaagacag aaattttcag    780
atttgaaact caacggaccc caggatcaca gtcaccttct atatagcacc atccccagga    840
tgcaggagcc ggggcagatt gtggagacct acacggagga ggatcctgag ggagccatgt    900
ctgtagtctc tgtggagacc tcagatgatg ggaccactcg gcgcacagag accacggtca    960
agaaagtagt gaagactgtg acaacacgga cagtacagcc agtcgctatg ggaccagacg   1020
ggttgcctgt ggatgcttca tcagtttcta acaactatat ccagactttg ggtcgtgatt   1080
tccgcaagaa tggcaatggg ggacctggtc cctatgtggg gcaagctggc actgctaccc   1140
ttcctaggaa cttccactac cctcctgatg gttatagtcg ccactatgaa gatggttatc   1200
caggtggcag tgataactat ggcagtctgt cccgggtgac ccgcattgag gagcggtata   1260
ggcccagcat ggaaggctac cgggcaccta gtagacagga tgtgtatggg ccccaacccc   1320
aggttcgggt aggtgggagc agcgtggatc tgcatcgctt tcatccagag ccttatgggc   1380
tagaggatga ccagcgtagt atgggctatg atgacctgga ttatggtatg atgtctgatt   1440
atggcactgc ccgtcggact gggacaccct ctgaccctcg tcggcgcctc aggagctatg   1500
aagacatgat tggtgaggag gtgccatcgg atcaatacta ctgggctcct ttggcccagc   1560
atgagcgagg aagtttagca agcttggata gcctgcgcaa aggagggcct ccacctccta   1620
attggagaca gccagagctg ccagaggtga tcgccatgct tggattccgc ttggatgctg   1680
tcaagtccaa tgcagctgca tacctgcaac acttatgcta ccgcaatgac aaggtgaaga   1740
ctgacgtgcg gaagctcaag ggcatcccag tactggtggg attgttagac catcccaaaa   1800
aggaagtgca ccttggagcc tgtggagctc tcaagaatat ctcttttgga cgtgaccagg   1860
ataacaagat tgccataaaa aactgtgatg gtgtgcctgc ccttgtgcga ttgcttcgaa   1920
aggctcgtga tatggacctt actgaagtta ttaccggaac cctgtggaat ctttcatccc   1980
atgactcaat caaaatggag attgtggacc atgcactgca tgccttgaca gatgaagtga   2040
tcattcctca ttctggttgg gagcgggaac ctaatgaaga ctgtaagcca cgccatattg   2100
agtgggaatc ggtgctcacc aacacagctg gctgccttag gaatgtaagc tcagagagga   2160
gtgaagctcg ccggaaactt cgggaatgtg atggtttagt tgatgccctc attttcattg   2220
ttcaggctga gattgggcag aaggattcag acagcaagct tgtagagaac tgtgtttgcc   2280
ttcttcggaa cttatcatat caagttcacc gggagatccc acaggcagag cgttaccaag   2340
aggcagctcc caatgttgcc aacaatactg ggccacatgc tgccagttgc tttggggcca   2400
agaagggcaa agggaaaaaa cctatagagg atccagcaaa cgatacagtg gatttcccta   2460
aaagaacgag tccagctcga ggctatgagc tcttatttca gccagaggtg gttcggatat   2520
acatctcact tcttaaggag agcaagactc ctgccatcct agaagcctca gctggagcta   2580
tccagaactt gtgtgctggg cgctggacgt atggtcgata catccgctct gctctgcgtc   2640
aagagaaggc tctttctgcc atagctgacc tcctgactaa tgaacatgaa cgggtggtga   2700
```

```
aagctgcatc tggagcactg agaaacctgg ctgtggatgc tcgcaacaaa gaattaattg   2760
gtaaacatgc tattcctaac ttggtaaaga atctgccagg aggacagcag aactcctctt   2820
ggaatttctc tgaggacact gtcatctcta ttttgaacac tatcaacgag gttatcgctg   2880
agaacttgga ggctgccaaa aagcttcgag agacacaggg tattgagaag ctggtgttga   2940
tcaacaaatc agggaaccgc tcagaaaaag aagttcgagc agcagcactt gtattacaga   3000
caatctgggg atataaggaa ctgcggaagc cactggaaaa agaaggatgg aagaaatcag   3060
actttcaggt gaatctaaac aatgcttccc gaagccagag cagtcattca tatgatgata   3120
gtactctccc tctcattgac cggaaccaaa aatcagataa caactattcc acaccaaatg   3180
agagaggaga ccacaataga acactggatc gatcggggga tctaggcgac atggagccat   3240
tgaagggaac aacacccttg atgcaggacg aggggcagga atctctggag gaagagttgg   3300
atgtgttggt tttggatgat gaggggggcc aagtgtctta cccctccatg cagaagattt   3360
agcaccacta tctccgttcc atctgggctt atatgtactt ttattttttg gtggtgaaat   3420
tgactgatga ttttcctttt tcttcgctgg actattgtgc caactgccag gctgcctcct   3480
gcccttacag ccctaagtgg ctgccttctt tccatcaact cccaacttct tcctgtgaag   3540
tttaattgtc tcaacgcctc cccctccccc attccctcca tttttctccc aagaaacctg   3600
actcaattat ttgcatattt tgagaaactg ctgcagatta gttctttttg ccagttttcc   3660
ctggaactcc tggccttttg tggaggggag ggatggagag aataggaatc ttcactagaa   3720
gccgtgggaa gaattggaag ttacatgctg tatatgcaat gtccagcagt ctgataaact   3780
gacgattctt aatcaagatt tttttcctga tggggaaggg acttttattt tcttttagag   3840
aggggaaagt gtgagctctt cccttattcc taatggctat ttttgaagca aagaaggcca   3900
gcaacattgg cacatgccac ctggcaaagg acccttgagt aagtgaaggt ctcctaaaac   3960
tgggattaag aaaccttgct ctcctcatct ccaaggcagg gaccatcaag aacctacaga   4020
ctccatctct tctgcaagcc tcatgccaac cctgggctat tgctgctgcc ccttaaacac   4080
aggctgtcct taacccacct ctcctgccct gtgatatgtc tgctgagttg gcctggccat   4140
ttccaagagg ctgtagaaag gggagaatgt caaggaagac ttttggtaga gaaggagcag   4200
aaagatgtgt ttttgggaag aagaagacct ctaggaggag ctagtaggaa tgtacatgaa   4260
gcaattagtc tgaaactggc ttccccactc ccccgtttct ccttttccta tccttatagg   4320
cctgtccctt gcctctgccc tggattggtt ggcaaactat aggacttgat gtacataact   4380
cctgtccctt ttcccttaca aggtggggat tgcccctggc tttgcctctt ctttgtgcct   4440
ttggcctggg gtgcatctcc tcccgccctt ccatgtgcct ttctttgcct ctgcagtctc   4500
atttctcata attttgcaaa ttatattttg ttgctttctt acctactatt ggccctaaat   4560
agcagaaaga agagaagtga ccgagagaac ctcagattct tcattgagga ttggtatagc   4620
catgatttca gtcatagcaa gcttttgctc aacagcatat gggtgggatt tggcaaaaat   4680
cctattctga tgaatctcaa agtaaggctg gtaagagaag tgagtggtgt gactcttact   4740
ccttaggtgc ccagaattta ccatcatctc tgaaggagtt acagggaagt ggtctcccca   4800
attctcccct ccctccagta ttgccccctc tcactttagc atatattaat tagcaggttg   4860
ggctagagaa atcagctgct atgcgggttg attattatta ttatttctaa tccttttcct   4920
tatttgcctt ctactcccct taatctaatc taaaagctct gttccatgca actggagttc   4980
cttatccctc tcttcccctt cccttatata ttgaggctat ggggtaggag aaaagtgcac   5040
aacccaccac cccctctact cgtgcattaa aatttcttat ttaccctttt ccccccttccc   5100
```

```
atttcttccc actttcatct accttttctg gcaaaaagga gcctttttgct ctctgtgacc   5160
ctaagagcac actgcacagg gaaaattgcc ccatccagac ctggctccac tcttgatctc   5220
tcttgtcctc ttctgctctt ttcctggtgc tcttttttct cggtggggtg tgggtaatag   5280
aacagccgtg ggcttttggg gacctttaac tttttttttct ctcttttgtt tataaaaaac   5340
actaaacatt caattccaga gaacccaaaa tcccaccttc ccaccgaaca ctactaaggg   5400
gcttgtgttc tgctccatac cttttctctt ttctttctgt cttgttaatg cttttaaaaa   5460
caaatgagtt ttttatatataa ataaagtttt taaagtgtgt atgtgggggg tctgtgtcat   5520
ttcttcactt caagctgtta tttcttccct gctttgcatc tttgttactt ccttatgtat   5580
cagtgtcctt tccagagcaa ccagaaggag gttataccag gatttatttt gagctcagcc   5640
ccaactcttt atcaagcaac attcttgtta actatatgtg aaacattttt tcttctgaag   5700
attcttaaaa attgaatgtg gctgaagttg aacatgggag cttattgcta atttagagat   5760
aggaaactga agcataaaga attaatgact tactttaatt actggaattc ttctgcaaca   5820
tttgacaaaa ctaaccttga ataaggccca ctgtaatacg tagctctctt aaatataaca   5880
cttaggacta gaagattaga aactaccaat cccaactacg taataggaaa atgtaggatc   5940
aaaaggccca tgtatataag tactgaccac tgggccataa tgttgcttct caggctatat   6000
gcagtccttt agtcagaagt caataggcct atttattaat attttacaga ccatattacc   6060
tggattacca gggactatct ttgctgcaga gatcaagggt taagatctat gggaagatac   6120
ttatttttct gaggtcctta tgtcctgtca tataattaaa gactcaagag aatttatgtg   6180
aaatgctttc tgtatgcccc aatctttaga ttaaaattat atacctgctc ct           6232
```

<210> SEQ ID NO 14
<211> LENGTH: 1965
<212> TYPE: DNA
<213> ORGANISM: Homo sapiens

<400> SEQUENCE: 14

```
gtctggttct ctctctccag aaggttctgc cggttccccc agctctgggt acccggctct     60
gcatcgcgtc gccatgatgg gccatcgtcc agtgctcgtg ctcagccaga acacaaagcg    120
tgaatccgga agaaaagttc aatctggaaa catcaatgct gccaagacta ttgcagatat    180
catccgaaca tgtttgggac ccaagtccat gatgaagatg cttttggacc caatgggagg    240
cattgtgatg accaatgatg gcaatgccat tcttcgagag attcaagtcc agcatccagc    300
ggccaagtcc atgatcgaaa ttagccggac ccaggatgaa gaggttggag atgggaccac    360
atcagtaatt attcttgcag gggaaatgct gtctgtagct gagcacttcc tggagcagca    420
gatgcaccca acagtggtga tcagtgctta ccgcaaggca ttggatgata tgatcagcac    480
cctaaagaaa ataagtatcc cagtcgacat cagtgacagt gatatgatgc tgaacatcat    540
caacagctct attactacca aagccatcag tcggtggtca tctttggctt gcaacattgc    600
cctggatgct gtcaagatgg tacagtttga ggagaatggt cggaaagaga ttgacataaa    660
aaaatatgca agagtggaaa agatacctgg aggcatcatt gaagactcct gtgtcttgcg    720
tggagtcatg attaacaagg atgtgaccca tccacgtatg cggcgctata tcaagaaccc    780
tcgcattgtg ctgctggatt cttctctgga atacaagaaa ggagaaagcc agactgacat    840
tgagattaca cgagaggagg acttcacccg aattctccag atggaggaag agtacatcca    900
gcagctctgt gaggacatta tccaactgaa gcccgatgtg gtcatcactg aaaagggcat    960
ctcagattta gctcagcact accttatgcg ggccaatatc acagccatcc gcagagtccg   1020
```

```
gaagacagac aataatcgca ttgctagagc ctgtggggcc cggatagtca gccgaccaga   1080

ggaactgaga gaagatgatg ttggaacagg agcaggcctg ttggaaatca agaaaattgg   1140

agatgaatac tttactttca tcactgactg caaagacccc aaggcctgca ccattctcct   1200

ccggggggct agcaaagaga ttctctcgga agtagaacgc aacctccagg atgccatgca   1260

agtgtgtcgc aatgttctcc tggaccctca gctggtgcca gggggtgggg cctccgagat   1320

ggctgtggcc catgccttga cagaaaaatc caaggccatg actggtgtgg aacaatggcc   1380

atacagggct gttgcccagg ccctagaggt cattcctcgt accctgatcc agaactgtgg   1440

ggccagcacc atccgtctac ttacctccct tcgggccaag cacacccagg agaactgtga   1500

gacctggggt gtaaatggtg agacgggtac tttggtggac atgaaggaac tgggcatatg   1560

ggagccattg gctgtgaagc tgcagactta taagacagca gtggagacgg cagttctgct   1620

actgcgaatt gatgacatcg tttcaggcca caaaaagaaa ggcgatgacc agagccggca   1680

aggcggggct cctgatgctg gccaggagtg agtgctaggc aaggctactt caatgcacag   1740

aaccagcaga gtctcccctt ttcctgagcc agagtgccag gaacactgtg gacgtctttg   1800

ttcagaaggg atcaggttgg ggggcagccc ccagtccctt tctgtcccag ctcagttttc   1860

caaaagacac tgacatgtaa ttcttctcta ttgtaaggtt tccatttagt ttgcttccga   1920

tgattaaatc taagtcattt gaaaaaaaaa aaaaaaaaaa aaaaa                   1965
```

<210> SEQ ID NO 15
<211> LENGTH: 3454
<212> TYPE: DNA
<213> ORGANISM: Homo sapiens

<400> SEQUENCE: 15

```
cgccaaagga aaagcccctt ggatgagagg caggcgcttc agagaagcta agaaaagcac     60

ctctccgcgc gccccacctc ctccgcctcg cgctcctcct gagcagcggg cccagactgc    120

gctccggccg cggccctcgc cccgcggagc cctcctaccc cggcccgacg ctcggcccgc    180

gacctgcccc gagccctctc catggaggca gcccgcccct ccggctcctg gaacggagcc    240

ctctgccggc tgctcctgct gaccctcgcg atcttaatat ttgccagtga tgcctgcaaa    300

aatgtgacat tacatgttcc ctccaaacta gatgccgaga aacttgttgg tagagttaac    360

ctgaaagagt gctttacagc tgcaaatcta attcattcaa gtgatcctga cttccaaatt    420

ttggaggatg gttcagtcta tacaacaaat actattctat tgtcctcgga gaagagaagt    480

tttaccatat tactttccaa cactgagaac caagaaaaga agaaaatatt tgtctttttg    540

gagcatcaaa caaaggtcct aaagaaaaga catactaaag aaaaagttct aaggcgcgcc    600

aagagaagat gggctccaat tccttgttcg atgctagaaa actccttggg tccttttcca    660

cttttccttc aacaggttca atctgacacg gcccaaaact ataccatata ctattccata    720

agaggtcctg gagttgacca agaacctcgg aatttatttt atgtggagag agacactgga    780

aacttgtatt gtactcgtcc tgtagatcgt gagcagtatg aatcttttga gataattgcc    840

tttgcaacaa ctccagatgg gtatactcca gaacttccac tgcccctaat aatcaaaata    900

gaggatgaaa atgataacta cccaattttt acagaagaaa cttatacttt tacaattttt    960

gaaaattgca gagtgggcac tactgtggga caagtgtgtg ctactgacaa agatgagcct   1020

gacacgatgc acacacgcct gaagtactcc atcattgggc aggtgccacc atcacccacc   1080

ctattttcta tgcatccaac tacaggcgtg atcaccacaa catcatctca gctagacaga   1140

gagttaattg acaagtacca gttgaaaata aaagtacaag acatggatgg tcagtatttt   1200
```

```
ggtctacaga caacttcaac ttgtatcatt aacattgatg atgtaaatga ccacttgcca   1260
acatttactc gtacttctta tgtgacatca gtggaagaaa atacagttga tgtggaaatc   1320
ttacgagtta ctgttgagga taaggactta gtgaatactg ctaactggag agctaattat   1380
accattttaa agggcaatga aaatggcaat tttaaaattg taacagatgc caaaaccaat   1440
gaaggagttc tttgtgtagt taagcctttg aattatgaag aaaagcaaca gatgatcttg   1500
caaattggtg tagttaatga agctccattt tccagagagg ctagtccaag atcagccatg   1560
agcacagcaa cagttactgt taatgtagaa gatcaggatg agggccctga gtgtaaccct   1620
ccaatacaga ctgttcgcat gaaagaaaat gcagaagtgg gaacaacaag caatggatat   1680
aaagcatatg acccagaaac aagaagtagc agtggcataa ggtataagaa attaactgat   1740
ccaacagggt gggtcaccat tgatgaaaat acaggatcaa tcaaagtttt cagaagcctg   1800
gatagagagg cagagaccat caaaaatggc atatataata ttacagtcct tgcatcagac   1860
caaggaggga gaacatgtac ggggacactg ggcattatac ttcaagacgt gaatgataac   1920
agcccattca tacctaaaaa gacagtgatc atctgcaaac ccaccatgtc atctgcggag   1980
attgttgcgg ttgatcctga tgagcctatc catggcccac cctttgactt tagtctggag   2040
agttctactt cagaagtaca gagaatgtgg agactgaaag caattaatga tacagcagca   2100
cgtctttcct atcagaatga tcctccattt ggctcatatg tagtacctat aacagtgaga   2160
gatagacttg gcatgtctag tgtcacttca ttggatgtta cactgtgtga ctgcattacc   2220
gaaaatgact gcacacatcg tgtagatcca aggattggcg gtggaggagt acaacttgga   2280
aagtgggcca tccttgcaat attgttgggc atagcattgc tcttttgcat cctgtttacg   2340
ctggtctgtg ggcttctggg gacgtctaaa caaccaaaag taattcctga tgatttagcc   2400
cagcagaacc taattgtatc aaacacagaa gctcctggag atgacaaagt gtattctgcg   2460
aatggcttca caacccaaac tgtgggcgct tctgctcagg gagtttgtgg caccgtggga   2520
tcaggaatca aaaacggagg tcaggagacc atcgaaatgg tgaaaggagg acaccagacc   2580
tcggaatcct gccgggggc tggccaccat cacaccctgg actcctgcag gggaggacac   2640
acggaggtgg acaactgcag atacacttac tcggagtggc acagttttac tcagccccgt   2700
cttggtgaaa aagtgtatct gtgtaatcaa gatgaaaatc acaagcatgc ccaagactat   2760
gtcctgacat ataactatga aggaagagga tcggtggctg ggtctgtagg ttgttgcagt   2820
gaacgacaag aagaagatgg gcttgaattt ttggataatt tggagcccaa atttaggaca   2880
ctagcagaag catgcatgaa gagatgagtg tgttctaata agtctctgaa agccagtggc   2940
tttatgactt ttaaaaaaaa ttacaaacca agaatttttt aaagcagaag atgctatttg   3000
tgggggtttt tctctcatta tttggatgga atctctttgg tcaaatgcac atttacagag   3060
agacactata aacaagtaca caaatttttc aatttttaca tatttttaaa ttacttatct   3120
tctatccaag gaggtctaca gagaaattaa agtctgcctt atttgttaca tttgggtata   3180
atgacaacag ccaatttata gtgcaataaa atgtaattaa ttcaagtcct tattatagac   3240
tatttgaagc acaacctaat ggaaaattgt agagaccttg ctttaacatt atctccagtt   3300
aattaagtgt tcatgtggtg cttggaaact gttgttttcc tgaacatcta aagtgtgtag   3360
actgcattct tgctattatt ttattcttgt aatgtgacct tttcactgtg caaagggaga   3420
tttctagcca ggcattgact attacaattt catt                               3454
```

<210> SEQ ID NO 16
<211> LENGTH: 619
<212> TYPE: DNA

<213> ORGANISM: Homo sapiens

<400> SEQUENCE: 16

```
agcagttcta agggaccata cagagtattc ctctcttcac accaggacca gccactgttg     60
cagcatgagt tcccagcagc agaagcagcc ctgcatccca cccccctcagc ttcagcagca   120
gcaggtgaaa cagccttgcc agcctccacc tcaggaacca tgcatcccca aaaccaagga    180
gccctgccac cccaaggtgc ctgagccctg ccaccccaaa gtgcctgagc cctgccagcc    240
caagcttcca gagccatgcc accccaaggt gcctgagccc tgcccttcaa tagtcactcc    300
agcaccagcc cagcagaaga ccaagcagaa gtaatgtggt ccacagccat gcccttgagg    360
agccggccac cagatgctga atcccctatc ccattctgtg tatgagtccc atttgccttg    420
caattagcat tctgtctccc ccaaaaaaga atgtgctatg aagctttctt tcctacacac    480
tctgagtctc tgaatgaagc tgaaggtctt agtaccagag ctagttttca gctgctcaga    540
attcatctga agagagactt aagatgaaag caaatgattc agctccctta tacccccatt    600
aaattcactt tcaattcca                                                  619
```

<210> SEQ ID NO 17
<211> LENGTH: 3528
<212> TYPE: DNA
<213> ORGANISM: Homo sapiens

<400> SEQUENCE: 17

```
agccaaggac tctggagccg ccgccgccgc tgctgcggtt catatccgga gtagacggag     60
ccgcagtaga cggatccgcg gctgcaccaa accactgccc ctcggagcct ggtagtgggc    120
cacaagcccc cagtcccaga ggcgtggtgg gtcgggcaga gtcggaagaa ctggctttct    180
agctggaaga tgcggaaggg gagcgactag gccgcttgcg tctgggcctg gcagaaggga    240
ccggattttc tggcatcctt aaatcttgtg tcaaggattg gttataatat aaccagaaac    300
catgacggcg gctgagaacg tatgctacac gttaattaac gtgccaatgg attcagaacc    360
accatctgaa attagcttaa aaaatgatct agaaaaagga gatgtaaagt caaagactga    420
agctttgaag aaagtaatca ttatgattct gaatggtgaa aaacttcctg gacttctgat    480
gaccatcatt cgttttgtgc tacctcttca ggatcacact atcaagaaat tacttctggt    540
attttgggaa attgttccta aaacaactcc agatgggaga cttttacatg agatgatcct    600
tgtatgtgat gcatacagaa aggatcttca acatcctaat gaatttattc gaggatctac    660
tcttcgtttt ctttgcaaat tgaaagaagc agaattgcta gaacctttaa tgccagctat    720
tcgtgcatgt ttggagcatc gacacagcta tgttagaaga aatgctgttt tggccatcta    780
taccatctat agaaattttg aacatcttat acctgatgct cctgaactga tacatgattt    840
tctggtgaat gagaaggatg caagttgcaa aaggaatgca tttatgatgc taattcatgc    900
agatcaggat cgagctttgg attacttaag tacttgcatt gatcaagttc aaacatttgg    960
agacattctg cagctggtta ttgttgaact gatttataag gtctgtcatg ctaatccatc   1020
agaaagagct cgttttattc gctgcatcta taacttatta cagtcatcca gccctgctgt   1080
aaaatatgaa gctgctggga cattagtgac actctctagt gcaccaactg caatcaaggc   1140
tgctgctcag tgttacattg atttaattat taaggagagc gacaacaatg taaaactcat   1200
agttttggat cgcttgatag aattaaaaga gcatcctgct catgaacgag tactacagga   1260
tctggttatg gatatcctaa gagtattgag cacaccagac ttagaagtac gaaagaaaac   1320
tctgcagtta gcactggatc ttgtctcttc tagaaatgtt gaagagctgg ttattgtcct   1380
```

```
gaagaaggaa gtgataaaaa caaataatgt gtctgagcat gaagatactg acaaatacag   1440

acaactccta gtgcgaacat tgcattcctg ttctgtccga tttccagata tggctgcaaa   1500

tgttattcct gtgttaatgg aatttctcag tgacaacaac gaagcagcag ctgctgatgt   1560

cttggagttt gttcgtgaag ccattcagcg ctttgataac ctgagaatgc ttattgttga   1620

gaagatgctt gaagtctttc atgctattaa atctgtcaag atttaccgag gagcattatg   1680

gatcctggga gaatactgta gtaccaagga agacattcag agtgtgatga ctgagatccg   1740

caggtccctt ggagagatcc caattgtaga gtcagaaata aagaaagaag ctggtgaatt   1800

aaaacctgaa gaagaaataa ctgtagggcc agttcagaaa ttggttactg aaatgggtac   1860

ctatgcaact cagagtgccc ttagcagttc tagacccacc aagaaagagg aagacagacc   1920

tcccttgaga ggattccttc tggatggaga tttctttgtt gctgcctccc ttgccacaac   1980

tctgaccaag attgcattgc gctatgtagc tttggttcag gagaagaaaa agcaaaattc   2040

ttttgttgct gaggctatgt tgctcatggc tactatcctg catttgggaa aatcctctct   2100

tcctaagaag ccaattactg atgatgatgt ggatcgaatt tccctgtgcc tcaaggtctt   2160

gtctgaatgt tcacctttaa tgaatgacat tttcaataag gaatgcagac agtccctttc   2220

tcacatgtta tctgctaaac tagaagaaga gaaattatcc caaaagaaag aatctgaaaa   2280

gaggaatgtg acagtacagc ctgatgaccc catttccttc atgcaactaa ctgctaagaa   2340

tgaaatgaac tgcaaggaag atcagtttca gctgagttta ctggcagcaa tgggtaacac   2400

acagaggaaa gaggcagcag atcccctagc atctaaactt aacaaggtca cccaattgac   2460

aggtttctca gatcctgtat atgcagaagc ttacgttcat gtcaaccaat atgatattgt   2520

cctggatgta cttgttgtga accaaaccag tgatactttg cagaattgca cattagaact   2580

agctacacta ggggatctga aacttgtgga aaagccgtct cctttgactc ttgctcctca   2640

tgacttcgca aatattaaag ctaacgtcaa agtagcatca acagaaaatg gaataatttt   2700

tggtaatata gtttatgatg tctctggagc agcaagtgac agaaattgtg tggttctcag   2760

tgatattcac atcgacatca tggactatat ccagcctgca acttgcactg atgcagaatt   2820

ccgtcagatg tgggccgaat ttgaatggga aaacaaagtg acagttaaca ccaacatggt   2880

tgatttaaat gactacttac agcacatatt aaagtcaacc aatatgaaat gcctgactcc   2940

agaaaaggcc ctttctggtt actgtggctt tatggcagcc aacctttatg ctcgttccat   3000

atttggtgaa gatgcacttg caaatgtcag cattgagaag ccaattcacc agggaccaga   3060

tgctgctgtt accggccata taagaattcg tgcaaagagc cagggaatgg ccttaagtct   3120

tggagataaa atcaacttgt cacagaagaa aactagtata taaaaataaa caaaaagtcc   3180

ttgaagcttt acagttaatt taggtatggg cttactggac tccaacatct tttgtactct   3240

ttcatgctta tatagaatct gagttcatgc tgaatacttt tcagccaata atttatagcc   3300

tttcccttaa atcaagattg agtttaaaat tatagtttgt cttttgtctt aacagttctg   3360

aatgctgtcc tcaaagtata taatgtttca tgtaccaaga cccttttcac agtacaataa   3420

acagatctat tcataaattt ttgttatttt ataaataaat gattacataa ttttagttat   3480

aaaaaaaaaa aaaaaaaaaa agaaaaaaaa aaaaaaaaaa aaaaaaaa                3528
```

<210> SEQ ID NO 18
<211> LENGTH: 1447
<212> TYPE: DNA
<213> ORGANISM: Homo sapiens

<400> SEQUENCE: 18

```
tgtcactgag ggttgactga ctggagagct caagtgcagc aaagagaagt gtcagagcat      60
gagcgccaag tccagaacca tagggattat tggagctcct ttctcaaagg gacagccacg     120
aggaggggtg gaagaaggcc ctacagtatt gagaaaggct ggtctgcttg agaaacttaa     180
agaacaagag tgtgatgtga aggattatgg ggacctgccc tttgctgaca tccctaatga     240
cagtcccttt caaattgtga agaatccaag gtctgtggga aaagcaagcg agcagctggc     300
tggcaaggtg gcagaagtca agaagaacgg aagaatcagc ctggtgctgg gcggagacca     360
cagtttggca attggaagca tctctggcca tgccagggtc caccctgatc ttggagtcat     420
ctgggtggat gctcacactg atatcaacac tccactgaca accacaagtg gaaacttgca     480
tggacaacct gtatctttcc tcctgaagga actaaaagga aagattcccg atgtgccagg     540
attctcctgg gtgactccct gtatatctgc caaggatatt gtgtatattg gcttgagaga     600
cgtggaccct ggggaacact acattttgaa aactctaggc attaaatact tttcaatgac     660
tgaagtggac agactaggaa ttggcaaggt gatggaagaa acactcagct atctactagg     720
aagaaagaaa aggccaattc atctaagttt tgatgttgac ggactggacc catctttcac     780
accagctact ggcacaccag tcgtgggagg tctgacatac agagaaggtc tctacatcac     840
agaagaaatc tacaaaacag ggctactctc aggattagat ataatggaag tgaacccatc     900
cctggggaag acaccagaag aagtaactcg aacagtgaac acagcagttg caataacctt     960
ggcttgtttc ggacttgctc gggagggtaa tcacaagcct attgactacc ttaacccacc    1020
taagtaaatg tggaaacatc cgatataaat ctcatagtta atggcataat tagaaagcta    1080
atcattttct taagcataga gttatccttc taaagacttg ttctttcaga aaaatgtttt    1140
tccaattagt ataaactcta caaattccct cttggtgtaa aattcaagat gtggaaattc    1200
taactttttt gaaatttaaa agcttatatt ttctaacttg gcaaaagact tatccttaga    1260
aagagaagtg tacattgatt tccaattaaa aatttgctgg cattaaaaat aagcacactt    1320
acataagccc ccatacatag agtgggactc ttggaatcag gagacaaagc taccacatgt    1380
ggaaaggtac tatgtgtcca tgtcattcaa aaaatgtgat tttttataat aaactcttta    1440
taacaag                                                               1447
```

<210> SEQ ID NO 19
<211> LENGTH: 3916
<212> TYPE: DNA
<213> ORGANISM: Homo sapiens

<400> SEQUENCE: 19

```
gcttggggcc gccatcttgg caagaggcga agcggcagcg gttcctgtca agggggcagc      60
aggtccagag ctgctggtgc tcccgttccc cagaccctac ccctatcccc agtggagccg     120
gagtgcgggc gcgccccacc accgccctca ccatggtgct gttggcagca gcggtctgca     180
caaaagcagg aaaggctatt gtttctcgac agtttgtgga aatgacccga actcggattg     240
agggcttatt agcagctttt ccaaagctca tgaacactgg aaaacaacat acgtttgttg     300
aaacagagag tgtaagatat gtctaccagc ctatggagaa actgtatatg gtactgatca     360
ctaccaaaaa cagcaacatt ttagaagatt tggagaccct aaggctcttc tcaagagtga     420
tccctgaata ttgccgagcc ttagaagaga atgaaatatc tgagcactgt tttgatttga     480
tttttgcttt tgatgaaatt gtcgcactgg gataccggga gaatgttaac ttggcacaga     540
tcagaacctt cacagaaatg gattctcatg aggagaaggt gttcagagcc gtcagagaga     600
ctcaagaacg tgaagctaag gctgagatgc gtcgtaaagc aaaggaatta caacaggccc     660
```

```
gaagagatgc agagagacag ggcaaaaaag caccaggatt tggcggattt ggcagctctg    720
cagtatctgg aggcagcaca gctgccatga tcacagagac catcattgaa actgataaac    780
caaaagtggc acctgcacca gccaggcctt caggccccag caaggcttta aaacttggag    840
ccaaaggaaa ggaagtagat aactttgtgg acaaattaaa atctgaaggt gaaaccatca    900
tgtcctctag tatgggcaag cgtacttctg aagcaaccaa aatgcatgct ccacccatta    960
atatggaaag tgtacatatg aagattgaag aaaagataac attaacctgt ggacgagacg   1020
gaggattaca gaatatggag ttgcatggca tgatcatgct taggatctca gatgacaagt   1080
atggccgaat tcgtcttcat gtggaaaatg aagataagaa aggggtgcag ctacagaccc   1140
atccaaatgt ggataaaaaa cttttcactg cagagtctct aattggcctg aagaatccag   1200
agaagtcatt tccagtcaac agtgacgtag gggtgctaaa gtggagacta caaaccacag   1260
aggaatcttt tattccactg acaattaatt gctggccctc ggagagtgga aatggctgtg   1320
atgtcaacat agaatatgag ctacaagaag ataatttaga actgaatgat gtggttatca   1380
ccatcccact cccgtctggt gtcggcgcgc ctgttatcgg tgagatcgat ggggagtatc   1440
gacatgacag tcgacgaaat accctggagt ggtgcctgcc tgtgattgat gccaaaaata   1500
agagtggcag cctggagttt agcattgctg gcagcccaa tgacttcttc cctgttcaag    1560
tttcctttgt ctccaagaaa aattactgta acatacaggt taccaaagtg acccaggtag   1620
atggaaacag ccccgtcagg ttttccacag agaccacttt cctagtggat aagtatgaaa   1680
ttctgtaata ccaagaagag ggagctgaaa aggaaaattt tcagattaat aaagaagacg   1740
ccaatgatgg ctgaagagtt tttcccagat ttacaagcca ctggagaccc ctttttttctg   1800
atacaatgca cgattctctg cgcgcaagga ccctcgactc acccccatgt ttcagtgtca   1860
cagagacatt ctttgataag gaaatggcac aaacataaag ggaaaggctg ctaattttct   1920
ttggcagatt gtattggcca gcaggaaagc aagctctcca gagaatgccc ccagttaaat   1980
acctcctcta cctttaccta agttgctcct ttatttttat tttattatta ttattattat   2040
tattattttt tgagatggag tctcactttg taacccaggc tggaatgcaa tggcatgatc   2100
tcagctcact gcaacctccg cctcctgggt tcaagcaagt ctcctgcctc agcctccgag   2160
tagctgggac tacaggtgca cgccaccacg cctggctaat tttttgtatt ttagtagaga   2220
cggggtttca ccgtgttgcc caggctggtc gcgaactcct gagctcaggc aatccgccca   2280
cctcagcctc ccaaagtgtt gggattacag gcatgagcca ccatgcccag ctgctccttt   2340
attttaatcc ctaaatataa tccctaaata tagttatatt tcatacttag tttgttttta   2400
aaaagttttc tctgtagaaa attttaatca ttcataccct ttacctttag gtttttcttt   2460
ctatacattc agtcaggcac tggatcatc tgtttacagg cattatattt atttggcact    2520
cctggaacaa gtatatctaa cccattcttg atttttggac tattcaggtg aactatttga   2580
ggggtatggg gtctagaagt taaaagatac gcatgtcttc tgttcttttc ccgtatcaat   2640
tcattccttc atctctttgc caagttgttt tcctttcagg gcctgtcctt ccagtttaga   2700
acagtaccat gaatcccact tgtgtcaata ttaaagatag ctgagaagca cctttcaaat   2760
ggcacagtcc ctcttcaaga tgtctaaaag aatggttatg tctgtccagt tagggatttc   2820
acatccacat gtaatcatgt ctgctgctgt tgctacccaa attttcattt ctccacattt   2880
tgggtactta agctaaaacg taatggccac agtctgtaat ccattcacat tcctcagttt   2940
caccacctcc ctcttccaga ctgcactctc tgtcatcagt cccctccttt ctaacagaaa   3000
tggggttatg attttgaagg ctgtgggttc agggagtctt tgccaatcct gttggcccta   3060
```

```
aactatcaag gaggctccat ttcaccattt gatttttttgc atttcaggag gcaactgatt   3120

gtttcgatat gtacatatta ctcacgtata ccccatttcc ttccagtcag cccaacattt   3180

tccaccagtc tgtccccatc tctgaaatcc ttccttctct ttccccctaa gtcttttgag   3240

tgtcatcatg tactggtggt ttctcggttc catctcatcc atttcctttt caatggagac   3300

tacagcgtca gccagctcag ccttggcttt taactcaata ttccagtcca taggggtggt   3360

taaaagttgc tgcaaggctg caggcactgg cagtgggaag aggcagacga ctagatgact   3420

tctgcacttt tagctggttg aaaagtacca ctcccactct gaacatctgg ccgtccctgc   3480

aaagagtgta ctgtgcttga agcagagcac tcacacataa atggctgtgt gtggaattgc   3540

ttgccaaaga agtttctagc ctttcccttt cccctaactg catcagggaa gaattcttat   3600

ctctagcttg gtttccacat gaggtttttc tgagaagggc ttgggacaag aagtctgtca   3660

tgttagttaa gcaggcaaga aatcctacta atccagtttt gtttgaaagt tgtttgtccg   3720

tatgattttt taaaagtcaa gtttaatttc aaaaaaactt ttttttctga gattactttt   3780

ggggtaatat ttaaaatgag agacattttg taaccctgta aaatacatag ggaatataac   3840

attccagtgt atacaaagaa ggcaaattct ttaatcaaat aaagcgtatt ataaaatgag   3900

aaaaaaaaaa aaaaaa                                                    3916
```

<210> SEQ ID NO 20
<211> LENGTH: 2280
<212> TYPE: DNA
<213> ORGANISM: Homo sapiens

<400> SEQUENCE: 20

```
tccagccaga aggatggggt ggctcccact cctgctgctt ctgactcaat gcttaggggt     60

ccctgggcag cgctcgccat tgaatgactt ccaagtgctc cggggcacag agctacagca    120

cctgctacat gcggtggtgc ccgggccttg gcaggaggat gtggcagatg ctgaagagtg    180

tgctggtcgc tgtgggccct taatggactg ccgggccttc cactacaacg tgagcagcca    240

tggttgccaa ctgctgccat ggactcaaca ctcgccccac acgaggctgc ggcgttctgg    300

gcgctgtgac ctcttccaga agaaagacta cgtacggacc tgcatcatga acaatggggt    360

tgggtaccgg ggcaccatgg ccacgaccgt gggtggcctg ccctgccagg cttggagcca    420

caagttcccg aatgatcaca agtacacgcc cactctccgg aatggcctgg aagagaactt    480

ctgccgtaac cctgatggcg accccggagg tccttggtgc tacacaacag accctgctgt    540

gcgcttccag agctgcggca tcaaatcctg ccgggaggcc gcgtgtgtct ggtgcaatgg    600

cgaggaatac cgcggcgcgg tagaccgcac ggagtcaggg cgcgagtgcc agcgctggga    660

tcttcagcac ccgcaccagc acccccttcga gccgggcaag ttcctcgacc aaggtctgga    720

cgacaactat tgccggaatc ctgacggctc cgagcggcca tggtgctaca ctacggatcc    780

gcagatcgag cgagagttct gtgacctccc ccgctgcggg tccgaggcac agccccgcca    840

agaggccaca actgtcagct gcttccgcgg gaagggtgag ggctaccggg gcacagccaa    900

taccaccact gcgggcgtac cttgccagcg ttgggacgcg caaatccctc atcagcaccg    960

atttacgcca gaaaaatacg cgtgcaaaga ccttcgggag aacttctgcc ggaaccccga   1020

cggctcagag gcgccctggt gcttcacact gcggcccggc atgcgcgcgg ccttttgcta   1080

ccagatccgg cgttgtacag acgacgtgcg gccccaggac tgctaccacg gcgcagggga   1140

gcagtaccgc ggcacggtca gcaagacccg caagggtgtc cagtgccagc gctggtccgc   1200

tgagacgccg cacaagccgc agttcacgtt tacctccgaa ccgcatgcac aactggagga   1260
```

```
gaacttctgc cggaacccag atggggatag ccatgggccc tggtgctaca cgatggaccc   1320

aaggacccca ttcgactact gtgccctgcg acgctgcgct gatgaccagc cgccatcaat   1380

cctggacccc ccagaccagg tgcagtttga gaagtgtggc aagagggtgg atcggctgga   1440

tcagcggcgt tccaagctgc gcgtggttgg gggccatccg ggcaactcac cctggacagt   1500

cagcttgcgg aatcggcagg gccagcattt ctgcgggggg tctctagtga aggagcagtg   1560

gatactgact gcccggcagt gcttctcctc ctgccatatg cctctcacgg gctatgaggt   1620

atggttgggc accctgttcc agaacccaca gcatggagag ccaagcctac agcgggtccc   1680

agtagccaag atggtgtgtg ggccctcagg ctcccagctt gtcctgctca agctggagag   1740

atctgtgacc ctgaaccagc gtgtggccct gatctgcctg ccccctgaat ggtatgtggt   1800

gcctccaggg accaagtgtg agattgcagg ctggggtgag accaaaggta cgggtaatga   1860

cacagtccta aatgtggcct tgctgaatgt catctctaac caggagtgta acatcaagca   1920

ccgaggacgt gtgcgggaga gtgagatgtg cactgaggga ctgttggccc ctgtgggggc   1980

ctgtgagggt gactacgggg gcccacttgc ctgctttacc cacaactgct gggtcctgga   2040

aggaattata atccccaacc gagtatgcgc aaggtcccgc tggccagctg tcttcacgcg   2100

tgtctctgtg tttgtggact ggattcacaa ggtcatgaga ctgggttagg cccagccttg   2160

atgccatatg ccttggggag gacaaaactt cttgtcagac ataaagccat gtttcctctt   2220

taaaaaaaaa aaaaaaaaaa aaaaaaaaaa aaataaaaaa aaaaaaaaaa aaaaaaaaaa   2280
```

```
<210> SEQ ID NO 21
<211> LENGTH: 2876
<212> TYPE: DNA
<213> ORGANISM: Homo sapiens

<400> SEQUENCE: 21

gaattcctgc agctcagcag ccgccgccag agcaggacga accgccaatc gcaaggcacc     60

tctgagaact tcaggatgca gatgtctcca gccctcacct gcctagtcct gggcctggcc    120

cttgtctttg gtgaagggtc tgctgtgcac catcccccat cctacgtggc ccacctggcc    180

tcagacttcg gggtgagggt gtttcagcag gtggcgcagg cctccaagga ccgcaacgtg    240

gttttctcac cctatggggt ggcctcggtg ttggccatgc tccagctgac aacaggagga    300

gaaacccagc agcagattca agcagctatg ggattcaaga ttgatgacaa gggcatggcc    360

cccgccctcc ggcatctgta caaggagctc atggggccat ggaacaagga tgagatcagc    420

accacagacg cgatcttcgt ccagcgggat ctgaagctgg tccagggctt catgccccac    480

ttcttcaggc tgttccggag cacggtcaag caagtggact tttcagaggt ggagagagcc    540

agattcatca tcaatgactg ggtgaagaca cacacaaaag gtatgatcag caacttgctt    600

gggaaaggag ccgtggacca gctgacacgg ctggtgctgg tgaatgccct ctacttcaac    660

ggccagtgga agactccctt ccccgactcc agcacccacc gccgcctctt ccacaaatca    720

gacggcagca ctgtctctgt gcccatgatg gctcagacca acaagttcaa ctatactgag    780

ttcaccacgc ccgatggcca ttactacgac atcctggaac tgccctacca cggggacacc    840

ctcagcatgt tcattgctgc cccttatgaa aaagaggtgc ctctctctgc cctcaccaac    900

attctgagtg cccagctcat cagccactgg aaaggcaaca tgaccaggct gccccgcctc    960

ctggttctgc ccaagttctc cctggagact gaagtcgacc tcaggaagcc cctagagaac   1020

ctgggaatga ccgacatgtt cagacagttt caggctgact tcacgagtct ttcagaccaa   1080

gagcctctcc acgtcgcgca ggcgctgcag aaagtgaaga tcgaggtgaa cgagagtggc   1140
```

```
acggtggcct cctcatccac agctgtcata gtctcagccc gcatggcccc cgaggagatc   1200

atcatggaca gacccttcct ctttgtggtc cggcacaacc ccacaggaac agtccttttc   1260

atgggccaag tgatggaacc ctgaccctgg ggaaagacgc cttcatctgg gacaaaactg   1320

gagatgcatc gggaaagaag aaactccgaa gaaaagaatt ttagtgttaa tgactctttc   1380

tgaaggaaga gaagacattt gccttttgtt aaaagatggt aaaccagatc tgtctccaag   1440

accttggcct ctccttggag gacctttagg tcaaactccc tagtctccac ctgagaccct   1500

gggagagaag tttgaagcac aactccctta aggtctccaa accagacggt gacgcctgcg   1560

ggaccatctg ggcacctgc ttccacccgt ctctctgccc actcgggtct gcagacctgg   1620

ttcccactga ggccctttgc aggatggaac tacggggctt acaggagctt ttgtgtgcct   1680

ggtagaaact atttctgttc cagtcacatt gccatcactc ttgtactgcc tgccaccgcg   1740

gaggaggctg gtgacaggcc aaaggccagt ggaagaaaca ccctttcatc tcagagtcca   1800

ctgtggcact ggccacccct ccccagtaca ggggtgctgc aggtggcaga gtgaatgtcc   1860

cccatcatgt ggcccaactc tcctggcctg gccatctccc tccccagaaa cagtgtgcat   1920

gggttatttt ggagtgtagg tgacttgttt actcattgaa gcagatttct gcttcctttt   1980

atttttatag gaatagagga agaaatgtca gatgcgtgcc cagctcttca ccccccaatc   2040

tcttggtggg gaggggtgta cctaaatatt tatcatatcc ttgcccttga gtgcttgtta   2100

gagagaaaga gaactactaa ggaaaataat attatttaaa ctcgctccta gtgtttcttt   2160

gtggtctgtg tcaccgtatc tcaggaagtc cagccacttg actggcacac accccctccgg   2220

acatccagcg tgacggagcc cacactgcca ccttgtggcc gcctgagacc ctcgcgcccc   2280

ccgcgccccc cgcgcccctc tttttcccct tgatggaaat tgaccataca atttcatcct   2340

ccttcagggg atcaaaagga cggagtgggg ggacagagac tcagatgagg acagagtggt   2400

ttccaatgtg ttcaatagat ttaggagcag aaatgcaagg ggctgcatga cctaccagga   2460

cagaactttc cccaattaca gggtgactca cagccgcatt ggtgactcac ttcaatgtgt   2520

catttccggc tgctgtgtgt gagcagtgga cacgtgaggg gggggtgggt gagagagaca   2580

ggcagctcgg attcaactac cttagataat atttctgaaa acctaccagc cagagggtag   2640

ggcacaaaga tggatgtaat gcactttggg aggccaaggc gggaggattg cttgagccca   2700

ggagttcaag accagcctgg gcaacatacc aagacccccg tctctttaaa aatatatata   2760

ttttaaatat acttaaatat atatttctaa tatctttaaa tatatatata tattttaaag   2820

accaatttat gggagaattg cacacagatg tgaaatgaat gtaatctaat agaagc        2876
```

```
<210> SEQ ID NO 22
<211> LENGTH: 1310
<212> TYPE: DNA
<213> ORGANISM: Homo sapiens

<400> SEQUENCE: 22

gctcggagcc cggagcgtgc ctcggcggcc tgtcggtttt caccatggag cagctgagct     60

cagcaaacac ccgcttcgcc ttggacctgt tcctggcgtt gagtgagaac aatccggctg    120

gaaacatctt catctctccc ttcagcattt catctgctat ggccatggtt tttctgggga    180

ccagaggtaa cacggcagca cagctgtcca agactttcca tttcaacacg gttgaagagg    240

ttcattcaag attccagagt ctgaatgctg atatcaacaa acgtggagcg tcttatattc    300

tgaaacttgc taatagatta tatggagaga aaacttacaa tttccttcct gagttcttgg    360

tttcgactca gaaaacatat ggtgctgacc tggccagtgt ggattttcag catgcctctg    420
```

```
aagatgcaag gaagaccata aaccagtggg tcaaaggaca gacagaagga aaaattccgg    480

aactgttggc ttcgggcatg gttgataaca tgaccaaact tgtgctagta aatgccatct    540

atttcaaggg aaactggaag gataaattca tgaaagaagc cacgacgaat gcaccattca    600

gattgaataa gaaagacaga aaaactgtga aaatgatgta tcagaagaaa aaatttgcat    660

atggctacat cgaggacctt aagtgccgtg tgctggaact gccttaccaa ggcgaggagc    720

tcagcatggt catcctgctg ccggatgaca ttgaggacga gtccacgggc ctgaagaaga    780

ttgaggaaca gttgactttg gaaaagttgc atgagtggac taaacctgag aatctcgatt    840

tcattgaagt taatgtcagc ttgcccaggt tcaaactgga agagagttac actctcaact    900

ccgacctcgc ccgcctaggt gtgcaggatc tctttaacag tagcaaggct gatctgtctg    960

gcatgtcagg agccagagat atttttatat caaaaattgt ccacaagtca tttgtggaag   1020

tgaatgaaga gggaacagag gcggcagctg ccacagcagg catcgcaact ttctgcatgt   1080

tgatgcccga agaaaatttc actgccgacc atccattcct tttctttatt cggcataatt   1140

cctcaggtag catcctattc ttggggagat ttcttcccc ttagaagaaa gagactgtag   1200

caatacaaaa atcaagctta gtgctttatt acctgagttt ttaatagagc caatatgtct   1260

tatatcttta ccaataaaac cactgtccag aaaaaaaaaa aaaaaaaaaa              1310


<210> SEQ ID NO 23
<211> LENGTH: 495
<212> TYPE: DNA
<213> ORGANISM: Homo sapiens
<220> FEATURE:
<221> NAME/KEY: misc_feature
<222> LOCATION: (488)..(488)
<223> OTHER INFORMATION: n is a, c, g, or t

<400> SEQUENCE: 23

tttgaatatt tatgtcaaat tacaaaccag tttaaagctg cctatttggc aaaatgatct     60

gctgcagaat tttcattttc tgtctctaga atgcagaaaa atgtcttaaa gttccttaat    120

ttgcttaatt taatgtggtt tccagaagat gtgaaaacct cctttatttt taaaatacct    180

gattccacat tggtcaatag tttcctcttt aatttacctc tctcctctca ctttatctat    240

aataagcagg gagaaatgaa gacacaccat caacacgttt gcttagatat gtcctcaact    300

aaatttctag tgtcacttac taattctaat ttcatccaat ataacataat taagataaat    360

tctataacaa gctacacata ctttccagtt ctaataccat gtttgtgatg gaaacaaagc    420

aggagtgccc tctgcaaggt gatcatctga gggtccaaga tgaaggggca cacaggtatt    480

ttatctgncc cacac                                                      495


<210> SEQ ID NO 24
<211> LENGTH: 488
<212> TYPE: DNA
<213> ORGANISM: Homo sapiens

<400> SEQUENCE: 24

ctgatatttt gtatattaat gaattatcca agattcgatg ggatttatca gtgtgtagat     60

agctctataa tgcttgaatt gtacacttct aagtgtgcag tgcaagagct tgtttatatt    120

tcatactttt tatactttga ggaaaaaaag tcaaagaaaa attgtatttg agggaaaaaa    180

ccatgaccaa gtaaaggata aattcaaaaa atagcctcat gagacttggc atacacactc    240

atgggattcc agttattatg gagtgcttcc atccctctcc accccttccc cccaaaaggt    300

tttctttgca agtgcttttg gaactaagag ctagtatctt ggattaactg atgcctgcta    360
```

```
gtgctttctg attactcgca ttctgtttct tgctttaaaa gaagagtaaa gacaagagtg    420

ttggaccagt attgcagttc tgtagtgtca tttcttataa aaaacaaaac aacaacaata    480

atttatca                                                              488
```

<210> SEQ ID NO 25
<211> LENGTH: 1396
<212> TYPE: DNA
<213> ORGANISM: Homo sapiens

<400> SEQUENCE: 25

```
tgactatcca gctctgagag acgggagttt ggagttgccc gctttacttt ggttgggttg     60

ggggggcgg cgggctgttt tgttcctttt cttttttaag agttgggttt tctttttaa    120

ttatccaaac agtgggcagc ttcctccccc acacccaagt atttgcacaa tatttgtgcg    180

gggtatgggg gtgggttttt aaatctcgtt tctcttggac aagcacaggg atctcgttct    240

cctcattttt tgggggtgtg tggggacttc tcaggtcgtg tccccagcct tctctgcagt    300

cccttctgcc ctgccgggcc cgtcgggagg cgccatggct cggatgaacc gcccggcccc    360

ggtggaggtg agctacaaac acatgcgctt cctcatcacc cacaacccca ccaacgccac    420

gctcagcacc ttcattgagg acctgaagaa gtacggggct accactgtgg tgcgtgtgtg    480

tgaagtgacc tatgacaaaa cgccgctgga gaaggatggc atcaccgttg tggactggcc    540

gtttgacgat ggggcgcccc cgcccggcaa ggtagtggaa gactggctga gcctggtgaa    600

ggccaagttc tgtgaggccc ccggcagctg cgtggctgtg cactgcgtgg cgggcctggg    660

ccgggctcca gtccttgtgg cgctggcgct tattgagagc gggatgaagt acgaggacgc    720

catccagttc atccgccaga agcgccgcgg agccatcaac agcaagcagc tcacctacct    780

ggagaaatac cggcccaaac agaggctgcg gttcaaagac ccacacacgc acaagacccg    840

gtgctgcgtt atgtagctca ggaccttggc tgggcctggt cgtcatgtag gtcaggacct    900

tggctggacc tggaggccct gcccagccct gctctgccca gcccagcagg ggctccaggc    960

cttggctggc cccacatcgc cttttcctcc ccgacacctc cgtgcacttg tgtccgagga   1020

gcgaggagcc cctcgggccc tgggtggcct ctgggccctt tctcctgtct ccgccactcc   1080

ctctggcggc gctggccgtg gctctgtctc tctgaggtgg gtcgggcgcc ctctgcccgc   1140

cccctcccac accagccagg ctggtctcct ctagcctgtt tgttgtgggg tgggggtata   1200

ttttgtaacc actgggcccc cagcccctct tttgcgaccc cttgtcctga cctgttctcg   1260

gcaccttaaa ttattagacc ccggggcagt caggtgctcc ggacacccga aggcaataaa   1320

acaggagccg tgaaaaaaaa aaaaaaaaaa aaaaaaaaaa aaaaaaaaaa aaaaaaaaaa   1380

aaaaaaaaaa aaaaaa                                                    1396
```

<210> SEQ ID NO 26
<211> LENGTH: 2294
<212> TYPE: DNA
<213> ORGANISM: Homo sapiens

<400> SEQUENCE: 26

```
aagcagttgt tttgctggaa ggagggagtg cgcgggctgc cccgggctcc tccctgccgc     60

ctcctctcag tggatggttc caggcaccct gtctggggca gggagggcac aggcctgcac    120

atcgaaggtg gggtgggacc aggctgcccc tcgccccagc atccaagtcc tcccttgggc    180

gcccgtggcc ctgcagactc tcagggctaa ggtcctctgt tgctttttgg ttccacctta    240

gaagaggctc cgcttgacta agagtagctt gaaggaggca ccatgcagga gctgcatctg    300
```

```
ctctggtggg cgcttctcct gggcctggct caggcctgcc ctgagccctg cgactgtggg    360

gaaaagtatg gcttccagat cgccgactgt gcctaccgcg acctagaatc cgtgccgcct    420

ggcttcccgg ccaatgtgac tacactgagc ctgtcagcca accggctgcc aggcttgccg    480

gagggtgcct tcagggaggt gcccctgctg cagtcgctgt ggctggcaca caatgagatc    540

cgcacggtgg ccgccggagc cctggcctct ctgagccatc tcaagagcct ggacctcagc    600

cacaatctca tctctgactt tgcctggagc gacctgcaca acctcagtgc cctccaattg    660

ctcaagatgg acagcaacga gctgaccttc atcccccgcg acgccttccg cagcctccgt    720

gctctgcgct cgctgcaact caaccacaac cgcttgcaca cattggccga gggcaccttc    780

accccgctca ccgcgctgtc ccacctgcag atcaacgaga acccccttcga ctgcacctgc    840

ggcatcgtgt ggctcaagac atgggccctg accacggccg tgtccatccc ggagcaggac    900

aacatcgcct gcacctcacc ccatgtgctc aagggtacgc cgctgagccg cctgccgcca    960

ctgccatgct cggcgccctc agtgcagctc agctaccaac ccagccagga tggtgccgag   1020

ctgcggcctg gttttgtgct ggcactgcac tgtgatgtgg acgggcagcc ggcccctcag   1080

cttcactggc acatccagat acccagtggc attgtggaga tcaccagccc caacgtgggc   1140

actgatgggc gtgccctgcc tggcacccct gtggccagct cccagccgcg cttccaggcc   1200

tttgccaatg gcagcctgct tatccccgac tttggcaagc tggaggaagg cacctacagc   1260

tgcctggcca ccaatgagct gggcagtgct gagagctcag tggacgtggc actggccacg   1320

cccggtgagg gtggtgagga cacactgggg cgcaggttcc atggcaaagc ggttgaggga   1380

aagggctgct atacggttga caacgaggtg cagccatcag ggccggagga caatgtggtc   1440

atcatctacc tcagccgtgc tgggaaccct gaggctgcag tcgcagaagg ggtccctggg   1500

cagctgcccc caggcctgct cctgctgggc caaagcctcc tcctcttctt cttcctcacc   1560

tccttctagc cccacccagg gcttccctaa ctcctcccct tgcccctacc aatgcccctt   1620

taagtgctgc aggggtctgg ggttggcaac tcctgaggcc tgcatgggtg acttcacatt   1680

ttcctacctc tccttctaat ctcttctaga gcacctgcta tccccaactt ctagacctgc   1740

tccaaactag tgactaggat agaatttgat cccctaactc actgtctgcg gtgctcattg   1800

ctgctaacag cattgcctgt gctctcctct caggggcagc atgctaacgg ggcgacgtcc   1860

taatccaact gggagaagcc tcagtggtgg aattccaggc actgtgactg tcaagctggc   1920

aagggccagg attgggggaa tggagctggg gcttagctgg gaggtggtct gaagcagaca   1980

gggaatggga gaggaggatg ggaagtagac agtggctggt atggctctga ggctccctgg   2040

ggcctgctca agctcctcct gctccttgct gttttctgat gatttggggg cttgggagtc   2100

cctttgtcct catctgagac tgaaatgtgg ggatccagga tggcttcctt cctcttaccc   2160

ttcctccctc agcctgcaac ctctatcctg gaacctgtcc tccctttctc cccaactatg   2220

catctgttgt ctgctcctct gcaaaggcca gccagcttgg gagcagcaga gaaataaaca   2280

gcatttctga tgcc                                                     2294
```

<210> SEQ ID NO 27
<211> LENGTH: 1399
<212> TYPE: DNA
<213> ORGANISM: Homo sapiens

<400> SEQUENCE: 27

```
agtgtgaaat cttcagagaa gaatttctct ttagttcttt gcaagaaggt agagataaag     60

acactttttc aaaaatggca atggtatcag aattcctcaa gcaggcctgg tttattgaaa    120
```

```
atgaagagca ggaatatgtt caaactgtga agtcatccaa aggtggtccc ggatcagcgg    180
tgagccccta tcctaccttc aatccatcct cggatgtcgc tgccttgcat aaggccataa    240
tggttaaagg tgtggatgaa gcaaccatca ttgacattct aactaagcga aacaatgcac    300
agcgtcaaca gatcaaagca gcatatctcc aggaaacagg aaagcccctg gatgaaacac    360
ttaagaaagc ccttacaggt caccttgagg aggttgtttt agctctgcta aaaactccag    420
cgcaatttga tgctgatgaa cttcgtgctg ccatgaaggg ccttggaact gatgaagata    480
ctctaattga gattttggca tcaagaacta acaaagaaat cagagacatt aacagggtct    540
acagagagga actgaagaga gatctggcca aagacataac ctcagacaca tctggagatt    600
ttcggaacgc tttgctttct cttgctaagg gtgaccgatc tgaggacttt ggtgtgaatg    660
aagacttggc tgattcagat gccagggcct tgtatgaagc aggagaaagg agaaagggga    720
cagacgtaaa cgtgttcaat accatcctta ccaccagaag ctatccacaa cttcgcagag    780
tgtttcagaa atacaccaag tacagtaagc atgacatgaa caaagttctg gacctggagt    840
tgaaaggtga cattgagaaa tgcctcacag ctatcgtgaa gtgcgccaca agcaaaccag    900
ctttctttgc agagaagctt catcaagcca tgaaaggtgt tggaactcgc cataaggcat    960
tgatcaggat tatggtttcc cgttctgaaa ttgacatgaa tgatatcaaa gcattctatc   1020
agaagatgta tggtatctcc ctttgccaag ccatcctgga tgaaaccaaa ggagattatg   1080
agaaaatcct ggtggctctt tgtggaggaa actaaacatt cccttgatgg tctcaagcta   1140
tgatcagaag actttaatta tatattttca tcctataagc ttaaatagga aagtttcttc   1200
aacaggatta cagtgtagct acctacatgc tgaaaaatat agcctttaaa tcatttttat   1260
attataactc tgtataatag agataagtcc atttttttaaa aatgttttcc ccaaaccata   1320
aaaccctata caagttgttc tagtaacaat acatgagaaa gatgtctatg tagctgaaaa   1380
taaaatgacg tcacaagac                                                1399
```

<210> SEQ ID NO 28
<211> LENGTH: 3088
<212> TYPE: DNA
<213> ORGANISM: Homo sapiens

<400> SEQUENCE: 28

```
acaaaaaagc ttttacgagg tatcagcact tttctttcat taggggggaag gcgtgaggaa     60
agtaccaaac agcagcggag ttttaaactt taaatagaca ggtctgagtg cctgaacttg    120
ccttttcatt ttacttcatc ctccaaggag ttcaatcact tggcgtgact tcactacttt    180
taagcaaaag agtggtgccc aggcaacatg ggtgactgga gcgccttagg caaactcctt    240
gacaaggttc aagcctactc aactgctgga gggaaggtgt ggctgtcagt acttttcatt    300
ttccgaatcc tgctgctggg gacagcggtt gagtcagcct ggggagatga gcagtctgcc    360
tttcgttgta acactcagca acctggttgt gaaaatgtct gctatgacaa gtctttccca    420
atctctcatg tgcgcttctg ggtcctgcag atcatatttg tgtctgtacc cacactcttg    480
tacctggctc atgtgttcta tgtgatgcga aaggaagaga aactgaacaa gaaagaggaa    540
gaactcaagg ttgcccaaac tgatggtgtc aatgtggaca tgcacttgaa gcagattgag    600
ataaagaagt tcaagtacgg tattgaagag catggtaagg tgaaaatgcg aggggggttg    660
ctgcgaacct acatcatcag tatcctcttc aagtctatct ttgaggtggc cttcttgctg    720
atccagtggt acatctatgg attcagcttg agtgctgttt acacttgcaa aagagatccc    780
tgcccacatc aggtggactg tttcctctct cgccccacgg agaaaaccat cttcatcatc    840
```

```
ttcatgctgg tggtgtcctt ggtgtccctg gccttgaata tcattgaact cttctatgtt     900
ttcttcaagg gcgttaagga tcgggttaag ggaaagagcg acccttacca tgcgaccagt     960
ggtgcgctga gccctgccaa agactgtggg tctcaaaaat atgcttattt caatggctgc    1020
tcctcaccaa ccgctcccct ctcgcctatg tctcctcctg ggtacaagct ggttactggc    1080
gacagaaaca attcttcttg ccgcaattac aacaagcaag caagtgagca aaactgggct    1140
aattacagtg cagaacaaaa tcgaatgggg caggcgggaa gcaccatctc taactcccat    1200
gcacagcctt ttgatttccc cgatgataac cagaattcta aaaaactagc tgctggacat    1260
gaattacagc cactagccat tgtggaccag cgaccttcaa gcagagccag cagtcgtgcc    1320
agcagcagac ctcggcctga tgacctggag atctagatac aggcttgaaa gcatcaagat    1380
tccactcaat tgtggagaag aaaaaaggtg ctgtagaaag tgcaccaggt gttaattttg    1440
atccggtgga ggtggtactc aacagcctta ttcatgaggc ttagaaaaca caaagacatt    1500
agaataccta ggttcactgg gggtgtatgg ggtagatggg tggagaggga ggggataaga    1560
gaggtgcatg ttggtattta aagtagtgga ttcaaagaac ttagattata aataagagtt    1620
ccattaggtg atacatagat aagggctttt tctccccgca aacaccccta agaatggttc    1680
tgtgtatgtg aatgagcggg tggtaattgt ggctaaatat ttttgtttta ccaagaaact    1740
gaaataattc tggccaggaa taaatacttc ctgaacatct taggtctttt caacaagaaa    1800
aagacagagg attgtcctta agtccctgct aaaacattcc attgttaaaa tttgcacttt    1860
gaaggtaagc tttctaggcc tgaccctcca ggtgtcaatg gacttgtgct actatatttt    1920
tttattcttg gtatcagttt aaaattcaga caaggcccac agaataagat tttccatgca    1980
tttgcaaata cgtatattct ttttccatcc acttgcacaa tatcattacc atcacttttt    2040
catcattcct cagctactac tcacattcat ttaatggttt ctgtaaacat ttttaagaca    2100
gttgggatgt cacttaacat tttttttttt tgagctaaag tcagggaatc aagccatgct    2160
taatatttaa caatcactta tatgtgtgtc gaagagtttg ttttgtttgt catgtattgg    2220
tacaagcaga tacagtataa actcacaaac acagatttga aaataatgca catatggtgt    2280
tcaaatttga acctttctca tggatttttg tggtgtgggc caatatggtg tttacattat    2340
ataattcctg ctgtggcaag taaagcacac ttttttttttc tcctaaaatg tttttccctg    2400
tgtatcctat tatggatact ggttttgtta attatgattc tttattttct ctccttttttt    2460
taggatatag cagtaatgct attactgaaa tgaatttcct ttttctgaaa tgtaatcatt    2520
gatgcttgaa tgatagaatt ttagtactgt aaacaggctt tagtcattaa tgtgagagac    2580
ttagaaaaaa tgcttagagt ggactattaa atgtgcctaa atgaattttg cagtaactgg    2640
tattcttggg ttttcctact taatacacag taattcagaa cttgtattct attatgagtt    2700
tagcagtctt ttggagtgac cagcaacttt gatgtttgca ctaagatttt atttggaatg    2760
caagagaggt tgaaagagga ttcagtagta cacatacaac taatttattt gaactatatg    2820
ttgaagacat ctaccagttt ctccaaatgc cttttttaaa actcatcaca gaagattggt    2880
gaaaatgctg agtatgacac ttttcttctt gcatgcatgt cagctacata aacagttttg    2940
tacaatgaaa attactaatt tgtttgacat tccatgttaa actacggtca tgttcagctt    3000
cattgcatgt aatgtagacc tagtccatca gatcatgtgt tctggagagt gttctttatt    3060
caataaagtt ttaatttagt ataaacat                                       3088
```

```
<210> SEQ ID NO 29
<211> LENGTH: 403
<212> TYPE: DNA
```

<213> ORGANISM: Homo sapiens

<400> SEQUENCE: 29

```
tttcattagt tatcattagt ttattataaa agagaaatat ggaaattatt tacatgacga     60
aagatttcag aacttcagtg gaatgggcag catcatgttg atgccatttc aatagtgact    120
tatttcagtc tacgtacttt ccaagaatgt caccatctct aaataggaaa taatccttgt    180
catctagaac tactttggtg cctccatatt ctgggagaag aactttatct ccaactttca    240
cgctaactgg ttgaatctct ccaccctttc ctttagaacc cgatccaaca gcgactactg    300
ttgcttgcaa tacttttcct tgagattttt ctggaagcat aatgcctcct ttggttacag    360
tttcagcagc actcctttca accaatactc ggtcaaagag tgg                      403
```

<210> SEQ ID NO 30
<211> LENGTH: 1023
<212> TYPE: DNA
<213> ORGANISM: Homo sapiens

<400> SEQUENCE: 30

```
gttggctgcc ggtgagttgg gtgccggtgg agtcgtgttg gtcctcagaa tccccgcgta     60
gccgctgcct cctcctaccc tcgccatgtt tcttacccgg tctgagtacg acaggggcgt    120
gaatactttt tctcccgaag gaagattatt tcaagtggaa tatgccattg aggctatcaa    180
gcttggttct acagccattg ggatccagac atcagagggt gtgtgcctag ctgtggagaa    240
gagaattact tccccactga tggagcccag cagcattgag aaaattgtag agattgatgc    300
tcacataggt tgtgccatga gtgggctaat tgctgatgct aagactttaa ttgataaagc    360
cagagtggag acacagaacc actggttcac ctacaatgag acaatgacag tggagagtgt    420
gacccaagct gtgtccaatc tggctttgca gtttggagaa gaagatgcag atccaggtgc    480
catgtctcgt ccctttggag tagcattatt atttggagga gttgatgaga aaggacccca    540
gctgtttcat atggacccat ctgggacctt tgtacagtgt gatgctcgag caattggctc    600
tgcttcagag ggtgcccaga gctccttgca agaagtttac cacaagtcta tgactttgaa    660
agaagccatc aagtcttcac tcatcatcct caaacaagta atggaggaga agctgaatgc    720
aacaaacatt gagctagcca cagtgcagcc tggccagaat ttccacatgt tcacaaagga    780
agaacttgaa gaggttatca aggacattta aggaatcctg atcctcagaa cttctctggg    840
acaatttcag ttctaataat gtccttaaat tttatttcca gctcctgttc cttggaaaat    900
ctccattgta tgtgcatttt ttaaatgatg tctgtacata aaggcagttc tgaaataaag    960
aaaatttaa aataaaaaaa aaaaaaaaaa aaaaaaaaaa aaaaaaaaaa aaaaaaaaaa   1020
aaa                                                                 1023
```

<210> SEQ ID NO 31
<211> LENGTH: 313
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:

```
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t

<400> SEQUENCE: 31

ntcttgggct caagcaancc tcctgccctg gcttcccaaa gtgttcagat tacaagtgtg     60

agccactgca cccagaccaa gaaattttaa ccctaactaa atacccaaaa aaagngtata    120

tatgttccac aaaggacatg ggtaagaatg tttatagcag cagtatttgt aatagccaga    180

aactggaaac aagccaaaca tctatctaca gcagaagaga ctattgttta tttatacaat    240

aaactacaat ataggcaata aaatgantga ggctacaaca acaggaaatc aatttcacaa    300

acatantact gag                                                       313


<210> SEQ ID NO 32
<211> LENGTH: 358
<212> TYPE: DNA
<213> ORGANISM: Homo sapiens
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t

<400> SEQUENCE: 32

tgttaagtac ttaagattta ttgaatgaga actgcattgt acaatatggt gccactagac     60

acgtctattt aatttaaatt aaaatataaa actctaaaac tagccatgat tcaaaggttc    120

aatagctata tgtgactagt ggctaccata taaaacattt ccatcacaaa gttccattta    180

tcagatctta tataggaacc ttgantaaaa tttaatagac aagtgatttt gtatttaaca    240

tttcaccttt attgaatgcc ctatagggcc atttgaatac gggtcatgtn caaggcacag    300

gggaaaaaaa aactgcagcn ggtaagggtt ttncaggggg gttttccagg tcccctcc      358


<210> SEQ ID NO 33
<211> LENGTH: 326
<212> TYPE: DNA
<213> ORGANISM: Homo sapiens
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
```

<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t

<400> SEQUENCE: 33

```
ttnnatatta nttatttttt attatacttt aagttttagg gtacatgtgc acaatgtcag     60

ggtttgttac atatgtatgg gcaaggactt catgtctaaa acaccaaaag caatggcaac    120

aaaagccaaa attgacaaaa gtagtatcat tctattatag ctgcatggaa aaagttaatt    180

tattaataca atggatgcct aaggncagaa gtactcaaac ttttggtctc agtactcctt    240

tacattctta aaaatcatta nggnccccaa ngantgtttg tttacaaggg ttacttacat    300

tgataattac cacatttgaa atgaaa                                         326
```

<210> SEQ ID NO 34
<211> LENGTH: 2301
<212> TYPE: DNA
<213> ORGANISM: Homo sapiens

<400> SEQUENCE: 34

```
tcgacagctc tctcgcccag cccagttctg gaagggataa aaagggggca tcaccgttcc     60

tgggtaacag agccaccttc tgcgtcctgc tgagctctgt tctctccagc acctcccaac    120

ccactagtgc ctggttctct tgctccacca ggaacaagcc accatgtctc gccagtcaag    180

tgtgtccttc cggagcgggg gcagtcgtag cttcagcacc gcctctgcca tcaccccgtc    240

tgtctcccgc accagcttca cctccgtgtc ccggtccggg ggtggcggtg gtggtggctt    300

cggcagggtc agccttgcgg gtgcttgtgg agtgggtggc tatggcagcc ggagcctcta    360

caacctgggg ggctccaaga ggatatccat cagcactaga ggaggcagct tcaggaaccg    420

gtttggtgct ggtgctggag gcggctatgg ctttggaggt ggtgccggta gtggatttgg    480

tttcggcggt ggagctggtg gtggctttgg gctcggtggc ggagctggct ttggaggtgg    540

cttcggtggc cctggctttc ctgtctgccc tcctggaggt atccaagagg tcactgtcaa    600

ccagagtctc ctgactcccc tcaacctgca aatcgacccc agcatccaga gggtgaggac    660

cgaggagcgc gagcagatca agaccctcaa caataagttt gcctccttca tcgacaaggt    720

gcggttcctg gagcagcaga acaaggttct ggacaccaag tggaccctgc tgcaggagca    780

gggcaccaag actgtgaggc agaacctgga gccgttgttc gagcagtaca tcaacaacct    840

caggaggcag ctggacagca tcgtggggga acggggccgc ctggactcag agctgagaaa    900

catgcaggac ctggtggaag acttcaagaa caagtatgag gatgaaatca acaagcgtac    960

cactgctgag aatgagtttg tgatgctgaa gaaggatgta gatgctgcct acatgaacaa   1020

ggtggagctg gaggccaagg ttgatgcact gatggatgag attaacttca tgaagatgtt   1080

ctttgatgcg gagctgtccc agatgcagac gcatgtctct gacacctcag tggtcctctc   1140

catggacaac aaccgcaacc tggacctgga tagcatcatc gctgaggtca aggcccagta   1200

tgaggagatt gccaaccgca gccggacaga agccgagtcc tggtatcaga ccaagtatga   1260

ggagctgcag cagacagctg gccggcatgg cgatgacctc cgcaacacca agcatgagat   1320

cacagagatg aaccggatga tccagaggct gagagccgag attgacaatg tcaagaaaca   1380
```

```
gtgcgccaat ctgcagaacg ccattgcgga tgccgagcag cgtggggagc tggccctcaa   1440

ggatgccagg aacaagctgg ccgagctgga ggaggccctg cagaaggcca agcaggacat   1500

ggcccggctg ctgcgtgagt accaggagct catgaacacc aagctggccc tggacgtgga   1560

gatcgccact taccgcaagc tgctggaggg cgaggaatgc agactcagtg gagaaggagt   1620

tggaccagtc aacatctctg ttgtcacaag cagtgtttcc tctggatatg gcagtggcag   1680

tggctatggc ggtggcctcg gtggaggtct tggcggcggc ctcggtggag gtcttgccgg   1740

aggtagcagt ggaagctact actccagcag cagtgggggt gtcggcctag gtggtgggct   1800

cagtgtgggg ggctctggct tcagtgcaag cagtggccga gggctggggg tgggctttgg   1860

cagtggcggg ggtagcagct ccagcgtcaa atttgtctcc accacctcct cctcccggaa   1920

gagcttcaag agctaagaac ctgctgcaag tcactgcctt ccaagtgcag caacccagcc   1980

catggagatt gcctcttcta ggcagttgct caagccatgt tttatccttt tctggagagt   2040

agtctagacc aagccaattg cagaaccaca ttctttggtt cccaggagag ccccattccc   2100

agcccctggt ctcccgtgcc gcagttctat attctgcttc aaatcagcct tcaggtttcc   2160

cacagcatgg cccctgctga cacgagaacc caaagttttc ccaaatctaa atcatcaaaa   2220

cagaatcccc accccaatcc caaattttgt tttggttcta actacctcca gaatgtgttc   2280

aataaaatgc ttttataata t                                             2301
```

<210> SEQ ID NO 35
<211> LENGTH: 448
<212> TYPE: DNA
<213> ORGANISM: Homo sapiens
<220> FEATURE:
<221> NAME/KEY: misc_feature
<222> LOCATION: (437)..(437)
<223> OTHER INFORMATION: n is a, c, g, or t

<400> SEQUENCE: 35

```
gatcatatta ttaaataata tatgcacaga catggagaga attagttttt actaaaacat     60

ttatcagaaa ttttaatact ctgcataacc agtattagca ttagaaatta gccactttta    120

aaatgagaaa actgtgtcac tcttcaattt ttttataagc cattgaggaa aacattaact    180

cctggatttc agcttcactt ttaacctgca gactaaattt ctttctcaat tatgtcagac    240

acacccaagt caatcccaac ccccttgtta ccttgggaag acccgtgctg aaaaaggaga    300

tcttccacct aaacacgtgt tctcttattt gaagcaaatc tttttgagaa tttgtttact    360

tgatttcttt ccacaataaa ctgacagaga acgctactaa tgattttttt ttttttttgg    420

agacggggtt ttgttcntgg ttggccca                                       448
```

<210> SEQ ID NO 36
<211> LENGTH: 219
<212> TYPE: DNA
<213> ORGANISM: Homo sapiens
<220> FEATURE:
<221> NAME/KEY: misc_feature
<222> LOCATION: (39)..(39)
<223> OTHER INFORMATION: n is a, c, g, or t

<400> SEQUENCE: 36

```
tgtttttttg aagtgactga ctaaaaagag aacagatana tacaagagtg tcgctggatc     60

ctattttata caaggattac gcctctcctg cttggccctt actgtcaccc tgtacaggta    120

caaaggctac aaaaaaggaa gcaatataaa cagacacaaa taacttttttt gcttttttac    180

atgcgatttg taagcttagt ttgagctatt cacaagcta                           219
```

<210> SEQ ID NO 37
<211> LENGTH: 2808
<212> TYPE: DNA
<213> ORGANISM: Homo sapiens

<400> SEQUENCE: 37

```
cggcatgaga ggccagcctg ccagggaaat ccaggaatct gcaacaaaaa cgatgacagt     60
ctgaaatact ctctggtgcc aacctccaaa ttctcgtctg tcacttcaga cccccactag    120
ttgacagagc agcagaatat caactccagt agacttgaat gtgcctctgg gcaaagaagc    180
agagctaacg aggaaaggga tttaaagagt ttttcttggg tgtttgtcaa acttttattc    240
cctgtctgtg tgcagagggg attcaacttc aatttttctgc agtggctctg ggtccagccc    300
cttacttaaa gatctggaaa gcatgaagac tgggcctttt ttcctatgtc tcttgggaac    360
tgcagctgca atcccgacaa atgcaagatt attatctgat cattccaaac caactgctga    420
aacggtagca cctgacaaca ctgcaatccc cagtttatgg gctgaagctg aagaaaatga    480
aaaagaaaca gcagtatcca cagaagacga ttcccaccat aaggctgaaa aatcatcagt    540
actaaagtca aaagaggaaa gccatgaaca gtcagcagaa cagggcaaga gttctagcca    600
agagctggga ttgaaggatc aagaggacag tgatggtcac ttaagtgtga atttggagta    660
tgcaccaact gaaggtacat tggacataaa agaagatatg attgagcctc aggagaaaaa    720
actctcagag aacactgatt ttttggctcc tggtgttagt tccttcacag attctaacca    780
acaagaaagt atcacaaaga gagaggaaaa ccaagaacaa cctagaaatt attcacatca    840
tcagttgaac aggagcagta aacatagcca aggcctaagg gatcaaggaa accaagagca    900
ggatccaaat atttccaatg gagaagagga agaagaaaaa gagccaggtg aagttggtac    960
ccacaatgat aaccaagaaa gaaagacaga attgcccagg gagcatgcta acagcaagca   1020
ggaggaagac aatacccaat ctgatgatat tttggaagag tctgatcaac caactcaagt   1080
aagcaagatg caggaggatg aatttgatca gggtaaccaa gaacaagaag ataactccaa   1140
tgcagaaatg gaagaggaaa atgcatcgaa cgtcaataag cacattcaag aaactgaatg   1200
gcagagtcaa gagggtaaaa ctggcctaga agctatcagc aaccacaaag agacagaaga   1260
aaagactgtt tctgaggctc tgctcatgga acctactgat gatggtaata ccacgcccag   1320
aaatcatgga gttgatgatg atggcgatga tgatggcgat gatggcggca ctgatggccc   1380
caggcacagt gcaagtgatg actacttcat cccaagccag gcctttctgg aggccgagag   1440
agctcaatcc attgcctatc acctcaaaat tgaggagcaa agagaaaaag tacatgaaaa   1500
tgaaaatata ggtaccactg agcctggaga gcaccaagag gccaagaaag cagagaactc   1560
atcaaatgag gaggaaacgt caagtgaagg caacatgagg gtgcatgctg tggattcttg   1620
catgagcttc cagtgtaaaa gaggccacat ctgtaaggca gaccaacagg gaaaacctca   1680
ctgtgtctgc caggatccag tgacttgtcc tccaacaaaa cccccttgatc aagtttgtgg   1740
cactgacaat cagacctatg ctagttcctg tcatctattc gctactaaat gcagactgga   1800
ggggaccaaa aaggggcatc aactccagct ggattatttt ggagcctgca aatctattcc   1860
tacttgtacg gactttgaag tgattcagtt tcctctacgg atgagagact ggctcaagaa   1920
tatcctcatg cagctttatg aagccaactc tgaacatgct ggttatctaa atgagaagca   1980
gagaaataaa gtcaagaaaa tttacctgga tgaaaagagg cttttggctg ggaccatcc   2040
cattgatctt ctcttaaggg actttaagaa aaactaccac atgtatgtgt atcctgtgca   2100
ctggcagttt agtgaacttg accaacaccc tatggataga gtcttgacac attctgaact   2160
```

```
tgctcctctg cgagcatctc tggtgcccat ggaacactgc ataacccgtt tctttgagga   2220

gtgtgacccc aacaaggata agcacatcac cctgaaggag tggggccact gctttggaat   2280

taaagaagag gacatagatg aaaatctctt gttttgaacg aagattttaa agaactcaac   2340

tttccagcat cctcctctgt tctaaccact tcagaaatat atgcagctgt gatacttgta   2400

gatttatatt tagcaaaatg ttagcatgta tgacaagaca atgagagtaa ttgcttgaca   2460

acaacctatg caccaggtat ttaacattaa ctttggaaac aaaaatgtac aattaagtaa   2520

agtcaacata tgcaaaatac tgtacattgt gaacagaagt ttaattcata gtaatttcac   2580

tctctgcatt gacttatgag ataattaatg attaaactat taatgataaa aataatgcat   2640

ttgtattgtt cataatatca tgtgcacttc aagaaaatgg aatgctactc ttttgtggtt   2700

tacgtgtatt attttcaata tcttaatacc ctaataaaga gtccataaaa atccaaaaaa   2760

aaaaaaaaaa aaaaaaaaaa aaaaaaaaaa aaaaaaaaaa aaaaaaaa                2808
```

<210> SEQ ID NO 38
<211> LENGTH: 416
<212> TYPE: DNA
<213> ORGANISM: Homo sapiens
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (285)..(286)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t

<400> SEQUENCE: 38

```
tttatttnnt tgaatctatt taattgctca gactgtgcta gagaatacgt accatgaaat     60

acatatattt cataaggttc agttacaaaa tggattgttt caaatggcaa tttcttacac    120

taacctgatt atgaaaaaaa gaagtctgta tcatctgctt ccaagtctgt tatgtccaaa    180

tatattttaa ttatgcattt attttgctac ttttataaat attagagatt tcaccntaaa    240

ttatttttgt aactagttct agaacatgtt tnccaattat tattnnccta atgggagaca    300

tataattgac cnatggttta tggcatatat ggtcctctac acagnggaac ctnttttttaa    360

aaggaatagg taaaggaaaa tgcgggacgg cctgggctct ccagggccaa gggcca        416
```

<210> SEQ ID NO 39
<211> LENGTH: 471
<212> TYPE: DNA
<213> ORGANISM: Homo sapiens
<220> FEATURE:
<221> NAME/KEY: misc_feature
<222> LOCATION: (6)..(6)

<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t

<400> SEQUENCE: 39

```
tttttntttt tttaaagtga atatacaatt tatttaacat tcaaacttca ttaagacatg     60

tgcaatatgg caattttact ggggattaaa ccctacctag gattgcttgc tggggcttag    120

caacagggtc cagttcacac ttagcactaa ttaaatactt tattgaataa atacaatacc    180

angcaaaatg cattcaaatg ctttctaaaa aaattttaaa ggcctttcta ctcaggctaa    240

tgacaaacac aataaaggca gatatgctag tttaacataa ttgggctgat tttatacagg    300

cacttatatc ttttagtcca caaggtatat tattaaatga taggggaaca tctnatacaa    360

ccatttctac agnactaggg gaattaaatt tctatgggaa ggaagggttt ttacagaccc    420

catctttttt tacccncccc aacagttcta actctaaggg ggttatagcc a             471
```

<210> SEQ ID NO 40
<211> LENGTH: 525
<212> TYPE: DNA
<213> ORGANISM: Homo sapiens

<400> SEQUENCE: 40

```
tttttttttt tttttttttg aaattttaac attttatatg catataaagc tgaacacatg     60

actaacaatc tagtggatgt gtatagaacc caacaattgc agaatatata ttcttttcaa    120

gcacacattg aatatttata aaaactgatc atatactgtg ccgtaagttt catctcagca    180

aatttcaaag ttttgatgcc atgaatgaaa tgaaacctga catttcaaaa ttataaacag    240

aatatgccct ggagtaactt gtggtattgt ttggggatga ggagagccat ccgaatagtg    300

ttttaaggaa agtctctatt cattgatctg ggtaacaagg gcaggaacca ttccaatgca    360

gaagctttgg ctaagcagtt gagcgttcag tagtgcatgt aaattcctgt gtgaaggctg    420

tggtgtcatg gctaaaggca tagcccctgg aacccagact gtttgggttc aaatctcagt    480

tctgctgctt aactcactgt gtgatggtgg gcaagttgcc taacc                    525
```

<210> SEQ ID NO 41
<211> LENGTH: 1402
<212> TYPE: DNA
<213> ORGANISM: Homo sapiens

<400> SEQUENCE: 41

```
ggggacgaag ggaagctcca gcgtgtggcc ccggcgagtg cggataaaag ccgccccgcc     60

gggctcgggc ttcattctga gccgagcccg gtgccaagcg cagctagctc agcaggcggc    120

agcggcggcc tgagcttcag ggcagccagc tccctcccgg tctcgccttc cctcgcggtc    180

agcatgaaag ccttcagtcc cgtgaggtcc gttaggaaaa acagcctgtc ggaccacagc    240

ctgggcatct cccggagcaa aacccctgtg gacgacccga tgagcctgct atacaacatg    300
```

-continued

```
aacgactgct actccaagct caaggagctg gtgcccagca tcccccagaa caagaaggtg    360

agcaagatgg aaatcctgca gcacgtcatc gactacatct tggacctgca gatcgccctg    420

gactcgcatc ccactattgt cagcctgcat caccagagac ccgggcagaa ccaggcgtcc    480

aggacgccgc tgaccaccct caacacggat atcagcatcc tgtccttgca ggcttctgaa    540

ttcccttctg agttaatgtc aaatgacagc aaagcactgt gtggctgaat aagcggtgtt    600

catgatttct tttattcttt gcacaacaac aacaacaaca aattcacgga atcttttaag    660

tgctgaactt atttttcaac catttcacaa ggaggacaag ttgaatggac ctttttaaaa    720

agaaaaaaaa aatggaagga aaactaagaa tgatcatctt cccagggtgt tctcttactt    780

ggactgtgat attcgttatt tatgaaaaag acttttaaat gccctttctg cagttggaag    840

gttttcttta tatactattc ccaccatggg gagcgaaaac gttaaaatca caaggaattg    900

cccaatctaa gcagactttg ccttttttca aaggtggagc gtgaatacca gaaggatcca    960

gtattcagtc acttaaatga agtcttttgg tcagaaatta ccttttttgac acaagcctac   1020

tgaatgctgt gtatatattt atatataaat atatctattt gagtgaaacc ttgtgaactc   1080

tttaattaga gttttcttgt atagtggcag agatgtctat ttctgcattc aaaagtgtaa   1140

tgatgtactt attcatgcta aactttttat aaaagtttag ttgtaaactt aaccctttta   1200

tacaaaataa atcaagtgtg tttattgaat ggtgattgcc tgctttattt cagaggacca   1260

gtgctttgat ttttattatg ctatgttata actgaaccca aataaataca agttcaaatt   1320

tatgtagact gtataagatt ataataaaac atgtctgaag tcaaaaaaaa aaaaaaaaaa   1380

aaaaaaaaaa aaaaaaaaaa aa                                             1402
```

<210> SEQ ID NO 42
<211> LENGTH: 2544
<212> TYPE: DNA
<213> ORGANISM: Homo sapiens

<400> SEQUENCE: 42

```
ctcactcaga cccatgaggc cctgcctggt ctcgtctggg acctgggaca gcagctggga     60

gacctgagcc tggagtctgg gggcctggaa caggagagcg ggcgtagctc gggcttctat    120

gaagatccca gctctacagg aggtccagat tcaccaccct caaccttctg tggggacagt    180

ggcttctctg gatccagctc ctatggtcgc ctgggtccct ctgagccccg gggcatctat    240

gccagtgaga ggcccaagtc cctaggagac gccagtccca gcgctccgga ggtggtgggc    300

gcgcgggcag cggtgccgcg gtccttctca gcgccctacc cgacggcagg tgggtcgccg    360

gcccggaggc ctgctcctcg gcggagcggc gggcccgcgc cgggcccttt ctgacgccca    420

gccccctgca cgccgtggcg atgcgcagcc cgcggccctg cggccgccct cccaccgact    480

cgcccgacgc ggggggcgca gggcggcccc tggacggcta catctcggcg ctcctgcgca    540

ggcgccgccg ccggggggcg ggccagcccc ggaccagtcc tgggggcgcg gacggcggcc    600

cgcggcgcca gaacagcgtg cgccagcggc cgcccgacgc gtctccgtcc cccggcagcg    660

cgcgacccgc gcgggagccc tcgttggagc gcgtcggggg ccaccccacc agccctgccg    720

ccttgagccg cgcctgggcg tcgtcgtggg agtcggaggc ggcacccgag cccgctgcgc    780

cgcccgccgc cccctcaccc cccgacagcc cggctgaggg ccgcttggtg aaggcgcagt    840

acatcccggg cgcgcaggcg gccacccgag gcctccctgg ccgcgccgcc cgccgcaaac    900

cgccgccact gacccgcggc cgcagcgtgg agcagtcacc accccgggag cgtccccggg    960

ccgccggccg ccgtggacgc atggccgagg cttcgggccg ccgcggctcg cccagggccc   1020
```

```
gcaaggcctc gcgctcccag tctgagacca gcctgctggg ccgcgcctcc gcggtccctt   1080

cggggccccc taagtacccc acggcggagc gggaagagcc tcggcctcca cggccacgcc   1140

gcggcccagc gcccacgctg gcggcccagg ccgcagggtc ctgccgtcgc tggcgctcca   1200

ctgcggagat cgacgctgcc gatgggcgcc gcgtgcggcc ccgagcccct gcggcgcgtg   1260

ttcccggccc cggcccgtcc ccgtcagctc cccagcgtcg tctgctttac ggctgcgcgg   1320

gcagcgactc cgagtgctcg gctgggcgcc tggggcccct gggacgccgg gggcctgcgg   1380

gaggcgtcgg cgggggttac ggggagagcg aatcgagcgc cagcgaggga gaatcgcctg   1440

ccttcagctc tgcctccagc gactcagacg gcagcggtgg cctcgtgtgg ccgcagcagc   1500

tggtggcggc caccgcggcc tctgggggtg gagcaggtgc aggggcgccc gcaggccccg   1560

ccaaagtctt cgtgaaaatc aaagcttccc acgcgctcaa gaaaaagata ctgcgtttcc   1620

gttcgggttc tctcaaggtc atgactacag tgtgagtttg gggatttgct tgggctcccc   1680

cttcatggcc tctgcacctc cacactccca accactgacc cttccacatc taccttccaa   1740

agaccatcgt ttctctgct tccaaagacc cccctcactc tccccactcc taacagtctt   1800

ggttgaaaag gctcccccac caccaccgag aggaatgggg aggagccctg tttgacccag   1860

ttcagcttct agcttggaag cccttgggca agacagttcc ccttctctgg gcgtcacttt   1920

cctcatctgt acagtaagtg tccatgtatg caaaaggggt aattcggttt gaatttcccc   1980

gttttagttt agaagcctag tctgtttgtt ccccttcacc gctctccctc tcattcctga   2040

tgagccctct cattcctcct ttccttgccc agctatggcc ccctctcatt cacaaagtgc   2100

cccctccatg tccctggacc cttaagatat ccccttggca ccctggtcag agactctgtg   2160

tctgactcag gtggtccctg cagagtgccc tgggaaggga aggagcactg atttgggggt   2220

tttgagggtc aagtaggggt tggtaacacc tggaaagaag gactctttca cttcgatccc   2280

tggacaatta tggaggattc ggaggtagaa gaggggaagg aagatggttt ctatctcatg   2340

acccccactc cctgtgagag ggaatggggg aagcctgatg accctcagct gttccaatct   2400

agtatttttt ttcttttttta aaattactgt atttattatg acgatggtga ctccccagtg   2460

caaagggggg ccagattctg tgtgtttctc taacctcttt gtaaataaat gcacagtgta   2520

acataaaaaa aaaaaaaaaa aaaa                                          2544
```

<210> SEQ ID NO 43
<211> LENGTH: 374
<212> TYPE: DNA
<213> ORGANISM: Homo sapiens
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t

<400> SEQUENCE: 43

```
aagcattaga gaagcatcag gccgccattc tagactcaac tgctcacctc ctctgatcca     60

ctgaggtgtc tctggaaatc ctccaccaca gccacagcct cctcaccact ctcagggtga    120

tgcagctgca cccaggtccg gagctcccca gggaggatgc tcaggaactg ctcaagcacc    180

agcagctcca ggatctgctc cttggtgtgc acctctgggc atgagccacc agcggcagag    240

cttcccgaag ccggctcaat gctttcctgc ggcccagaca tctcgtgggt aacacaattg    300

cctgaagtgt aggccggaag attttcgcag acaggaggat agttntttt gggagattgt     360
```

tggccttgnc ccca 374

<210> SEQ ID NO 44
<211> LENGTH: 4299
<212> TYPE: DNA
<213> ORGANISM: Homo sapiens

<400> SEQUENCE: 44
tgacagcgga ggcggcggcg gctgcaggct ccgagccgta ggagccggat cgggggaggg 60
gccgggccca ggagcctcag ccccgccggc agccctaagg gcaaggtaac cgccacgggg 120
tccccgtcgc gacccctcc ctcccggagc tcccgtcccc gggatcccaa gctccgcccc 180
gccgaccccc gtctcccctg gaccccggct ctagcctgac gagatcccca acctcctgag 240
gtgctctggc cccggattct cccgggctgc attctctgct cctcctcgcc tgcgaagcat 300
cacgtccgct tcccgacgct gagggcagcc ccgtccaggg cagtggctct gccaatgatc 360
ctgtgagtat tcaggaatca ctgttgcccc tggggatcct tgtcctggag tggcccacct 420
gcttgccccc agcatggcgt ccgacactcc cgagtcgctg atggccctct gtactgactt 480
ctgcttgcgc aacctggatg gcaccctggg ctacctgctg gacaaggaga ccctgcggct 540
acatccggac atcttcttgc ccagcgagat ctgtgaccgg ctcgtcaatg agtatgtgga 600
gctggtgaac gctgcctgta acttcgagcc acacgagagc ttcttcagcc tcttttcgga 660
cccccgcagc acccgcctca cgcggatcca cctccgtgag gacctggtgc aggaccagga 720
cctggaggcc atccgcaagc aggacctggt ggagctgtac ctgactaact gcgagaagct 780
gtccgccaag agcctgcaga cactgaggag cttcagccac accctggtgt ccttgagcct 840
cttcggctgt acaaacattt tctatgagga ggagaaccca gggggctgtg aagatgagta 900
cctcgtcaac ccccacctgcc aggtgctggt taaggatttc accttcgagg gcttcagccg 960
cctccgcttc ctcaacttgg gccgcatgat tgattgggtc cctgtggagt ccctgctgcg 1020
gccgcttaac tccctggctg ccttggacct ctcaggcatt cagacgagcg acgccgcctt 1080
cctcacccag tggaaagaca gcctggtgtc cctcgtcctc tacaacatgg acctgtccga 1140
cgaccacatc cgggtcatcg tgcagctgca caagctgcga cacctggaca tctcccgaga 1200
ccgcctctcc agctactaca agttcaagct gactcgggag gtgctgagcc tctttgtgca 1260
gaagctgggg aacctaatgt ccctggacat ctctggccac atgatcctag agaactgcag 1320
catctccaag atggaagagg aagcggggca gaccagcatt gagccttcca agagcagcat 1380
catacctttc cgggctctga agaggccgct gcagttcctc gggctctttg agaactctct 1440
gtgccgcctc acgcacattc cagcctacaa agtaagtggt gacaaaaacg aagagcaggt 1500
gctgaatgcc atcgaggcct acacggagca ccggcctgag atcacctcgc gggccatcaa 1560
cttgcttttt gacatcgccc gcatcgagcg ttgcaaccag ctgctgcggg ccctgaagct 1620
ggtcatcacg gccctcaagt gccacaaata tgacaggaac attcaagtga caggcagcgc 1680
cgctctcttc tacctaacaa attccgagta ccgctcagag cagagtgtga agctgcgccg 1740
gcaggttatc caggtggtgc tgaatggcat ggaatcctac caggaggtga cggtgcagcg 1800
gaactgctgc ctgacgctct gcaacttcag catccccgag gagctggaat tccagtaccg 1860
ccgggtcaac gagctcctgc tcagcatcct caaccccacg cggcaggacg agtctatcca 1920
gcggatcgcc gtgcacctgt gcaatgccct ggtctgccag gtagacaacg accacaagga 1980
ggccgtgggc aagatgggct ttgtcgtgac catgctgaag ctgattcaga agaagctgct 2040
ggacaagaca tgtgaccagg tcatggagtt ctcctggagt gccctgtgga acatcacaga 2100

```
tgaaactcct gacaactgcg agatgttcct caatttcaac ggcatgaagc tcttcctgga   2160

ctgcctgaag gaattcccag agaagcagga actgcatagg aatatgctag gacttttggg   2220

gaatgtggca gaagtgaagg agctgaggcc tcaactaatg acttcccagt tcatcagcgt   2280

cttcagcaac ctgttggaga gcaaggccga tgggatcgag gtttcctaca atgcctgcgg   2340

cgtcctctcc cacatcatgt ttgatggacc cgaggcctgg ggcgtctgtg agccccagcg   2400

tgaggaggtg gaggaacgca tgtgggctgc catccagagc tgggacataa actctcggag   2460

aaacatcaat tacaggtcat ttgaaccaat tctccgcctc cttccccagg gaatctctcc   2520

tgtcagccag cactgggcaa cctgggccct gtataacctc gtgtctgtct acccggacaa   2580

gtactgccct ctgctgatca aagaaggggg gatgcccctt ctgagggaca taattaagat   2640

ggcgaccgca cggcaggaga ccaaggaaat ggcccgcaag gtgattgagc actgcagtaa   2700

ctttaaagag gagaacatgg acacgtctag atagaggcct ccgtccccat ggccgccacc   2760

gctctggacc acaggcgggg aggaagcatg ctcaagcagc ccagcgggcg ggccccttcc   2820

gagggagcct cccacggagt gaagagacat gggggacttt tgcacaaccg acgcttttcc   2880

ttaatgttag tgagatatat atatattata tatatatatt ttttttttgg ttaggaagtg   2940

tgaagttttg tgtgtatgat ttctgtgcaa aaacaaaagc aacactcctg agtccttgca   3000

gcttccttgg ccattctcaa acccactcag ccttcatcgc tgacacacac actcctaccc   3060

caaccagact aaatgcctat aacgctgtga gtgtccagtc cttgtccagg aaactcagat   3120

cccggcctgg cttcctttca tgagaggagc aggccttgga cagcgtatcg agcatcctga   3180

cccactgccc ctgcctgaga acgccatctc ggctcccggg cacagctgat ggggtttggg   3240

gattagaact taccccactg ggtctcccaa aagccttggt gctcccggct gtgggccatc   3300

tggggcagga aagtgagcca ttcctaggct gaggtccagg cagccctgcc cctgaagacc   3360

ctctaggagc agggcaccca gtggccctgc tgctgtccag ccaggcctgc ctgaggccac   3420

gctgctatgg aggctgcctc ctagtctccc accaggtccc aggctgtgga aagccccagc   3480

ccagggatgg tcagaactcg gggcagatt ccactgcccc ttctgccaaa cacatccaga    3540

acctgccctc agccctggaa gctagcatct tctggggcca ggggcttgct tcctcgctcc   3600

atagccctca actgcccagg cgctcccacc agcagaactg agcctgcctc ctcctcccag   3660

cctgccccgc tgcccagagg accccacgcc tctcagaggc agaggtccca tgccagcctt   3720

tgacccacaa cggccacaca gccgcctcca gaccagcact cggactgccc tgcagtggcc   3780

gcttgggcct ccctggcggt cccgccctgc cctaggcttt accttggaag cctgagaggc   3840

gccggctctc ttgctcctcc atcgatggac actgcattgc ttctcatcgg acacttgtgg   3900

agcgcagggg cctggggagc agcgctaacc ctggaggcag cctttgggtg atggcttttt   3960

cttccctttt cctcccgcgg gcctgttttc aggtgttcct agcatttctg cctccaggca   4020

ggacggcagg ggtgagcagc tttgggagag acacctggcc tttttctcct ggagcctctc   4080

cctcccggcc ctgggaagtg ggcgcagccc tgtgttcccc cagcttggca gatgggctgc   4140

atgcggcgct cccttccttc ccacgctcag cggccccggc cagaccctgg cagacttcac   4200

acctcattgc tttacccct ggggcctggg gaaatgtctg tactttggga agtcacagaa    4260

atacattttt gtgcaaaatg gaaaaaaaaa aaaaaaaaa                          4299
```

<210> SEQ ID NO 45
<211> LENGTH: 6990
<212> TYPE: DNA
<213> ORGANISM: Homo sapiens

<400> SEQUENCE: 45

```
atggctgaga gcgcctcccc gccctcctca tctgcagcag ccccagccgc tgagccagga     60
gtcaccacgg agcagcccgg accccggagc cccccatcct ccccgccagg cctggaggag    120
cctctggatg gagctgatcc tcatgtccca cacccagacc tggcgcctat tgccttcttc    180
tgcctgcgac agaccaccag cccccggaac tggtgcatca agatggtgtg caacccgtgg    240
tttgaatgtg tcagcatgct ggtgatcctg ctgaactgcg tgacacttgg catgtaccag    300
ccgtgcgacg acatggactg cctgtccgac cgctgcaaga tcctgcaggt ctttgatgac    360
ttcatcttta tcttctttgc catggagatg gtgctcaaga tggtggccct ggggattttt    420
ggcaagaagt gctacctcgg ggacacatgg aaccgcctgg atttcttcat cgtcatggca    480
gggatggtcg agtactccct ggaccttcag aacatcaacc tgtcagccat ccgcaccgtg    540
cgcgtcctga ggcccctcaa agccatcaac cgcgtgccca gtatgcggat cctggtgaac    600
ctgctcctgg acacactgcc catgctgggg aatgtcctgc tgctctgctt ctttgtcttc    660
ttcatctttg gcatcatagg tgtgcagctc tgggcgggcc tgctgcgtaa ccgctgcttc    720
ctggaggaga acttcaccat acaaggggat gtggccttgc cccatactac ccagccggag    780
gaggatgatg agatgccctt catctgctcc ctgtcgggcg acaatgggat aatgggctgc    840
catgagatcc ccccgctcaa ggagcagggc cgtgagtgct gcctgtccaa ggacgacgtc    900
tacgactttg ggcggggcg ccaggacctc aatgccagcg gcctctgtgt caactggaac     960
cgttactaca atgtgtgccg cacgggcagc gccaaccccc acaagggtgc catcaacttt   1020
gacaacatcg gttatgcttg gattgtcatc ttccaggtga tcactctgga aggctgggtg   1080
gagatcatgt actacgtgat ggatgctcac tccttctaca acttcatcta cttcatcctg   1140
cttatcatag tgggctcctt cttcatgatc aacctgtgcc tcgttgtcat agcgacccag   1200
ttctcggaga ccaagcaacg ggagcaccgg ctgatgctgg agcagcggca gcgctacctg   1260
tcctccagca cggtggccag ctacgccgag cctggcgact gctacgagga gatcttccag   1320
tatgtctgcc acatcctgcg caaggccaag cgccgcgccc tgggcctcta ccaggccctg   1380
cagagccggc gccaggccct gggcccggag gccccggccc ccgccaaacc tgggccccac   1440
gccaaggagc cccggcacta ccatgggaag actaagggtc agggagatga agggagacat   1500
ctcggaagcc ggcattgcca gactttgcat gggcctgcct cccctggaaa tgatcactcg   1560
ggaagagagc tgtgcccgca acatagcccc ctggatgcga cgccccacac cctggtgcag   1620
cccatccccg ccacgctggc ttccgatccc gccagctgcc cttgctgcca gcatgaggac   1680
ggccggcggc cctcgggcct gggcagcacc gactcgggcc aggagggctc gggctccggg   1740
agctccgctg gtggcgagga cgaggcggat ggggacgggg cccggagcag cgaggacgga   1800
gcctcctcag aactggggaa ggaggaggag gaggaggagc aggcggatgg ggcggtctgg   1860
ctgtgcgggg atgtgtggcg ggagacgcga gccaagctgc gcggcatcgt ggacagcaag   1920
tacttcaacc ggggcatcat gatggccatc ctggtcaaca ccgtcagcat gggcatcgag   1980
caccacgagc agccggagga gctgaccaac atcctggaga tctgcaatgt ggtcttcacc   2040
agcatgtttg ccctggagat gatcctgaag ctggctgcat ttgggctctt cgactacctg   2100
cgtaacccct acaacatctt cgacagcatc attgtcatca tcagcatctg ggagatcgtg   2160
gggcaggcgg acggtgggct gtcggtgctg cggaccttcc ggctgctgcg cgtgctgaaa   2220
ctggtgcgct tcatgcctgc cctgcggcgc cagctcgtgg tgctcatgaa gaccatggac   2280
aacgtggcca ccttctgcat gctgctcatg ctcttcatct tcatcttcag catccttggg   2340
```

```
atgcatattt ttggctgcaa gttcagcctc cgcacggaca ctggagacac ggtgcccgac   2400

aggaagaact tcgactccct gctgtgggcc atcgtcactg tgttccagat cctcacccag   2460

gaggactgga acgtcgttct ctacaatggc atggcctcca cttctccctg ggcctccctc   2520

tactttgtcg ccctcatgac cttcggcaac tatgtgctct tcaacctgct ggtggccatc   2580

ctggtggagg gcttccaggc ggagggtgac gccaatcgct cctactcgga cgaggaccag   2640

agctcatcca acatagaaga gtttgataag ctccaggaag gcctggacag cagcggagat   2700

cccaagctct gcccaatccc catgaccccc aatgggcacc tggaccccag tctcccactg   2760

ggtgggcacc taggtcctgc tggggctgcg ggacctgccc cccgactctc actgcagccg   2820

gaccccatgc tggtggccct gggctcccga aagagcagtg tcatgtctct agggaggatg   2880

agctatgacc agcgctccct gtccagctcc cggagctcct actacgggcc atggggccgc   2940

agcgcggcct gggccagccg tcgctccagc tggaacagcc tcaagcacaa gccgccgtcg   3000

gcggagcatg agtccctgct ctctgcggag cgcggcggcg gcgcccgggt ctgcgaggtt   3060

gccgcggacg aggggccgcc gcgggccgca cccctgcaca ccccacacgc ccaccacatt   3120

catcacgggc cccatctggc gcaccgccac cgccaccacc gccggacgct gtccctcgac   3180

aacagggact cggtggacct ggccgagctg gtgcccgcgg tgggcgccca cccccgggcc   3240

gcctggaggg cggcaggccc ggcccccggg catgaggact gcaatggcag gatgcccagc   3300

atcgccaaag acgtcttcac caagatgggc gaccgcgggg atcgcgggga ggatgaggag   3360

gaaatcgact acaccctgtg cttccgcgtc cgcaagatga tcgacgtcta taagcccgac   3420

tggtgcgagg tccgcgaaga ctggtctgtc tacctcttct ctcccgagaa caggttccgg   3480

gtcctgtgtc agaccattat tgcccacaaa ctcttcgact acgtcgtcct ggccttcatc   3540

tttctcaact gcatcaccat cgccctggag cggcctcaga tcgaggccgg cagcaccgaa   3600

cgcatctttc tcaccgtgtc caactacatc ttcacggcca tcttcgtggg cgagatgaca   3660

ttgaaggtag tctcgctggg cctgtacttc ggcgagcagg cgtacctacg cagcagctgg   3720

aacgtgctgg atggctttct tgtcttcgtg tccatcatcg acatcgtggt gtccctggcc   3780

tcagccgggg gagccaagat cttgggggtc ctccgagtct tgcggctcct gcgcacccta   3840

cgcccccctgc gtgtcatcag ccgggcgccg ggcctgaagc tggtggtgga gacactcatc   3900

tcctccctca agcccatcgg caacatcgtg ctcatctgct gtgccttctt catcatcttt   3960

ggcatcctgg gagtgcagct cttcaagggc aagttctacc actgtctggg cgtggacacc   4020

cgcaacatca ccaaccgctc ggactgcatg gccgccaact accgctgggt ccatcacaaa   4080

tacaacttcg acaacctggg ccaggctctg atgtccctct ttgtcctggc atccaaggat   4140

ggttgggtga acatcatgta caatggactg gatgctgttg ctgtggacca gcagcctgtg   4200

accaaccaca acccctggat gctgctgtac ttcatctcct tcctgctcat cgtcagcttc   4260

tttgtgctca acatgtttgt gggtgtcgtg gtggagaact tccacaagtg ccggcagcac   4320

caggaggctg aagaggcacg gcggcgtgag gagaagcggc tgcggcgcct ggagaagaag   4380

cgccggaagg cccagcggct gccctactat gccacctatt gtcacacccg gctgctcatc   4440

cactccatgt gcaccagcca ctacctggac atcttcatca ccttcatcat ctgcctcaac   4500

gtggtcacca tgtccctgga gcactacaat cagcccacgt ccctggagac agccctcaag   4560

tactgcaact atatgttcac cactgtcttt gtgctggagg ctgtgctgaa gctggtggca   4620

tttggtctga ggcgcttctt caaggaccga tggaaccagc tggacctggc cattgtgcta   4680

ctgtcagtca tgggcatcac cctggaggag atcgagatca atgcggccct gcccatcaat   4740
```

-continued

```
cccaccatca tccgcatcat gagggttctg cgcattgccc gagtgctgaa gctgttgaag   4800

atggccacag gaatgcgggc cctgctggac acggtggtgc aagctttgcc ccaggtgggc   4860

aacctgggcc tcctcttcat gctgctcttc ttcatctatg ctgctctcgg ggtggagctc   4920

tttgggaagc tggtctgcaa cgacgagaac ccgtgcgagg gcatgagccg gcatgccacc   4980

ttcgagaact tcggcatggc cttcctcaca ctcttccagg tctccacggg tgacaactgg   5040

aacgggatca tgaaggacac gctgcgggac tgcacccacg acgagcgcag ctgcctgagc   5100

agcctgcagt ttgtgtcgcc gctgtacttc gtgagcttcg tgctcaccgc gcagttcgtg   5160

ctcatcaacg tggtggtggc tgtgctcatg aagcacctgg acgacagcaa caaggaggcg   5220

caggaggacg ccgagatgga tgccgagctc gagctggaga tggcccatgg cctgggccct   5280

ggcccgaggc tgcctaccgg ctccccgggc gcccctggcc gagggccggg aggggcgggc   5340

ggcgggggcg acaccgaggg cggcttgtgc cggcgctgct actcgcctgc ccaggagaac   5400

ctgtggctgg acagcgtctc tttaatcatc aaggactcct tggaggggga gctgaccatc   5460

atcgacaacc tgtcgggctc catcttccac cactactcct cgcctgccgg ctgcaagaag   5520

tgtcaccacg acaagcaaga ggtgcagctg gctgagacgg aggccttctc cctgaactca   5580

gacaggtcct cgtccatcct gctgggtgac gacctgagtc tcgaggaccc cacagcctgc   5640

ccacctggcc gcaaagacag caagggtgag ctggacccac ctgagcccat gcgtgtggga   5700

gacctgggcg aatgcttctt cccccttgtcc tctacggccg tctcgccgga tccagagaac   5760

ttcctgtgtg agatggagga gatcccattc aaccctgtcc ggtcctggct gaaacatgac   5820

agcagtcaag cacccccaag tcccttctcc ccggatgcct ccagccctct cctgcccatg   5880

ccagccgagt tcttccaccc tgcagtgtct gccagccaga aaggcccaga aaagggcact   5940

ggcactggaa ccctccccaa gattgcgctg cagggctcct gggcatctct gcggtcacca   6000

agggtcaact gtaccctcct ccggcaggcc accgggagcg acacgtcgct ggacgccagc   6060

cccagcagct ccgcgggcag cctgcagacc acgctcgagg acagcctgac cctgagcgac   6120

agcccccggc gtgccctggg gccgcccgcg cctgctccag gaccccgggc cggcctgtcc   6180

cccgccgctc gccgccgcct gagcctgcgc ggccggggcc tcttcagcct gcgggggctg   6240

cgggcgcatc agcgcagcca cagcagcggg ggctccacca gcccgggctg cacccaccac   6300

gactccatgg acccctcgga cgaggagggc cgcggtggcg cgggcggcgg gggcgcgggc   6360

agcgagcact cggagaccct cagcagcctc tcgctcacct ccctcttctg cccgccgccc   6420

ccgccgccag cccccggcct cacgcccgcc aggaagttca gcagcaccag cagcctggcc   6480

gcccccggcc gcccccacgc cgccgccctg gcccacggcc tggcccggag cccctcgtgg   6540

gccgcggacc gcagcaagga cccccccggc cgggcaccgc tgcccatggg cctgggcccc   6600

ttggcgcccc cgccgcaacc gctccccgga gagctggagc cgggagacgc cgccagcaag   6660

aggaagagat gagggtcgca ggggcccccg gccgcccacc gcccgccccg tctcaccttc   6720

tttacctcag gagccaggag cagacagcaa tacttcgtcc acacctggga tcgcgcaggg   6780

cccgcagggc acaggcgccc gacagccggg ctgagcggag tctgggttag ccaggcctgc   6840

gtggcccatg gtggcccttc cagtgcatat acatacatat atatatatat atgcatatat   6900

atatatatat atatatatat gtgtatacac acacacatag acagacatat atatatatat   6960

ttattttttt tactgagagc ttatgacttc                                     6990
```

<210> SEQ ID NO 46
<211> LENGTH: 139
<212> TYPE: DNA

```
<213> ORGANISM: Homo sapiens
<220> FEATURE:
<221> NAME/KEY: misc_feature
<222> LOCATION: (138)..(138)
<223> OTHER INFORMATION: n is a, c, g, or t

<400> SEQUENCE: 46

ctaatatttg catgtacaca atgagttatc ttagggaggg gatccaagtg gaaacacaaa      60

atttattttt gtgtgtatac acacatacac acatcactta tatacatagc cttaaggtaa     120

ttttataccg tatttttng                                                  139


<210> SEQ ID NO 47
<211> LENGTH: 674
<212> TYPE: DNA
<213> ORGANISM: Homo sapiens

<400> SEQUENCE: 47

ccccttggtt ccgcccgcgc gtcacgtgac cccagcgcct acttgggctg aggagccgcc      60

gcgtcccctc gccgagtccc ctcgccagat tccctccgtc gccgccaaga tgatgtgcgg     120

ggcgccctcc gccacgcagc cggccaccgc cgagacccag cacatcgccg accaggtgag     180

gtcccagctt gaagagaaag aaaacaagaa gttccctgtg tttaaggccg tgtcattcaa     240

gagccaggtg gtcgcgggga caaactactt catcaaggtg cacgtcggcg acgaggactt     300

cgtacacctg cgagtgttcc aatctctccc tcatgaaaac aagcccttga ccttatctaa     360

ctaccagacc aacaaagcca agcatgatga gctgacctat ttctgatcct gactttggac     420

aaggcccttc agccagaaga ctgacaaagt catcctccgt ctaccagagc gtgcacttgt     480

gatcctaaaa taagcttcat ctccgggctg tgccccttgg ggtggaaggg gcaggattct     540

gcagctgctt ttgcatttct cttcctaaat ttcattgtgt tgatttcttt ccttcccaat     600

aggtgatctt aattactttc agaatatttt caaaatagat atatttttaa aatccttaaa     660

aaaaaaaaaa aaaa                                                       674


<210> SEQ ID NO 48
<211> LENGTH: 6276
<212> TYPE: DNA
<213> ORGANISM: Homo sapiens

<400> SEQUENCE: 48

agtcggcatc catcagcggg cgggggtgtc gccgaacagg ctgctccgca gagcccgccg      60

cgaccccgcg ccgccccgcc ccgcggcctg cctgccagag gagccgaggg ggccgcccct     120

cgcccaacct gcccgacatg gggaaccccg ggcccaggcg tgctggtcac catgacaaca     180

gagacaggcc ccgactctga ggtgaagaaa gctcaggagg aggccccgca gcagcccgag     240

gctgctgccg ctgtgaccac ccctgtgacc cctgcaggcc acggccaccc agaggccaac     300

tccaatgaga agcatccatc ccagcaggac acgcggcctg ctgaacagag cctagacatg     360

gaggagaagg actacagtga ggccgatggc ctttcggaga ggaccacgcc cagcaaggcc     420

cagaaatcgc cccagaagat tgccaagaaa tacaagagtg ccatctgccg ggtcactctg     480

cttgatgcct cggagtatga gtgtgaggtg gagaaacatg gccggggcca ggtgctgttt     540

gacctggtct gtgaacacct caacctccta gagaaggact acttcggcct gaccttctgt     600

gatgctgaca gccagaagaa ctggctggac ccctccaagg agatcaagaa gcagatccgg     660

agtagcccct ggaattttgc cttcacagtc aagttctacc cgcctgatcc tgcccagctg     720

acagaagaca tcacaagata ctacctgtgc ctgcagctgc gggcagacat catcacgggc     780
```

-continued

```
cggctgccat gctcctttgt cacgcatgcc ctactgggct cctacgctgt gcaggctgag    840
ctgggtgact atgatgctga ggagcatgtg ggcaactatg tcagcgagct ccgcttcgcc    900
cctaaccaga cccgggagct ggaggagagg atcatggagc tgcataagac atatagggggg   960
atgaccccgg gagaagcaga aatccacttc ttagagaatg ccaagaagct ttccatgtac   1020
ggagtagacc tgcaccatgc caaggactct gagggcatcg acatcatgtt aggcgtttgt   1080
gccaatggcc tgctcatcta ccgggaccgg ctgagaatca accgctttgc ctggcccaag   1140
atcctcaaga tctcctacaa gaggagtaac ttctatatca agatccggcc tggggagtat   1200
gagcaatttg agagcacaat tggctttaag ctcccaaacc accggtcagc caagagactg   1260
tggaaggtct gcatcgagca tcatacattc ttccggctgg tgtcccctga gcccccaccc   1320
aagggcttcc tggtgatggg ctccaagttc cggtacagtg ggaggaccca ggcacagact   1380
cgccaggcca gcgccctcat tgaccggcct gcacccttct ttgagcgttc ttccagcaaa   1440
cggtacacca tgtcccgcag ccttgatgga gcagagttct cccgcccagc ctcggtcagc   1500
gagaaccatg atgcagggcc tgacggtgac aagcgggatg aggatggcga gtctgggggg   1560
caacggtcag aggctgagga gggagaggtc aggactccaa ccaagatcaa ggagctaaag   1620
ccggagcagg aaaccacgcc gagacacaag caggagttct tagacaagcc agaagatgtc   1680
ttgctgaagc accaggccag catcaatgag ctcaaaagga ccctgaagga gcccaacagc   1740
aaactcatcc accgggatcg agactgggaa cgggagcgca ggctgccctc ctcccccgcc   1800
tcccccctccc ccaagggcac ccctgagaaa gccaatgaga gagcagggct gagggagggc   1860
tccgaggaga aagtcaaacc accacgtccc cgggccccag agagtgacac aggcgatgag   1920
gaccaggacc aggagaggga cacggtgttc ctgaaggaca accacctggc cattgagcgc   1980
aagtgctcca gcatcacggt cagctctacg tctagcctgg aggctgaggt ggacttcacg   2040
gtcattggtg actaccatgg cagcgccttc gaagacttct cccgcagcct gcctgagctc   2100
gaccgggaca aaagcgactc ggacactgag ggcctgctgt tctcccggga tctcaacaag   2160
ggggccccca gccaggatga tgagtctggg ggcattgagg acagcccgga tcgagggggcc  2220
tgctccaccc cggatatgcc ccagtttgag cccgtgaaaa cagaaaccat gactgtcagc   2280
agtctggcca ttagaaagaa gattgagccg gaggccgtac tgcagaccag agtctccgct   2340
atggataaca cccagcaggt tgatgggagt gcctcagtgg ggagggagtt catagcaacc   2400
actccctcca tcaccacgga gaccatatcg accaccatgg agaacagtct caagtccggg   2460
aagggggcag ctgccatgat cccaggccca cagacggtgg ccacggaaat ccgttctctt   2520
tctccgatca tcgggaaaga tgtcctcacc agcacctacg gcgccactgc ggaaaccctc   2580
tcaacctcca ccaccaccca tgtcaccaaa actgtgaaag gagggttttc tgagacaagg   2640
atcgagaagc gaatcatcat tactggggat gaagatgtcg atcaagacca ggccctggct   2700
ttggccatca aggaggccaa actgcagcat cctgatatgc tggtaaccaa agctgtcgta   2760
tacagagaaa cagacccatc cccagaggag agggacaaga agccacagga atcctgacct   2820
ctgtgaagag atcctggcat ttctggtcca acccaagcca gagaaccatt aagaaggggc   2880
cttcattctg gattctccga cgcaacactg acgtcccagc tgcgacgtac tgtcactgat   2940
gagagactgg gaagggaaaa gcatatatat atagatatat agagatatag atatatatac   3000
aggaaacacc gcatccttgc actgctgctg gggctggcag agcagttggc tgacagcaac   3060
aaccgacatc tgaacaccta catttccttt gcagacaaat tgaagaactg gtgggatttt   3120
tttcaagaaa aaaaattata taataactat aatcccttgc tcaccccttt cccccgccaa   3180
```

```
ataagaaacg caagccagac cacgatgatt gtagaagtcc ctcccgccct ggttctgcac   3240

gttacagtta gcagacgagc aattccattt gttcttctcc agcatctcta aggcccactt   3300

gaatgcaaag gaaaacactt gcacagcaaa gcaagagaag tcacagcagc aagacacgca   3360

cagtcaacca ttttccgaga aaaaaagaaa attccccact tggaaagaaa gaggaggaac   3420

actggattct tactttctgg atcttgacac tgggctgcaa aacctacctt cctctctccc   3480

gcctcccctc accctcaact ctcaatgtct tgctgtcatt ttctgtctcg gctccctcct   3540

ccccccttccc ccttccccca ccccacaccc ttcaccctct gtgtcctggt ccttctgagg   3600

gccactgcag atgactctcc tttgaaatga gaaaaagaaa agaaagcaag aacagaaaac   3660

gaagccacag gaagggaagt agacattgta tgcttatggt ttctcattat gaaggtgcag   3720

cttgtaggag gtttgtacgg atgtgctttg aagttatgta tattacatat aacaggaaaa   3780

aatattaaaa taaacagtgc tggtaagtat gaagctgaca ttctaaaatt ataattatct   3840

gactgtgatt gatgtatcct gaggttccta gatctcactg aactggccca gctaaggaga   3900

cctggactct gggtgtgggt tggctcacag taggggctga cgggttcagt gtagtaatac   3960

tgtgtgtggt gtttgtaatt ggttgattgg tggggagggg tggggggccc taatggagag   4020

gtgtgggttt ggcaagaaag aagcaacaca gatgtcgtcc ccaaaatgcc agttcaagac   4080

accttctccc tgccccccctg gtagtaacag tcagggcctg gtctgtgctc aggtactggg   4140

tcccagtctg ggactctgct gctgaagttg ccacagtaga ggtccctggc ttagtcctta   4200

tctccctacg gggcttgcct tggttttcag tcttctctct ctttctctct tttttttttt   4260

tttgccacat tctgcccttc cctgacccca ttgtaataac caactccata tccaaaggga   4320

ggtggtgctc tcagccattg tagaagatgg tggctttaac ctgactgtct aaaaattccc   4380

agctaagcct tttcctctac tctcttcctt gttctgaatc atttcttctt ctcaggccaa   4440

agtagccatg gtaaggaggc ttcatggggc agaccctgaa agatcaaaac tgcatttgca   4500

aagccctccc ctgtcccagg acaaagctga gactgacggg tgatgttgct cataggctcc   4560

agctctgcat aagaccttgg cttggagacc tccctctcag tcaacagctg aactctgagc   4620

ttgtgcccag aaattacccc aagaccacag gaacccttca agaagctccc atcacaagct   4680

tggcattgct ctctgccaca cgtgggcttc ctcaggcttg tctgccacaa gctacttctc   4740

tgagctcaga aagtgcccct tgatgaggga aaatgtccca ctgcactgcg aatttctcag   4800

ttccatttta cctcccagtc ctccttctaa accagttaat aaattcattc cacaagtatt   4860

tactgattac ctgcttgtgc cagggactat tctcaggctg aagaaggtgg gaggggaggg   4920

cggaacctga ggagccacct gagccagctt tatatttcaa ccatggctgg cccatctgag   4980

agcatctccc cactctcgcc aacctatcgg ggcatagccc agggatgccc ccaggcggcc   5040

caggttagat gcgtcccttt ggcttgtcag tgatgacata caccttagct gcttagctgg   5100

tgctggcctg aggcagggca ggaaatcaga atagcatttg cttctctggg caaatgggaa   5160

gttcagcggg gcagcagaat cagtggcatt ccccctggtg caggccggtg ggtccactcc   5220

aactccccct gagtgtagca gcacactttc catacaccag gttctttcta caatcctggt   5280

ggaaaagcca cagaaccttc ttcctgccct tcttgagagt tccccctctt tctgggtcaa   5340

gagctggagt ggtggctcca tcctctctgg gccacttcgg tctaggaact catctttgca   5400

ggaaccagga gtcctgagca cactgaacac acctcagagg gaggatcctt gttgtggatt   5460

ttgcacctgg ctttggggca ggggtgaagt gaccaggctt agcttgtgga gtttatgggc   5520

caccagggtt tggggaaatc accatcccgc ggatgctgtg acctcccttc tacggagatg   5580
```

```
caggcagtgc cacgagggag gaggggacct gcaaagctag aatctagggc actgtttcct   5640

ccccatcctt ctctttgtag agaatagaga cgtttgtctt gtctgtcttc aacctacttt   5700

tccttttctc ttttttgttt ctcatcctct ctgtgccacc tctccaccca ggaggccatg   5760

tagcatagtg gaaaaagtcc ctgagggcgg ttaggagttc tgggtgacca tcctggctca   5820

gctcctaact caccatgtga catcaggcta tccccattcc ccctcttggg cctcagtttc   5880

ccgacttgca aaataagcag aaagaaccag atgctctcca gggtcttttt ctactttgct   5940

atctcatggg tcttcatttt ctcttatttt gttttctctg gatcttttcc atctgagggt   6000

acaggaagta ccaggacctg tttcagtttt tgaatcctgc aagcacattc caagactggc   6060

ctgaaactgc atgagcaaca tcactcgaaa taattttttt tttcaaaagc accttaacaa   6120

ccaattgcga tgctgtcctg ttccttttta ctcacaccct tctctccttt ctcgtcccca   6180

tgctccccca cctcagtgct ccgtgctgta tgcgtgtgct ctctgttctt gtatactcaa   6240

tataagtgaa ataaatgtgt ttgatgctga accata                             6276
```

<210> SEQ ID NO 49
<211> LENGTH: 982
<212> TYPE: DNA
<213> ORGANISM: Homo sapiens

<400> SEQUENCE: 49

```
ggctcatcca cctgcagaca tggggcgcag aaagtcaaaa cgaaagccgc ctcccaagaa     60

gaagatgaca ggcaccctcg agacccagtt cacctgcccc ttctgcaacc acgagaaatc    120

ctgtgatgtg aaaatggacc gtgcccgcaa caccggagtc atctcttgta ccgtgtgcct    180

agaggaattc cagacgccca taacgtatct gtcagaaccc gtggatgtgt acagtgattg    240

gatagacgcc tgcgaggcgg ccaatcagta gcgacacaga ggacccgccc cctgagcagc    300

cccgcgtact gtggatccag ctgttcggtt ctggtccaga gacattccag gggtccaggg    360

tgtgggtcct gggctgtcac agccgtgtgt gtgtgtgtgt gtgtgtgtgt gtgtgtgtgt    420

gtgtgtgtag tgggtgtgcg tgtgggtgtg ggtgtgagtg agtgtgggtg tgtgtggctg    480

cacgtgtcac tggggtggcc gtgagtgtgt gctcacaggt acgcggtggt gtcgggttcc    540

tgggcctgag ggcctgaac tgatctcact tggctccgaa agcctttgct gtgttccctg    600

cagcccctgg ccccccagcc ttggggctct ggctccccc ggcggaattg ggggactgtt    660

tcctgacatc ctggacaagg gaagcccact agaggctgga acaggacctc tccagcctcc    720

tcaccagcac cgtgcccatc tcaactggac ttcccgccct ccttctccac cttctagtgc    780

ccgtggccgg ggattcaaag ccgccgttcc ccaggtccct gggctgggcc ctgacaggga    840

gccgcccccc tccccatggt aaccaggaag cccgtttcat gttcagttgc ttttgtagag    900

gaagcaaggg ctgggatggg gacagctgtc aatcacaagc ccttaaataa agcagccagc    960

gcacaaaaaa aaaaaaaaaa aa                                             982
```

<210> SEQ ID NO 50
<211> LENGTH: 1767
<212> TYPE: DNA
<213> ORGANISM: Homo sapiens

<400> SEQUENCE: 50

```
gaaaggagca agccaggaag ccagacaaca acagcatcaa aacaaggctg tttctgtgtg     60

tgaggaactt tgcctgggag ataaaattag acctagagct ttctgacagg gagtctgaag    120

cgtgggacat ggaccgttca ctgggatggc aagggaattc tgtccctgag gacaggactg    180
```

```
aagctgggat caagcgtttc ctggaggaca ccacggatga tggagaactg agcaagttcg    240

tgaaggattt ctcaggaaat gcgagctgcc acccaccaga ggctaagacc tgggcatcca    300

ggccccaagt cccggagcca aggccccagg ccccggacct ctatgatgat gacctggagt    360

tcagaccccc ctcgcggccc cagtcctctg acaaccagca gtacttctgt gccccagccc    420

ctctcagccc atctgccagg ccccgcagcc catggggcaa gcttgatccc tatgattcct    480

ctgaggatga caaggagtat gtgggctttg caaccctccc caaccaagtc caccgaaagt    540

ccgtgaagaa aggctttgac tttaccctca tggtggcagg agagtctggc ctgggcaaat    600

ccacacttgt caatagcctc ttcctcactg atctgtaccg ggaccggaaa cttcttggtg    660

ctgaagagag gatcatgcaa actgtggaga tcactaagca tgcagtggac atagaagaga    720

agggtgtgag gctgcggctc accattgtgg acacaccagg ttttggggat gcagtcaaca    780

acacagagtg ctggaagcct gtggcagaat acattgatca gcagtttgag cagtatttcc    840

gagacgagag tggcctgaac cgaaagaaca tccaagacaa cagggtgcac tgctgcctgt    900

acttcatctc acccttcggc catgggctcc ggccattgga tgttgaattc atgaaggccc    960

tgcatcagcg ggtcaacatc gtgcctatcc tggctaaggc agacacactg acacctcccg   1020

aagtggacca caagaaacgc aaaatccggg aggagattga gcattttgga atcaagatct   1080

atcaattccc agactgtgac tctgatgagg atgaggactt caaattgcag gaccaagccc   1140

taaaggaaag catcccattt gcagtaattg gcagcaacac tgtagtagag gccagagggc   1200

ggcgagttcg ggtcgactc tacccctggg gcatcgtgga agtggaaaac ccagggcact    1260

gcgactttgt gaagctgagg acaatgctgg tacgtaccca catgcaggac ctgaaggatg   1320

tgacacggga gacacattat gagaactacc gggcacagtg catccagagc atgacccgcc   1380

tggtggtgaa ggaacggaat cgcaacaaac tgactcggga aagtggtacc gacttcccca   1440

tccctgctgt cccaccaggg acagatccag aaactgagaa gcttatccga gagaaagatg   1500

aggagctgcg gcggatgcag gagatgctac acaaaataca aaaacagatg aaggagaact   1560

attaactggc tttcagccct ggatatttaa atctcctcct cttcttcctg tccatgccgg   1620

cccctcccag caccagctct gctcaggccc cttcagctac tgccacttcg ccttacatcc   1680

ctgctgactg cccagagact cagaggaaat aaagtttaat aaatctgtag gtggctaaaa   1740

aaaaaaaaaa aaaaaaaaaa aaaaaaa                                        1767
```

<210> SEQ ID NO 51
<211> LENGTH: 339
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t

<400> SEQUENCE: 51

```
naaatgttaa tagtaacttt tatttgaaag ttagggagat gaaaatacat ttccaaattc      60
```

```
ttccaaagat atagctaaat gacaaaataa aaacttcact atgggccagg cgcggtgact    120

cacgcctgta atcctagcac tttgggaggc cgaggcaggt ggatcacctg agagcaggag    180

attgagacca gcctggccaa cttggtgaaa accctatctc tactaaaaaa tacaaaaact    240

agccgngcat gatggcgtat gtttgtaaat ccccagctac ttngggacat taagggcaga    300

agggatccgc tttgaacctc agggnggcca gaggtttac                           339


<210> SEQ ID NO 52
<211> LENGTH: 453
<212> TYPE: DNA
<213> ORGANISM: Homo sapiens
<220> FEATURE:
<221> NAME/KEY: misc_feature
<222> LOCATION: (453)..(453)
<223> OTHER INFORMATION: n is a, c, g, or t

<400> SEQUENCE: 52

ggtggggggg gggggtgttt aaaaaatccc tcaaatataa caatgaagca tgcttttcta     60

acacaaagag taccaaaatg aatgtgctac tttctgttaa agttttattt ccagagcttg    120

cccaagcaag aatctacttg ccctgtaaaa ttctgcttat acagaattaa aactccttta    180

ttatcccaca aatacattat atatttccat agctttcttt agcccataca cttcttctta    240

agtgttcaac tttcaaatct ctgataaaat gaaactcatc atgaagacca gtcaaaatgc    300

taaaggaaac cttccttaat ctactttgca attactgttc ctttcagtta ctccctacct    360

gcgcctgcca tgaatttttg tttttgtgtt ggtctattct ggactagtgg gctctacaat    420

gagggatgcg tatctggaat accgagagct ttn                                 453


<210> SEQ ID NO 53
<211> LENGTH: 1051
<212> TYPE: DNA
<213> ORGANISM: Homo sapiens

<400> SEQUENCE: 53

ggaccgccgc ctggttaaag gcgcttattt cccaggcagc cgctgcagtc gccacacctt     60

tgcccctgct gcgatgaccc tgtcgccact tctgctgttc ctgccaccgc tgctgctgct    120

gctggacgtc cccacggcgg cggtgcaggc gtcccctctg caagcgttag acttctttgg    180

gaatgggcca ccagttaact acaagacagg caatctatac ctgcgggggc ccctgaagaa    240

gtccaatgca ccgcttgtca atgtgaccct ctactatgaa gcactgtgcg gtggctgccg    300

agccttcctg atccgggagc tcttcccaac atggctgttg gtcatggaga tcctcaatgt    360

cacgctggtg ccctacggaa acgcacagga acaaaatgtc agtggcaggt gggagttcaa    420

gtgccagcat ggagaagagg agtgcaaatt caacaaggtg gaggcctgcg tgttggatga    480

acttgacatg gagctagcct tcctgaccat tgtctgcatg gaagagtttg aggacatgga    540

gagaagtctg ccactatgcc tgcagctcta cgccccaggg ctgtcgccag acactatcat    600

ggagtgtgca atgggggacc gcggcatgca gctcatgcac gccaacgccc agcggacaga    660

tgctctccag ccaccacacg agtatgtgcc ctgggtcacc gtcaatggga aacccttgga    720

agatcagacc cagctcctta cccttgtctg ccagttgtac cagggcaaga agccggatgt    780

ctgcccttcc tcaaccagct ccctcaggag tgtttgcttc aagtgatggc cggtgagctg    840

cggagagctc atggaaggcg agtgggaacc cggctgcctg ccttttttc tgatccagac     900

cctcggcacc tgctacttac caactggaaa attttatgca tcccatgaag cccagataca    960

caaaattcca ccccatgatc aagaatcctg ctccactaag aatggtgcta aagtaaaact   1020
```

```
agtttaataa gcaaaaaaaa aaaaaaaaaa a                                    1051


<210> SEQ ID NO 54
<211> LENGTH: 340
<212> TYPE: DNA
<213> ORGANISM: Homo sapiens
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t

<400> SEQUENCE: 54

ggcacgagca taccccattt ttgagctttc tttgagggcc aactttttnc tctaaaacca     60

gccagggcat gcttttccct caccagctct ganttcttcc aggctaggca actggaaaag    120

cctggnctta gaaactgctt tnttggctta cggcccagct gagctgacca aaatagccaa    180

gagaaagact gtttgcacag tgtgaaattc ctccagggga aataccatag ncaaaaagcc    240

aaganagcca gnacccacgn atggncaggg aacccacagg gcaaaaaaag gccgagttac    300

ccccaaggnc cggggtttgt gggagatggg aggcctaggt                          340


<210> SEQ ID NO 55
<211> LENGTH: 1760
<212> TYPE: DNA
<213> ORGANISM: Homo sapiens

<400> SEQUENCE: 55

atttctttat aaaccacaac tctgggcccg caatggcagt ccactgcctt gctgcagtca     60

cagaatggaa atctgcagag gcctccgcag tcacctaatc actctcctcc tcttcctgtt    120

ccattcagag acgatctgcc gaccctctgg gagaaaatcc agcaagatgc aagccttcag    180

aatctgggat gttaaccaga agaccttcta tctgaggaac aaccaactag ttgctggata    240

cttgcaagga ccaaatgtca atttagaaga aaagatagat gtggtaccca ttgagcctca    300
```

```
tgctctgttc ttgggaatcc atggagggaa gatgtgcctg tcctgtgtca agtctggtga     360

tgagaccaga ctccagctgg aggcagttaa catcactgac ctgagcgaga acagaaagca     420

ggacaagcgc ttcgccttca tccgctcaga cagcggcccc accaccagtt ttgagtctgc     480

cgcctgcccc ggttggttcc tctgcacagc gatggaagct gaccagcccg tcagcctcac     540

caatatgcct gacgaaggcg tcatggtcac caaattctac ttccaggagg acgagtagta     600

ctgcccaggc ctgcctgttc ccattcttgc atggcaagga ctgcagggac tgccagtccc     660

cctgccccag ggctcccggc tatgggggca ctgaggacca gccattgagg ggtggaccct     720

cagaaggcgt cacaagaacc tggtcacagg actctgcctc ctcttcaact gaccagcctc     780

catgctgcct ccagaatggt ctttctaatg tgtgaatcag agcacagcag cccctgcaca     840

aagcccttcc atgtcgcctc tgcattcagg atcaaacccc gaccacctgc ccaacctgct     900

ctcctcttgc cactgcctct tcctccctca ttccaccttc ccatgccctg gatccatcag     960

gccacttgat gacccccaac caagtggctc ccacaccctg ttttacaaaa aagaaaagac    1020

cagtccatga gggaggtttt taagggtttg tggaaaatga aaattaggat ttcatgattt    1080

tttttttca gtccccgtga aggagagccc ttcatttgga gattatgttc tttcggggag    1140

aggctgagga cttaaaatat tcctgcattt gtgaaatgat ggtgaaagta agtggtagct    1200

tttcccttct ttttcttctt tttttgtgat gtcccaactt gtaaaaatta aaagttatgg    1260

tactatgtta gccccataat ttttttttc cttttaaaac acttccataa tctggactcc    1320

tctgtccagg cactgctgcc cagcctccaa gctccatctc cactccagat tttttacagc    1380

tgcctgcagt actttacctc ctatcagaag tttctcagct cccaaggctc tgagcaaatg    1440

tggctcctgg gggttctttc ttcctctgct gaaggaataa attgctcctt gacattgtag    1500

agcttctggc acttggagac ttgtatgaaa gatggctgtg cctctgcctg tctcccccac    1560

cgggctggga gctctgcaga gcaggaaaca tgactcgtat atgtctcagg tccctgcagg    1620

gccaagcacc tagcctcgct cttggcaggt actcagcgaa tgaatgctgt atatgttggg    1680

tgcaaagttc cctacttcct gtgacttcag ctctgtttta caataaaatc ttgaaaatgc    1740

ctaaaaaaaa aaaaaaaaaa                                                1760
```

<210> SEQ ID NO 56
<211> LENGTH: 584
<212> TYPE: DNA
<213> ORGANISM: Homo sapiens

<400> SEQUENCE: 56

```
cacctgcacc ccgcccgggc atagcaccat gcctgcttgt cgcctaggcc cgctagccgc      60

cgccctcctc ctcagcctgc tgctgttcgg cttcacccta gtctcaggca caggagcaga     120

gaagactggc gtgtgccccg agctccaggc tgaccagaac tgcacgcaag agtgcgtctc     180

ggacagcgaa tgcgccgaca acctcaagtg ctgcagcgcg ggctgtgcca ccttctgcct     240

tctctgccca aatgataagg agggttcctg cccccaggtg aacattaact ttccccagct     300

cggcctctgt cgggaccagt gccaggtgga cagccagtgt cctggccaga tgaaatgctg     360

ccgcaatggc tgtgggaagg tgtcctgtgt cactcccaat ttctgaggtc cagccaccac     420

caggctgagc agtgaggaga gaaagtttct gcctggccct gcatctggtt ccagcccacc     480

tgccctcccc tttttcggga ctctgtattc cctcttgggc tgaccacagc ttctcccttt     540

cccaaccaat aaagtaacca ctttcagcaa aaaaaaaaaa aaaa                     584
```

<210> SEQ ID NO 57

<211> LENGTH: 1330
<212> TYPE: DNA
<213> ORGANISM: Homo sapiens

<400> SEQUENCE: 57

```
gcagcccagc caagcactgt caggaatcct gtgaagcagc tccagctatg tgtgaagaag     60
aggacagcac tgccttggtg tgtgacaatg gctctgggct ctgtaaggcc ggctttgctg    120
gggacgatgc tcccagggct gttttcccat ccattgtggg acgtcccaga catcaggggg    180
tgatggtggg aatgggacaa aaagacagct acgtgggtga cgaagcacag agcaaaagag    240
gaatcctgac cctgaagtac ccgatagaac atggcatcat caccaactgg gacgacatgg    300
aaaagatctg gcaccactct ttctacaatg agcttcgtgt tgcccctgaa gagcatccca    360
ccctgctcac ggaggcaccc ctgaacccca aggccaaccg ggagaaaatg actcaaatta    420
tgtttgagac tttcaatgtc ccagccatgt atgtggctat ccaggcggtg ctgtctctct    480
atgcctctgg acgcacaact ggcatcgtgc tggactctgg agatggtgtc acccacaatg    540
tccccatcta tgagggctat gccttgcccc atgccatcat gcgtctggat ctggctggcc    600
gagatctcac tgactacctc atgaagatcc tgactgagcg tggctattcc ttcgttacta    660
ctgctgagcg tgagattgtc cgggacatca aggagaaact gtgttatgta gctctggact    720
ttgaaaatga gatggccact gccgcatcct catcctccct tgagaagagt tacgagttgc    780
ctgatgggca agtgatcacc atcggaaatg aacgtttccg ctgcccagag accctgttcc    840
agccatcctt catcgggatg gagtctgctg gcatccatga aaccacctac aacagcatca    900
tgaagtgtga tattgacatc aggaaggacc tctatgctaa caatgtccta tcaggggggca   960
ccactatgta ccctggcatt gccgaccgaa tgcagaagga gatcacggcc ctagcaccca   1020
gcaccatgaa gatcaagatc attgcccctc cggagcgcaa atactctgtc tggatcggtg   1080
gctccatcct ggcctctctg tccaccttcc agcagatgtg gatcagcaaa caggaatacg   1140
atgaagccgg gccttccatt gtccaccgca aatgcttcta aaacactttc ctgctcctct   1200
ctgtctctag cacacaactg tgaatgtcct gtggaattat gccttcagtt cttttccaaa   1260
tcattcctag ccaaagctct gactcgttac ctatgtgttt tttaataaat ctgaaatagg   1320
ctactggtaa                                                          1330
```

<210> SEQ ID NO 58
<211> LENGTH: 2743
<212> TYPE: DNA
<213> ORGANISM: Homo sapiens

<400> SEQUENCE: 58

```
gcgggccgtt atccatttgt gttgttcgcc agctaggcct ggcctcgtcc cgcttcgctc     60
ggtcggtctc gcgcgccccc atagccttgc tagagggtta gcgttagcct taagtgtgcg    120
aatccgagga gcagcgacag actcgagacc acgctccttc ctcgggaagg aggcggcacc    180
tcgcgtttga ggcccgcctg cgtttgaggc ccgcctgcgc ttgcggcccg cctgcgcttg    240
aggcctgtct gcgtttgaga tctcattggg cgtgattgag gaatttgggg aggtttttgg    300
gcggtattga ggacgagggg gtccgttagt cagcatagaa tcctggagcg ggaatccctc    360
accgtctaaa tggcgtcggg ggcgggacct ccgggatctg gcttccgcgg gccgccgccg    420
gccctgaaac gtgagggata gctgagatga ggcagctact gggatggccc ccatgcgcat    480
ttacatgcag tccgactgcc gagctttcga ggcagcagga tttaccgtcc acattcctca    540
ctactaacca agcttttaga acagatctca caagaaccta gaggtcggta tttttcgat     600
```

```
ttaaatttgc ctgttactga cgttaacgtc tttcgcctag tgagcagtag ccaacatgtc     660
agggtgggag tcatattaca aaaccgaggg cgatgaagaa gcagaggaag aacaagaaga     720
gaaccttgaa gcaagtggag actataaata ttcaggaaga gatagtttga ttttttttggt     780
tgatgcctcc aaggctatgt ttgaatctca gagtgaagat gagttgacac cttttgacat     840
gagcatccag tgtatccaaa gtgtgtacat cagtaagatc ataagcagtg atcgagatct     900
cttggctgtg gtgttctatg gtaccgagaa agacaaaaat tcagtgaatt ttaaaaatat     960
ttacgtctta caggagctgg ataatccagg tgcaaaacga attctagagc ttgaccagtt    1020
taaggggcag cagggacaaa aacgtttcca agacatgatg ggccacggat ctgactactc    1080
actcagtgaa gtgctgtggg tctgtgccaa cctctttagt gatgtccaat tcaagatgag    1140
tcataagagg atcatgctgt tcaccaatga agacaacccc catggcaatg acagtgccaa    1200
agccagccgg gccaggacca aagccggtga tctccgagat acaggcatct tccttgactt    1260
gatgcacctg aagaaacctg gggggctttga catatccttg ttctacagag atatcatcag    1320
catagcagag gatgaggacc tcagggttca ctttgaggaa tccagcaagc tagaagacct    1380
gttgcggaag gttcgcgcca aggagaccag gaagcgagca ctcagcaggt taaagctgaa    1440
gctcaacaaa gatatagtga tctctgtggg catttataat ctggtccaga aggctctcaa    1500
gcctcctcca ataaagctct atcgggaaac aaatgaacca gtgaaaacca agacccggac    1560
ctttaataca agtacaggcg gtttgcttct gcctagcgat accaagaggt ctcagatcta    1620
tgggagtcgt cagattatac tggagaaaga ggaaacagaa gagctaaaac ggtttgatga    1680
tccaggtttg atgctcatgg gtttcaagcc gttggtactg ctgaagaaac accattacct    1740
gaggccctcc ctgttcgtgt acccagagga gtcgctggtg attgggagct caaccctgtt    1800
cagtgctctg ctcatcaagt gtctggagaa ggaggttgca gcattgtgca gatacacacc    1860
ccgcaggaac atccctcctt attttgtggc tttggtgcca caggaagaag agttggatga    1920
ccagaaaatt caggtgactc ctccaggctt ccagctggtc tttttaccct ttgctgatga    1980
taaaaggaag atgcccttta ctgaaaaaat catggcaact ccagagcagg tgggcaagat    2040
gaaggctatc gttgagaagc ttcgcttcac atacagaagt gacagctttg agaaccccgt    2100
gctgcagcag cacttcagga acctggaggc cttggccttg gatttgatgg agccggaaca    2160
agcagtggac ctgacattgc ccaaggttga agcaatgaat aaaagactgg gctccttggt    2220
ggatgagttt aaggagcttg tttacccacc agattacaat cctgaaggga aagttaccaa    2280
gagaaaacac gataatgaag gttctggaag caaaaggccc aaggtggagt attcagaaga    2340
ggagctgaag acccacatca gcaagggtac gctgggcaag ttcactgtgc ccatgctgaa    2400
agaggcctgc cgggcttacg ggctgaagag tggtctgaag aagcaggagc tgctggaagc    2460
cctcaccaag cacttccagg actgaccaga ggccgcgcgt ccagctgccc ttccgcagtg    2520
tggccaggct gcctggcctt gtcctcagcc agttaaaatg tgtttctcct gagctaggaa    2580
gagtctaccc gacataagtc gagggacttt atgtttttga ggctttctgt tgccatggtg    2640
atggtgtagc cctcccactt tgctgttctt tactttactg cctgaataaa gagccctaag    2700
tttgtactaa aaaaaaaaaa aaaaaaaaaa aaaaaaaaaa aaa                      2743
```

<210> SEQ ID NO 59
<211> LENGTH: 1826
<212> TYPE: DNA
<213> ORGANISM: Homo sapiens

<400> SEQUENCE: 59

```
agtatgtgtg gttggggaat tcatgtggag gtcagagtgg aagcaggtgt gagagggtcc     60

agcagaagga aacatggctg ccaaagtgtt tgagtccatt ggcaagtttg gcctggcctt    120

agctgttgca ggaggcgtgg tgaactctgc cttatataat gtggatgctg ggcacagagc    180

tgtcatcttt gaccgattcc gtggagtgca ggacattgtg gtaggggaag ggactcattt    240

tctcatcccg tgggtacaga aaccaattat ctttgactgc cgttctcgac cacgtaatgt    300

gccagtcatc actggtagca aagatttaca gaatgtcaac atcacactgc gcatcctctt    360

ccggcctgtc gccagccagc ttcctcgcat cttcaccagc atcggagagg actatgatga    420

gcgtgtgctg ccgtccatca caactgagat cctcaagtca gtggtggctc gctttgatgc    480

tggagaacta atcacccaga gagagctggt ctccaggcag gtgagcgacg accttacaga    540

gcgagccgcc acctttgggc tcatcctgga tgacgtgtcc ttgacacatc tgaccttcgg    600

gaaggagttc acagaagcgg tggaagccaa acaggtggct cagcaggaag cagagagggc    660

cagatttgtg gtggaaaagg ctgagcaaca gaaaaaggcg gccatcatct ctgctgaggg    720

cgactccaag gcagctgagc tgattgccaa ctcactggcc actgcagggg atggcctgat    780

cgagctgcgc aagctggaag ctgcagagga catcgcgtac cagctctcac gctctcggaa    840

catcacctac ctgccagcgg ggcagtccgt gctcctccag ctgccccagt gagggcccac    900

cctgcctgca cctccgcggg ctgactgggc cacagccccg atgattctta acacagcctt    960

ccttctgctc ccaccccaga aatcactgtg aaatttcatg attggcttaa agtgaaggaa   1020

ataaaggtaa aatcacttca gatctctaat tagtctatca aatgaaactc tttcattctt   1080

ctcacatcca tctacttttt tatccacctc cctaccaaaa attgccaagt gcctatgcaa   1140

accagcttta ggtcccaatt cggggcctgc tggagttccg gcctgggcac cagcatttgg   1200

cagcacgcag gcggggcagt atgtgatgga ctggggagca caggtgtctg cctagatcca   1260

cgtgtggcct ccgtcctgtc actgatggaa ggtttgcgga tgagggcatg tgcggctgaa   1320

ctgagaaggc aggcctccgt cttcccagcg gttcctgtgc agatgctgct gaagagaggt   1380

gccggggagg ggcagagagg aagtggtctg tctgttacca taagtctgat tctctttaac   1440

tgtgtgacca gcggaaacag gtgtgtgtga actgggcaca gattgaagaa tctgcccctg   1500

ttgaggtggg tgggcctgac tgttgccccc cagggtccta aaacttggat ggacttgtat   1560

agtgagagag gaggcctgga ccgagatgtg agtcctgttg aagacttcct ctctaccccc   1620

caccttggtc cctctcagat acccagtgga attccaactt gaaggattgc atcctgctgg   1680

ggctgaacat gcctgccaaa gacgtgtccg acctacgttc ctggccccct cgttcagaga   1740

ctgcccttct cacgggctct atgcctgcac tgggaaggaa acaaatgtgt ataaactgct   1800

gtcaataaat gacacccaga ccttcc                                        1826
```

<210> SEQ ID NO 60
<211> LENGTH: 4322
<212> TYPE: DNA
<213> ORGANISM: Homo sapiens

<400> SEQUENCE: 60

```
cccccagagg cgccggagcc cggaatcccg ctcggagcca gccagccgtc ccgagctacc     60

agcaggtttc attgaaaaca gatcctgcaa aagttccagg tgcccacact ggaaacttgg    120

agatcctgct tcccagacca cagctgtggg gaacttgggg tggagcagag aagtttctgt    180

attcagctgc ccaggcagag gagaatgggg tctccacagc ctgaagaatg aagacacgac    240

agaataaaga ctcgatgtca atgaggagtg gacggaagaa agaggcccct gggccccggg    300
```

-continued

```
aagaactgag atcgaggggc cgggcctccc ctggaggggt cagcacgtcc agcagtgatg    360
gcaaagctga gaagtccagg cagacagcca agaaggcccg agtagaggaa gcctccaccc    420
caaaggtcaa caagcagggt cggagtgagg agatctcaga gagtgaaagt gaggagacca    480
atgcaccaaa aaagaccaaa actgaggaac tccctcggcc acagtctccc tccgatctgg    540
atagcttgga cgggcggagc cttaatgatg atggcagcag cgaccctagg gatatcgacc    600
aggacaaccg aagcacgtcc cccagtatct acagccctgg aagtgtggag aatgactctg    660
actcatcttc tggcctgtcc cagggcccag cccgccccta ccacccacct ccactctttc    720
ctccttcccc tcaaccgcca gacagcaccc ctcgacagcc agaggctagc tttgaacccc    780
atccttctgt gacacccact ggatatcatg ctcccatgga gcccccccaca tctcgaatgt    840
tccaggctcc tcctggggcc cctccccctc acccacagct ctatcccggg ggcactggtg    900
gagttttgtc tggaccccca atgggtccca agggggggagg ggctgcctca tcagtggggg    960
gccctaatgg gggtaagcag cacccccccac ccactactcc catttcagta tcaagctctg   1020
gggctagtgg tgctcccccca acaaagccgc ctaccactcc agtgggtggt gggaacctac   1080
cttctgctcc accaccagcc aacttccccc atgtgacacc gaacctgcct cccccacctg   1140
ccctgagacc cctcaacaat gcatcagcct ctccccctgg cctgggggcc caaccactac   1200
ctggtcatct gccctctccc cacgccatgg gacagggtat cggtggactt cctcctggcc   1260
cagagaaggg cccaactctg gctccttcac cccactctct gcctcctgct tcctcttctg   1320
ctccagcgcc ccccatgagg tttccttatt catcctctag tagtagctct gcagcagcct   1380
cctcttccag ttcttcctcc tcttcctctg cctccccctt cccagcttcc caggcattgc   1440
ccagctaccc ccactctttc cctcccccaa caagcctctc tgtctccaat cagcccccca   1500
agtatactca gccttctctc ccatcccagg ctgtgtggag ccagggtccc ccaccacctc   1560
ctccctatgg ccgcctctta gccaacagca atgcccatcc aggcccccttc cctccctcta   1620
ctggggccca gtccaccgcc cacccaccag tctcaacaca tcaccatcac caccagcaac   1680
agcaacagca gcagcagcag cagcagcagc agcagcatca cggaaactct gggcccccctc   1740
ctcctggagc atttccccac ccactggagg gcggtagctc ccaccacgca cacccttacg   1800
ccatgtctcc ctccctgggg tctctgaggc cctacccacc agggccagca cacctgcccc   1860
cacctcacag ccaggtgtcc tacagccaag caggccccaa tggccctcca gtctcttcct   1920
cttccaactc ttcctcttcc acttctcaag ggtcctaccc atgttcacac ccctcccctt   1980
cccagggccc tcaaggggcg ccctaccctt tcccaccggt gcctacggtc accacctctt   2040
cggctaccct ttccacggtc attgccaccg tggcttcctc gccagcaggc tacaaaacgg   2100
cctccccacc tgggccccca ccgtacggaa agagagcccc gtccccgggg gcctacaaga   2160
cagccacccc acccggatac aaacccgggt cgcctccctc cttccgaacg gggaccccac   2220
cgggctatcg aggaacctcg ccacctgcag gcccagggac cttcaagccg ggctcgccca   2280
ccgtgggacc tgggcccctg ccacctgcgg ggccctcagg cctgccatcg ctgccaccac   2340
cacctgcggc ccctgcctca gggccgcccc tgagcgccac gcagatcaaa caggagccgg   2400
ctgaggagta tgagaccccc gagagcccgg tgccccccagc ccgcagcccc tcgccccctc   2460
ccaaggtggt agatgtaccc agccatgcca gtcagtctgc caggttcaac aaacacctgg   2520
atcgcggctt caactcgtgc gcgcgcagcg acctgtactt cgtgccactg gagggctcca   2580
agctggccaa gaagcgggcc gacctggtgg agaaggtgcg gcgcgaggcc gagcagcgcg   2640
cgcgcgaaga aaaggagcgc gagcgcgagc gggaacgcga gaaagagcgc gagcgcgaga   2700
```

```
aggagcgcga gcttgaacgc agcgtgaagt tggctcagga gggccgtgct ccggtggaat   2760
gcccatctct gggcccagtg ccccatcgcc ctccatttga accgggcagt gcggtggcta   2820
cagtgccccc ctacctgggt cctgacactc cagccttgcg cactctcagt gaatatgccc   2880
ggcctcatgt catgtctcct ggcaatcgca accatccatt ctacgtgccc ctgggggcag   2940
tggacccggg gctcctgggt tacaatgtcc cggccctgta cagcagtgat ccagctgccc   3000
gggagaggga acgggaagcc cgtgaacgag acctccgtga ccgcctcaag cctggctttg   3060
aggtgaagcc tagtgagctg gaacccctac atggggtccc tgggccgggc ttggatccct   3120
ttccccgaca tgggggcctg gctctgcagc ctggcccacc tggcctgcac cctttcccct   3180
ttcatccgag cctggggccc ctggagcgag aacgtctagc gctggcagct gggccagccc   3240
tgcggcctga catgtcctat gctgagcggc tggcagctga gaggcagcac gcagaaaggg   3300
tggcggccct gggcaatgac ccactggccc ggctgcagat gctcaatgtg actccccatc   3360
accaccagca ctcccacatc cactcgcacc tgcacctgca ccagcaagat gctatccatg   3420
cagcctctgc ctcggtgcac cctctcattg acccccctggc ctcagggtct caccttaccc   3480
ggatccccta cccagctgga actctcccta acccccctgct tcctcaccct ctgcacgaga   3540
acgaagttct tcgtcaccag ctctttgctg cccccttaccg ggacctgccg gcctcccttt   3600
ctgccccgat gtcagcagct catcagctgc aggccatgca cgcacagtca gctgagctgc   3660
agcgcttggc gctggaacag cagcagtggc tgcatgccca tcacccgctg cacagtgtgc   3720
cgctgcctgc ccaggaggac tactacagtc acctgaagaa ggaaagcgac aagccactgt   3780
agaacctgcg atcaagagag caccatggct cctacattgg accttggagc acccccaccc   3840
tccccccacc gtgcccttgg cctgccaccc agagccaaga gggtgctgct cagttgcagg   3900
gcctccgcag ctggacagag agtgggggag ggagggacag acagaaggcc aaggcccgat   3960
gtggtgtgca gaggtgggga ggtggcgagg atggggacag aaagcgcaca gaatcttgga   4020
ccaggtctct cttccttgtc ccccctgctt ttctcctccc ccatgcccaa cccctgtggc   4080
cgccgcccct cccctgcccc gttggtgtga ttatttcatc tgttagatgt ggctgttttg   4140
cgtagcatcg tgtgccaccc ctgcccctcc ccgatccctg tgtgcgcgcc ccctctgcaa   4200
tgtatgcccc ttgccccttc cccacactaa taatttatat atataaatat ctatatgacg   4260
ctcttaaaaa aacatcccaa ccaaaaccaa ccaaacaaaa acatcctcac aactccccag   4320
ga                                                                  4322
```

<210> SEQ ID NO 61
<211> LENGTH: 3088
<212> TYPE: DNA
<213> ORGANISM: Homo sapiens

<400> SEQUENCE: 61

```
acaaaaaagc ttttacgagg tatcagcact tttctttcat tagggggaag gcgtgaggaa     60
agtaccaaac agcagcggag ttttaaactt taaatagaca ggtctgagtg cctgaacttg    120
ccttttcatt ttacttcatc ctccaaggag ttcaatcact tggcgtgact tcactacttt    180
taagcaaaag agtggtgccc aggcaacatg ggtgactgga gcgccttagg caaactcctt    240
gacaaggttc aagcctactc aactgctgga gggaaggtgt ggctgtcagt acttttcatt    300
ttccgaatcc tgctgctggg gacagcggtt gagtcagcct ggggagatga gcagtctgcc    360
tttcgttgta acactcagca acctggttgt gaaaatgtct gctatgacaa gtctttccca    420
atctctcatg tgcgcttctg ggtcctgcag atcatatttg tgtctgtacc cacactcttg    480
```

-continued

```
tacctggctc atgtgttcta tgtgatgcga aaggaagaga aactgaacaa gaaagaggaa    540
gaactcaagg ttgcccaaac tgatggtgtc aatgtggaca tgcacttgaa gcagattgag    600
ataaagaagt tcaagtacgg tattgaagag catggtaagg tgaaaatgcg aggggggttg    660
ctgcgaacct acatcatcag tatcctcttc aagtctatct ttgaggtggc cttcttgctg    720
atccagtggt acatctatgg attcagcttg agtgctgttt acacttgcaa aagagatccc    780
tgcccacatc aggtggactg tttcctctct cgccccacgg agaaaaccat cttcatcatc    840
ttcatgctgg tggtgtcctt ggtgtccctg gccttgaata tcattgaact cttctatgtt    900
ttcttcaagg gcgttaagga tcgggttaag ggaaagagcg acccttacca tgcgaccagt    960
ggtgcgctga gccctgccaa agactgtggg tctcaaaaat atgcttattt caatggctgc   1020
tcctcaccaa ccgctcccct ctcgcctatg tctcctcctg ggtacaagct ggttactggc   1080
gacagaaaca attcttcttg ccgcaattac aacaagcaag caagtgagca aaactgggct   1140
aattacagtg cagaacaaaa tcgaatgggg caggcgggaa gcaccatctc taactcccat   1200
gcacagcctt ttgatttccc cgatgataac cagaattcta aaaaactagc tgctggacat   1260
gaattacagc cactagccat tgtggaccag cgaccttcaa gcagagccag cagtcgtgcc   1320
agcagcagac ctcggcctga tgacctggag atctagatac aggcttgaaa gcatcaagat   1380
tccactcaat tgtggagaag aaaaaaggtg ctgtagaaag tgcaccaggt gttaattttg   1440
atccggtgga ggtggtactc aacagcctta ttcatgaggc ttagaaaaca caaagacatt   1500
agaataccta ggttcactgg gggtgtatgg ggtagatggg tggagaggga ggggataaga   1560
gaggtgcatg ttggtattta aagtagtgga ttcaaagaac ttagattata aataagagtt   1620
ccattaggtg atacatagat aagggctttt tctccccgca aacaccccta agaatggttc   1680
tgtgtatgtg aatgagcggg tggtaattgt ggctaaatat ttttgtttta ccaagaaact   1740
gaaataattc tggccaggaa taaatacttc ctgaacatct taggtctttt caacaagaaa   1800
aagacagagg attgtcctta agtccctgct aaaacattcc attgttaaaa tttgcacttt   1860
gaaggtaagc tttctaggcc tgaccctcca ggtgtcaatg gacttgtgct actatatttt   1920
tttattcttg gtatcagttt aaaattcaga caaggcccac agaataagat tttccatgca   1980
tttgcaaata cgtatattct ttttccatcc acttgcacaa tatcattacc atcacttttt   2040
catcattcct cagctactac tcacattcat ttaatggttt ctgtaaacat ttttaagaca   2100
gttgggatgt cacttaacat tttttttttt tgagctaaag tcagggaatc aagccatgct   2160
taatatttaa caatcactta tatgtgtgtc gaagagtttg ttttgtttgt catgtattgg   2220
tacaagcaga tacagtataa actcacaaac acagatttga aaataatgca catatggtgt   2280
tcaaatttga acctttctca tggatttttg tggtgtgggc caatatggtg tttacattat   2340
ataattcctg ctgtggcaag taaagcacac tttttttttc tcctaaaatg tttttccctg   2400
tgtatcctat tatggatact ggttttgtta attatgattc tttattttct ctccttttttt   2460
taggatatag cagtaatgct attactgaaa tgaatttcct ttttctgaaa tgtaatcatt   2520
gatgcttgaa tgatagaatt ttagtactgt aaacaggctt tagtcattaa tgtgagagac   2580
ttagaaaaaa tgcttagagt ggactattaa atgtgcctaa atgaattttg cagtaactgg   2640
tattcttggg ttttcctact taatacacag taattcagaa cttgtattct attatgagtt   2700
tagcagtctt ttggagtgac cagcaacttt gatgtttgca ctaagatttt atttggaatg   2760
caagagaggt tgaaagagga ttcagtagta cacatacaac taatttattt gaactatatg   2820
ttgaagacat ctaccagttt ctccaaatgc cttttttaaa actcatcaca gaagattggt   2880
```

gaaaatgctg agtatgacac ttttcttctt gcatgcatgt cagctacata aacagttttg 2940
tacaatgaaa attactaatt tgtttgacat tccatgttaa actacggtca tgttcagctt 3000
cattgcatgt aatgtagacc tagtccatca gatcatgtgt tctggagagt gttctttatt 3060
caataaagtt ttaatttagt ataaacat 3088

<210> SEQ ID NO 62
<211> LENGTH: 2828
<212> TYPE: DNA
<213> ORGANISM: Homo sapiens

<400> SEQUENCE: 62
gcgctacggc ggacccggct gggcagttcc ttccccagaa ggagagattc ctctgccatg 60
gagtcctacg atgtgatcgc caaccagcct gtcgtgatcg acaacggatc cggtgtgatt 120
aaagctggtt ttgctggtga tcagatcccc aaatactgct ttccaaacta tgtgggccga 180
cccaagcacg ttcgtgtcat ggcaggagcc cttgaaggcg acatcttcat tggccccaaa 240
gctgaggagc accgagggct gctttcaatc cgctatccca tggagcatgg catcgtcaag 300
gattggaacg acatggaacg catttggcaa tatgtctatt ctaaggacca gctgcagact 360
ttctcagagg agcatcctgt gctcctgact gaggcgcctt taaacccacg aaaaaaccgg 420
gaacgagctg ccgaagtttt cttcgagacc ttcaatgtgc ccgctctttt catctccatg 480
caagctgtac tcagccttta cgctacaggc aggaccacag ggtggtgct ggattctggg 540 gatggagtca cccatgctgt gcccatctat gagggctttg ccatgcccca ctccatcatg 600
cgcatcgaca tcgcgggccg ggacgtctct cgcttcctgc gcctctacct gcgtaaggag 660
ggctacgact tccactcatc ctctgagttt gagattgtca aggccataaa agaaagagcc 720
tgttacctat ccataaaccc ccaaaaggat gagacgctag agacagagaa agctcagtac 780
tacctgcctg atggcagcac cattgagatt ggtccttccc gattccgggc ccctgagttg 840
ctcttcaggc cagatttgat tggagaggag agtgaaggca tccacgaggt cctggtgttc 900
gccattcaga agtcagacat ggacctgcgg cgcacgcttt tctctaacat tgtcctctca 960
ggaggctcta ccctgttcaa aggttttggt gacaggctcc tgagtgaagt gaagaaacta 1020
gctccaaaag atgtgaagat caggatatct gcacctcagg agagactgta ttccacgtgg 1080
attgggggct ccatccttgc ctccctggac acctttaaga agatgtgggt ctccaaaaag 1140
gaatatgagg aagacggtgc ccgatccatc cacagaaaaa ccttctaatg tcgggacatc 1200
atcttcacct ctctctgaag ttaactccac tttaaaactc gctttcttga gtcggagtgt 1260
ttgcgaggaa ctgcctgtgt gtgagtgcgt gtgtggatat gagtgtgtgc gcacatgcga 1320
gtgccgtgtg gccctgggac cctgggccca gaaaggacga tgaactaccc gcagtggtga 1380
tgcctgaggc ctggggttga ccactaactg gctcctgaca gggaagagcg ctggcagagg 1440
ctgtgctccc tcctcaggtg gcctctggct ggctgtgggg gactccgttt actaccacag 1500
ggagacagag ggaggtaagc catcccccgg gagaccttgc tgctgaccat cctaggctgg 1560
gctggcccac cctcaccccc acccccaggg tgccctgagg ccccaggcag ctgctgcctc 1620
cactatcgat gcctcctgac tgcacactga ggactgggac tggggttgag ttctgtctgg 1680
ttttgttgcc attttggttt gggaggctgg aaaagcaccc caagaagcta ttacagagac 1740
tggagtcagg agagagcagg aggccctcat gttcaccagg gaacaggacc acaccggcca 1800
ctgaaggagg gcaggagcag tcctccctct gaatggctgc agagttaatg ttcccagccc 1860
agtccccttt cgggggcctt gggagagttt aaggcacctg ctggttccag gacctcgctt 1920

```
tccatctgtt cttgttgcaa tgccatcttc aaaccgtttt atttattgaa gtgtttgttc   1980

agttaggggc tggagagagg gagcttgctg cctcctgcct tgctacacta atgtttacag   2040

cacctaagct tagcctccag ggccccacct ctcccagctg atggtgagct gacagtgtcc   2100

acaggttcca ggaccatttg agattggaag ctacactcaa agacactccc accaggctct   2160

ttctcccttt tcctcttctc actgccctgg aatcaacagg ctggttgctg gttagatttt   2220

ctgaaacagg aggtaaaatt tttctttggc agaggcccct aagcaaggga ggggtgttgg   2280

agagccagtg cccttaagac tggagaaagc tgcaatttac caagttgcct tttgccactg   2340

tagctgacca ggggactagg ttgtagaggt gggaaggccc ctctgggctg atcttgtgcc   2400

attcttgacc ttggacctgc ttggttaagg agggagtggg ccagaccaga gtgccaggag   2460

ctaatggagc caggcctgac acctaggagt ggtccaaagc cttcagccta gatggtgcaa   2520

agctggggcc agcctgtctt caccggcacc ctcacctgtg acaccaagac ccaccccaat   2580

ccagacttca cacagtattc tcccccacgc cgtctatgac caaaggcccc tgccaggtgt   2640

gggtccacag cagcaggtat gtgtgaaagc aacgtagcgc cccgcggact gcagtgcgct   2700

taaccaactc acctcccttc tcttagccca agcctgtccc tcgcacagcc tcgcacaaac   2760

cacattgcct ggtggggccc agtgtactga aataaagtcg ttccgataga cacgtcaaaa   2820

aaaaaaaa                                                             2828
```

<210> SEQ ID NO 63
<211> LENGTH: 415
<212> TYPE: DNA
<213> ORGANISM: Homo sapiens

<400> SEQUENCE: 63

```
ttttttttat tgctattaag atttttcttt taatatgcca tgagatatct tgattgtata     60

ttttccaaag tactttccag ccacatctcc caacccatcc aaaagacttt gccagtcttt    120

ccaatgcaat aaaagatgct ggattatagt tttgtctacc atttcttttt gaaagcaata    180

ttatactaat gactttaatg gtaatacact cttatctaat aaagaaacac atttacaaat    240

atcagaaacc cagttttgga acaatttgca taaattttga actgaatcag cattttgtgg    300

gtttttttaaa aggcagcagt ttgactcacg acttgctgat aaacacgttt ctgctgaggg   360

aaggggaaaa gacagggaga gtgaatgctg catttctcca ttggccccaa aagtg         415
```

<210> SEQ ID NO 64
<211> LENGTH: 2455
<212> TYPE: DNA
<213> ORGANISM: Homo sapiens

<400> SEQUENCE: 64

```
gaattcgggc gggcttcttc gctgccgacg tacgacgagt ggccgggctc ttgcgtctgg     60

taacgcgctg tctctaacgc cagcgccgtc tcgcgcgcac tgcgcacaga ccacccgcag    120

acgcccggca gtccgcaggc ccaaacgcgc acgcgacccc gctctccgca ccgtacccgg    180

ccgcctcggc atggcgcccc gcagcgcccg gcgacccctg ctgctgctac tgcctgttgc    240

tgctgctcgg cctcatgcat tgtcgtcagc agccatgttt atggtgaaaa atggcaacgg    300

gaccgcgtgc ataatggcca acttctctgc tgccttctca gtgaactacg acaccaagag    360

tggccccaag aacatgacct ttgacctgcc atcagatgcc acagtggtgc tcaaccgcag    420

ctcctgtgga aaagagaaca cttctgaccc cagtctcgtg attgcttttg gaagaggaca    480

tacactcact ctcaatttca cgagaaatgc aacacgttac agcgttcagc tcatgagttt    540
```

```
tgtttataac ttgtcagaca cacacctttt ccccaatgcg agctccaaag aaatcaagac    600
tgtggaatct ataactgaca tcagggcaga tatagataaa aaatacagat gtgttagtgg    660
cacccaggtc cacatgaaca acgtgaccgt aacgctccat gatgccacca tccaggcgta    720
cctttccaac agcagcttca gcaggggaga gacacgctgt gaacaagaca ggccttcccc    780
aaccacagcg ccccctgcgc cacccagccc ctcgccctca cccgtgccca agagcccctc    840
tgtggacaag tacaacgtga gcggcaccaa cgggacctgc ctgctggcca gcatggggct    900
gcagctgaac ctcacctatg agaggaagga caacacgacg gtgacaaggc ttctcaacat    960
caaccccaac aagacctcgg ccagcgggag ctgcggcgcc cacctggtga ctctggagct   1020
gcacagcgag ggcaccaccg tcctgctctt ccagttcggg atgaatgcaa gttctagccg   1080
gtttttccta caaggaatcc agttgaatac aattcttcct gacgccagag accctgcctt   1140
taaagctgcc aacggctccc tgcgagcgct gcaggccaca gtcggcaatt cctacaagtg   1200
caacgcggag gagcacgtcc gtgtcacgaa ggcgttttca gtcaatatat tcaaagtgtg   1260
ggtccaggct ttcaaggtgg aaggtggcca gtttggctct gtggaggagt gtctgctgga   1320
cgagaacagc acgctgatcc ccatcgctgt gggtggtgcc ctggcggggc tggtcctcat   1380
cgtcctcatc gcctacctcg tcggcaggaa gaggagtcac gcaggctacc agactatcta   1440
gcctggtgca cgcaggcaca gcagctgcag gggcctctgt tcctttctct gggcttaggg   1500
tcctgtcgaa ggggaggcac actttctgca aacgtttctc aaatctgctt catccaatgt   1560
gaagttcatc ttgcagcatt tactatgcac aacagagtaa ctatcgaaat gacggtgtta   1620
attttgctaa ctgggttaaa tattttgcta actggttaaa cattaatatt taccaaagta   1680
ggattttgag ggtgggggtg ctctctctga gggggtgggg gtgccgctgt ctctgagggg   1740
tgggggtgcc gctgtctgag ggggtggggg gccgctctct ctgagggggt gggggtgccg   1800
ctttctctga gggggtgggg gtgccgctct ctctgagggg gtgggggtgc tgctctctcc   1860
gaggggtgga atgccgctgt ctctgagggg tgggggtgcc gctctaaatt ggctccatat   1920
cattgagttt agggttctgg tgtttggttt cttcattctt tactgcactc agatttaagc   1980
cttacaaagg gaaacctctg gccgtcacac gtaggacgca tgaaggtcac tcgtgtgagg   2040
ctgacatgct cacacattac aacagtagag agggaaaatc ctaagacaga ggaactccag   2100
agatgagtgt ctggagcggc ttcagttcag ctttaaaggc caggacgcgc gacacgtggc   2160
tggcggcctc gttccagtgg cggcacgtcc ttggcgtctc taatgtctgc agctcaaggg   2220
ctggcacttt tttaaatata aaaatggtgt tatttttatt ttttttgta aagtgatttt   2280
tggtcttctg ttgacattcg ggtgatcctg ttctgcgctg tgtacaatgt gagatcggtg   2340
cgttctcctg atgttttgcc gtggcttggg gattgtacac gggaccagct cacgtaatgc   2400
attgcctgta acaatgtaat aaaaagcctc tttctttcaa aaaaaccccg aattc        2455
```

<210> SEQ ID NO 65
<211> LENGTH: 3583
<212> TYPE: DNA
<213> ORGANISM: Homo sapiens

<400> SEQUENCE: 65

```
cgcggacccg gccggcccag gcccgcgccc gccgcggccc tgagaggccc cggcaggtcc     60
cggcccggcg gcggcagcca tggccggggg gccgggcccg gggggagcccg cagcccccgg    120
cgcccagcac ttcttgtacg aggtgccgcc ctgggtcatg tgccgcttct acaaagtgat    180
ggacgccctg gagcccgccg actggtgcca gttcgccgcc ctgatcgtgc gcgaccagac    240
```

```
cgagctgcgg ctgtgcgagc gctccgggca gcgcacggcc agcgtcctgt ggccctggat    300
caaccgcaac gcccgtgtgg ccgacctcgt gcacatcctc acgcacctgc agctgctccg    360
tgcgcgggac atcatcacag cctggcaccc tcccgccccg cttccgtccc caggcaccac    420
tgccccgagg cccagcagca tccctgcacc cgccgaggcc gaggcctgga gcccccggaa    480
gttgccatcc tcagcctcca ccttcctctc cccagctttt ccaggctccc agacccattc    540
agggcctgag ctcggcctgg ttccaagccc tgcttccctg tggcctccac cgccatctcc    600
agccccttct tctaccaagc caggcccaga gagctcagtg tccctcctgc agggagcccg    660
cccctctccg ttttgctggc cctctgtga gatttcccgg ggcacccaca acttctcgga    720
ggagctcaag atcggggagg gtggctttgg gtgcgtgtac cgggcggtga tgaggaacac    780
ggtgtatgct gtgaagaggc tgaaggagaa cgctgacctg gagtggactg cagtgaagca    840
gagcttcctg accgaggtgg agcagctgtc caggtttcgt cacccaaaca ttgtggactt    900
tgctggctac tgtgctcaga acggcttcta ctgcctggtg tacggcttcc tgcccaacgg    960
ctccctggag gaccgtctcc actgccagac ccaggcctgc ccacctctct cctggcctca   1020
gcgactggac atccttctgg gtacagcccg ggcaattcag tttctacatc aggacagccc   1080
cagcctcatc catggagaca tcaagagttc caacgtcctt ctggatgaga ggctgacacc   1140
caagctggga gactttggcc tggcccggtt cagccgcttt gccgggtcca gccccagcca   1200
gagcagcatg gtggcccgga cacagacagt gcggggcacc ctggcctacc tgcccgagga   1260
gtacatcaag acgggaaggc tggctgtgga cacggacacc ttcagctttg gggtggtagt   1320
gctagagacc ttggctggtc agagggctgt gaagacgcac ggtgccagga ccaagtatct   1380
gaaagacctg gtggaagagg aggctgagga ggctggagtg gctttgagaa gcacccagag   1440
cacactgcaa gcaggtctgg ctgcagatgc ctgggctgct cccatcgcca tgcagatcta   1500
caagaagcac ctggacccca ggcccgggcc ctgcccacct gagctgggcc tgggcctggg   1560
ccagctggcc tgctgctgcc tgcaccgccg ggccaaaagg aggcctccta tgacccaggt   1620
gtacgagagg ctagagaagc tgcaggcagt ggtggcgggg gtgcccgggc atttggaggc   1680
cgccagctgc atcccccctt ccccgcagga gaactcctac gtgtccagca ctggcagagc   1740
ccacagtggg gctgctccat ggcagcccct ggcagcgcca tcaggagcca gtgcccaggc   1800
agcagagcag ctgcagagag gccccaacca gcccgtggag agtgacgaga gcctaggcgg   1860
cctctctgct gccctgcgct cctggcactt gactccaagc tgccctctgg acccagcacc   1920
cctcagggag gccggctgtc ctcaggggga cacggcagga gaatcgagct gggggagtgg   1980
cccaggatcc cggcccacag ccgtggaagg actggccctt ggcagctctg catcatcgtc   2040
gtcagagcca ccgcagatta tcatcaaccc tgcccgacag aagatggtcc agaagctggc   2100
cctgtacgag gatggggccc tggacagcct gcagctgctg tcgtccagct ccctcccagg   2160
cttgggcctg gaacaggaca ggcaggggcc cgaagaaagt gatgaatttc agagctgatg   2220
tgttcacctg ggcagatccc ccaaatccgg aagtcaaagt tctcatggtc agaagttctc   2280
atggtgcacg agtcctcagc actctgccgg cagtgggggt gggggcccat gcccgcgggg   2340
gagagaagga ggtggccctg ctgttctagg ctctgtgggc ataggcaggc agagtggaac   2400
cctgcctcca tgccagcatc tgggggcaag gaaggctggc atcatccagt gaggaggctg   2460
gcgcatgttg ggaggctgct ggctgcacag acccgtgagg ggaggagagg ggctgctgtg   2520
caggggtgtg gagtagggag ctggctcccc tgagagccat gcagggcgtc tgcagcccag   2580
gcctctggca gcagctcttt gcccatctct ttggacagtg gccaccctgc acaatggggc   2640
```

```
cgacgaggcc tagggccctc ctacctgctt acaatttgga aaagtgtggc cgggtgcggt   2700

ggctcacgcc tgtaatccca gcactttggg aggccaaggc aggaggatcg ctggagccca   2760

gtaggtcaag accagccagg gcaacatgat gagaccctgt ctctgccaaa aaattttta    2820

aactattagc ctggcgtggt agcgcacgcc tgtggtccca gctgctgggg aggctgaagt   2880

aggaggatca tttatgcttg ggaggtcgag gctgcagtga gtcatgattg tatgactgca   2940

ctccagcctg ggtgacagag caagaccctg tttcaaaaag aaaaaccctg ggaaaagtga   3000

agtatggctg taagtctcat ggttcagtcc tagcaagaag cgagaattct gagatcctcc   3060

agaaagtcga gcagcaccca cctccaacct cgggccagtg tcttcaggct ttactgggga   3120

cctgcgagct ggcctaatgt ggtggcctgc aagccaggcc atccctgggc gccacagacg   3180

agctccgagc caggtcaggc ttcggaggcc acaagctcag cctcaggccc aggcactgat   3240

tgtggcagag gggccactac ccaaggtcta gctaggccca agacctagtt acccagacag   3300

tgagaagccc ctggaaggca gaaaagttgg gagcatggca gacagggaag ggaaacattt   3360

tcagggaaaa gacatgtatc acatgtcttc agaagcaagt caggtttcat gtaaccgagt   3420

gtcctcttgc gtgtccaaaa gtagcccagg gctgtagcac aggcttcaca gtgattttgt   3480

gttcagccgt gagtcacact acatgccccc gtgaagctgg gcattggtga cgtccaggtt   3540

gtccttgagt aataaaaacg tatgttccct aaaaaaaaaa aaa                     3583
```

<210> SEQ ID NO 66
<211> LENGTH: 3496
<212> TYPE: DNA
<213> ORGANISM: Homo sapiens

<400> SEQUENCE: 66

```
gaattctatg gagtgtaatt ttgtgtatga attatatttt taaaacattg aagagttttc     60

agaaagaagg ctagtagagt tgattactga tactttatgc taagcagtac tttttggta     120

gtacaatatt ttgttaggcg tttctgataa cactagaaag gacaagtttt atcttgtgat    180

aaattgatta atgtttacaa catgactgat aattatagct gaatagtcct taaatgatga    240

acaggttatt tagtttttaa atgcagtgta aaaagtgtgc tgtggaaatt ttatggctaa    300

ctaagtttat ggagaaaata ccttcagttg atcaagaata atagtggtat acaaagttag    360

gaagaaagtc aacatgatgc tgcaggaaat ggaaacaaat acaaatgata tttaacaaag    420

atagagttta cagtttttga actttaagcc aaattcattt gacatcaagc actatagcag    480

gcacaggttc aacaaagctt gtgggtattg acttccccca aaagttgtca gctgaagtaa    540

tttagcccac ttaagtaaat actatgatga taagctgtgt gaacttagct tttaaatagt    600

gtgaccatat gaaggtttta attacttttg tttattggaa taaaatgaga tttttgggt     660

tgtcatgtta aagtgcttat agggaaagaa gcctgcatat aatttttac cttgtggcat     720

aatcagtaat tggtctgtta ttcaggcttc atagcttgta accaaatata aataaaaggc    780

ataatttagg tattctatag ttgcttagaa ttttgttaat ataaatctct gtgaaaaatc    840

aaggagtttt aatattttca gaagtgcatc cacctttcag ggctttaagt tagtattact    900

caagattatg aacaaatagc acttaggtta cctgaaagag ttactacaac cccaaagagt    960

tgtgttctaa gtagtatctt ggaaattcag agagatactc atcctacctg aatataaact   1020

gagataaatc cagtaaagaa agtgtagtaa attctacata agagtctatc attgatttct   1080

tttggtggta aaaatcttag ttcatgtgaa gaaatttcat gtgaatgttt tagctatcaa   1140

acagcactgt cacctactca tgcacaaaac tgcctcccaa agacttttcc caggtccctc   1200
```

```
gtatcaaaac attaagagta taatggaaga tagcacgatc ttgtcagatt ggacaaacag   1260
caacaaacaa aaaatgaagt atgacttttc ctgtgaactc tacagaatgt ctacatattc   1320
aactttcccc gccggggtgc ctgtctcaga aaggagtctt gctcgtgctg gtttttatta   1380
tactggtgtg aatgacaagg tcaaatgctt ctgttgtggc ctgatgctgg ataactggaa   1440
actaggagac agtcctattc aaaagcataa acagctatat cctagctgta gctttattca   1500
gaatctggtt tcagctagtc tgggatccac ctctaagaat acgtctccaa tgagaaacag   1560
ttttgcacat tcattatctc ccaccttgga acatagtagc ttgttcagtg gttcttactc   1620
cagcctttct ccaaaccctc ttaattctag agcagttgaa gacatctctt catcgaggac   1680
taacccctac agttatgcaa tgagtactga agaagccaga tttcttacct accatatgtg   1740
gccattaact tttttgtcac catcagaatt ggcaagagct ggtttttatt atataggacc   1800
tggagatagg gtagcctgct ttgcctgtgg tgggaagctc agtaactggg aaccaaagga   1860
tgatgctatg tcagaacacc ggaggcattt tcccaactgt ccatttttgg aaaattctct   1920
agaaactctg aggtttagca tttcaaatct gagcatgcag acacatgcag ctcgaatgag   1980
aacatttatg tactggccat ctagtgttcc agttcagcct gagcagcttg caagtgctgg   2040
tttttattat gtgggtcgca atgatgatgt caaatgcttt tgttgtgatg gtggcttgag   2100
gtgttgggaa tctggagatg atccatgggt agaacatgcc aagtggtttc caaggtgtga   2160
gttcttgata cgaatgaaag gccaagagtt tgttgatgag attcaaggta gatatcctca   2220
tcttcttgaa cagctgttgt caacttcaga taccactgga gaagaaaatg ctgacccacc   2280
aattattcat tttggacctg gagaaagttc ttcagaagat gctgtcatga tgaatacacc   2340
tgtggttaaa tctgccttgg aaatgggctt taatagagac ctggtgaaac aaacagttca   2400
aagtaaaatc ctgacaactg gagagaacta taaaacagtt aatgatattg tgtcagcact   2460
tctaaatgct gaagatgaaa aaagagagga ggagaaggaa aaacaagctg aagaaatggc   2520
atcagatgat ttgtcattaa ttcggaagaa cagaatggct ctctttcaac aattgacatg   2580
tgtgcttcct atcctggata atcttttaaa ggccaatgta attaataaac aggaacatga   2640
tattattaaa caaaaaacac agataccttt acaagcgaga gaactgattg ataccatttt   2700
ggttaaagga aatgctgcgg ccaacatctt caaaaactgt ctaaaagaaa ttgactctac   2760
attgtataag aacttatttg tggataagaa tatgaagtat attccaacag aagatgtttc   2820
aggtctgtca ctggaagaac aattgaggag gttgcaagaa gaacgaactt gtaaagtgtg   2880
tatggacaaa gaagtttctg ttgtatttat tccttgtggt catctggtag tatgccagga   2940
atgtgcccct tctctaagaa aatgccctat ttgcaggggt ataatcaagg gtactgttcg   3000
tacatttctc tcttaaagaa aaatagtcta tattttaacc tgcataaaaa ggtctttaaa   3060
atattgttga acacttgaag ccatctaaag taaaaaggga attatgagtt tttcaattag   3120
taacattcat gttctagtct gctttggtac taataatctt gtttctgaaa agatggtatc   3180
atatatttaa tcttaatctg tttatttaca agggaagatt tatgtttggt gaactatatt   3240
agtatgtatg tgtacctaag ggagtagtgt cactgcttgt tatgcatcat ttcaggagtt   3300
actggatttg ttgttctttc agaaagcttt gaatactaaa ttatagtgta gaaaagaact   3360
ggaaaccagg aactctggag ttcatcagag ttatggtgcc gaattgtctt tggtgctttt   3420
cacttgtgtt ttaaaataag gatttttctc ttatttctcc ccctagtttg tgagaaacat   3480
ctcaataaag tgcttt                                                   3496
```

<210> SEQ ID NO 67

<211> LENGTH: 2764
<212> TYPE: DNA
<213> ORGANISM: Homo sapiens

<400> SEQUENCE: 67

```
ctctaaagct tagagccaag atggcgggat ccaggcaaag gggtctccgg gccagagttc     60

ggccgctgtt ctgcgccttg ctgctgtcac tcggtcgctt cgtccggggc gacggcgtgg    120

gaggagaccc cgcggtcgcg ttgccacatc gccgtttcga gtacaaatac agcttcaagg    180

ggccgcacct ggtgcagagc gacgggaccg tgcccttctg ggcccacgcg gggaatgcta    240

ttccaagttc agatcaaatt cgagtagcac catctttaaa aagccaaaga ggctcagtgt    300

ggacaaagac aaaagcggcc tttgagaact gggaagttga ggtgacattt cgagtgactg    360

gaagaggtcg aattggagct gatggcctag caatttggta tgcagaaaat caaggcttgg    420

agggccctgt gtttggatca gctgatctgt ggaatggtgt tggaatattt tttgattctt    480

ttgacaatga tggaaagaaa aataatcctg ctatagtaat tataggcaac aatggacaaa    540

tccattatga ccatcaaaat gacggggcta gtcaagcttt ggcaagttgc cagagggact    600

tccgcaacaa accctatcct gtccgagcaa agattaccta ttaccagaac acactgacag    660

taatgatcaa taatggcttt acaccagata aaaatgatta tgaattttgt gccaaagtgg    720

aaaatatgat tatccctgca caagggcatt ttggaatatc tgctgcaact ggaggtcttg    780

cagatgacca tgatgtcctt tcttttctga ctttccagtt gactgaacct ggaaaagagc    840

cgcccacacc agataaagaa atttcggaaa aggaaaaaga aaagtatcag gaggaatttg    900

agcactttca acaagaattg gataaaaaaa aagaggaatt ccagaagggc caccccgacc    960

tccaagggca gcctgcggag gaaatatttg agagtgtagg agatcgagag ctaagacaag   1020

tctttgaagg acagaatcgt attcatcttg aaatcaagca gctgaaccgg cagttagata   1080

tgattcttga tgaacagaga agatatgtct cttccttaac agaggaaatc tctaaaagag   1140

gagcaggaat gcctgggcag catgggcaga ttactcaaca agaactggat actgttgtga   1200

aaactcagca tgagattctg agacaagtaa atgaaatgaa aaattccatg agtgaaaccg   1260

tcagactggt cagtggaatg cagcaccctg gctctgctgg aggcgtctat gagacaacac   1320

agcacttcat tgacatcaaa gagcacctgc acatagtaaa gagggacata gataacttag   1380

tgcagcgaaa tatgccatca aatgaaaagc cgaaatgccc agaactacca ccatttccat   1440

catgtttgtc tacggtccac ttcattatat ttgttgtggt gcaaactgta ttattcattg   1500

gttatatcat gtataggtct cagcaagaag cagctgccaa aaaattcttt tgactaccat   1560

tttcctgtgt acttcatcta tttgtgtaca aaatgatgtc gttttgaggg aatttaagta   1620

tttaaattgc ttcatagtct aaattattaa ttttcttaat aaaataactg tttaaacatt   1680

gatttgcagt taagaataaa ccttaaagca aagacaacca cattttaatt tgttcacagt   1740

atgtaaatct gtctaaattt cagtgaattt ctggtcagta tgatgcagcc tctgagcaga   1800

tattgaccag taagagggta aataaagtgg gggcaacccc tggatatgaa tgttaccccc   1860

taagtctcca atattgcagg tttccctgta taacgtaaac acacttgccc tcatgcctcc   1920

cagaatatga ggtctaatta agaagtccca tcaggtttat tttgtaacca aagtcttttt   1980

tagaggtcag acttcctaat caaaggcctg ggcctgcagt cctttcatct taatgcaact   2040

tcctttgaaa tcaaagaata ttttgtctga gagctttaag gatctggtaa tagacttcaa   2100

aatgttaagt gaaatttttt ttcctctatt tatcaatgat atatttcact tttaaaggaa   2160

attttggagg aaaatatagc tgctttttgc ctaaaaaacc ttgtgggtgg aaatattcct   2220
```

```
ctgagaatgg cttttatagg tattttgcct ggtaatgtat tcattcatga ttgcccatat   2280

tcttgaatgt ttcttcattc caatggggtc aggtcaatat tatgaaaata atttttatat   2340

ttatatttgt aactaagaat ttatttctcc ctttactaca cgatgtaaat tcacgtcaaa   2400

ttcgatgatc tgaggattta aattcacaaa acctgccact acattctggt ttacattagt   2460

tacttcatgc tggctggggt tagtgaccat ttgcatactc ttttaaatca aggaggctgt   2520

agtagaggca gttttaagat tcttgaaggc aaaatttgaa aaacagtgaa tacttctaat   2580

tgtttccttt tagtgccaga actaagacat tgtgaagcac ttgttagtaa acttaacctt   2640

gaaatgtcag actggaagga gtttttatgt ctttgtgcat acttctgggt attacagaaa   2700

cagtctgtaa ataacatttt aagatgcaaa tttaattctg ttcacagctg atttatactg   2760

attt                                                                2764
```

<210> SEQ ID NO 68
<211> LENGTH: 403
<212> TYPE: DNA
<213> ORGANISM: Homo sapiens

<400> SEQUENCE: 68

```
tttcattagt tatcattagt ttattataaa agagaaatat ggaaattatt tacatgacga     60

aagatttcag aacttcagtg gaatgggcag catcatgttg atgccatttc aatagtgact    120

tatttcagtc tacgtacttt ccaagaatgt caccatctct aaataggaaa taatccttgt    180

catctagaac tactttggtg cctccatatt ctgggagaag aactttatct ccaactttca    240

cgctaactgg ttgaatctct ccaccctttc ctttagaacc cgatccaaca gcgactactg    300

ttgcttgcaa tacttttcct tgagattttt ctggaagcat aatgcctcct ttggttacag    360

tttcagcagc actcctttca accaatactc ggtcaaagag tgg                      403
```

<210> SEQ ID NO 69
<211> LENGTH: 656
<212> TYPE: DNA
<213> ORGANISM: Homo sapiens

<400> SEQUENCE: 69

```
acaactcggt ggtggccact gcgcagacca gacttcgctc gtactcgtgc gcctcgcttc     60

gcttttcctc cgcaaccatg tctgacaaac ccgatatggc tgagatcgag aaattcgata    120

agtcgaaact gaagaagaca gagacgcaag agaaaaatcc actgccttcc aaagaaacga    180

ttgaacagga gaagcaagca ggcgaatcgt aatgaggcgt gcgccgccaa tatgcactgt    240

acattccaca agcattgcct tcttatttta cttcttttag ctgtttaact ttgtaagatg    300

caaagaggtt ggatcaagtt taaatgactg tgctgcccct ttcacatcaa agaactactg    360

acaacgaagg ccgcgcctgc ctttcccatc tgtctatcta tctggctggc agggaaggaa    420

agaacttgca tgttggtgaa ggaagaagtg gggtggaaga agtggggtgg gacgacagtg    480

aaatctagag taaaaccaag ctggcccaag gtgtcctgca ggctgtaatg cagtttaatc    540

agagtgccat tttttttttt gttcaaatga ttttaattat tggaatgcac aatttttttta   600

atatgcaaat aaaaagttta aaaacttaaa aaaaaaaaaa aaaaaaaaaa aaaaaa        656
```

<210> SEQ ID NO 70
<211> LENGTH: 361
<212> TYPE: DNA
<213> ORGANISM: Homo sapiens

<400> SEQUENCE: 70

```
ttttttttc aatgttcagt ttcctttaat gacccccatc tccctgaagg gcaggtgcag     60

gcagctaggt gatggcaaga gatgttcact tgaagatctt gccctgattg aaggctttgc   120

cacatgctgg aaggccccct cccaggaaaa gtactctcga accagcgtct gggtctcctc   180

gctgccagga tccagtttcc gccatgtgta tgactcgtag tccacctgcc aatctggact   240

cagcggaaag gcaagctcct ggcctcggaa gacccagact ccagaaatgg agtctgctat   300

tgttggttcc aaaaaggatg acactgggcg aaggcatttc ttcctcagct tgtccagttc   360

g                                                                   361
```

```
<210> SEQ ID NO 71
<211> LENGTH: 455
<212> TYPE: DNA
<213> ORGANISM: Homo sapiens
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t

<400> SEQUENCE: 71

ttttttttga taatttatga ttttattgtc tttcctttgt ccggccttta acatgtttct    60

gtaatttaaa taaaaatcta tttactttct ccattttagc aaatggtttc tttacccaaa   120

taggttgcac tatagtcccc atatggtttt ctactgttcc acaaccacta tttcacaaag   180

attgacaaaa ctttaataaa agttaaattt acaggacatc ttaaggataa cttggggaaa   240

tatgtaggta aaaaaggaat cgagtccaca aattaaggaa tattttgcta atatggccca   300

acaccaattt caggcaaatc caatctactt aactcatata tttaatgtgg ggtaattttt   360

cttaaccaaa atttangggg gggtatggan tggatattat ttatggccct tggacaaggg   420

tggacngtgt ggntttgttg tggactaggg ngggg                              455
```

```
<210> SEQ ID NO 72
<211> LENGTH: 645
<212> TYPE: DNA
<213> ORGANISM: Homo sapiens

<400> SEQUENCE: 72

ctcctgcagc gtctggggtt tccgttgcag tcctcggaac caggacctcg gcgtggccta    60

gcgagttatg gcgacgaagg ccgtgtgcgt gctgaagggc gacggcccag tgcagggcat   120

catcaatttc gagcagaagg aaagtaatgg accagtgaag gtgtggggaa gcattaaagg   180

actgactgaa ggcctgcatg gattccatgt tcatgagttt ggagataata cagcaggctg   240

taccagtgca ggtcctcact ttaatcctct atccagaaaa cacggtgggc caaaggatga   300

agagaggcat gttggagact tgggcaatgt gactgctgac aaagatggtg tggccgatgt   360

gtctattgaa gattctgtga tctcactctc aggagaccat tgcatcattg gccgcacact   420
```

```
ggtggtccat gaaaaagcag atgacttggg caaaggtgga aatgaagaaa gtacaaagac    480

aggaaacgct ggaagtcgtt tggcttgtgg tgtaattggg atcgcccaat aaacattccc    540

ttggatgtag tctgaggccc cttaactcat ctgttatcct gctagctgta gaaatgtatc    600

ctgataaaca ttaaacactg taatcttaaa aaaaaaaaaa aaaaa                    645
```

<210> SEQ ID NO 73
<211> LENGTH: 1684
<212> TYPE: DNA
<213> ORGANISM: Homo sapiens

<400> SEQUENCE: 73

```
gctttcacaa atacagctct gcaacgcgtt tgccctgata ccatgtctct tcgactttcc     60

agtgcatcca ggaggtcctg tcctcgtccc accactggat cactcagact ctatggtggg    120

ggaaccagct ttggtactgg aaattcttgt ggcatttcag ggattggaag tggcttctct    180

agtgccttcg gaggcagctc atcgggagga aacacagggg gaggtaatcc ctgtgctggc    240

ttcactgtga atgagcgggg gctcctttct ggcaatgaga aggtgaccat gcagaacctc    300

aatgaccgcc tggcatccta cctggacagt gtgcatgctc tggaggaggc caacgctgac    360

ctggagcaga agatcaaggg ctggtatgag aaatttgggc ctggctcttg ccgtggtctt    420

gatcatgact atagcagata tttcccaata attgatgacc ttaaaaatca gatcatcgca    480

tccaccacca gcaatgctaa tgctgttctg cagatcgata atgccaggct tacagctgat    540

gatttcagac tcaagtatga aaatgagctg gctcttcacc agagtgtaga ggctgatgtc    600

aatgggttac gaagagtttt ggatgaaata accctgtgca gaacagatct ggagattcag    660

tatgaaaccc tgagtgagga gatgacttac ctcaaaaaga accataaaga ggaaatgcaa    720

gttctgcagt gcgcagctgg aggcaacgtg aacgtggaga tgaacgcagc ccccggggtg    780

gacctcacag ttctgctgaa caacatgcga gctgagtacg aagcccttgc agagcagaac    840

cgcagggacg cggaggcctg gttcaacgag aagagcgcct ccctgcagca gcagatctct    900

gaggatgtcg gagccacaac ctcagcccgg aatgagctga ctgaaatgaa gcgcactctt    960

caaaccctgg aaattgaact tcagtctctc ctagccacga aacactccct ggagtgctcc   1020

ttgacagaga ccgagagcaa ctactgtgcg cagctggcgc agatccaggc tcagatcggg   1080

gccctggagg agcagctgca ccaggtcaga accgagaccg agggccagaa gctggagtat   1140

gagcagctcc tggacatcaa gctccacctg gaaaaagaaa ttgagaccta ctgtctcctt   1200

ataggaggag atgatggagc ctgtaagtct gggggttaca agtctaaaga ttatggatct   1260

ggaaatgtgg gaagtcaagt caaagaccca gccaaagcca tagtggttaa gaaagttctt   1320

gaggaggtag accaacgcag caaaatactt accaccaggc tccactccct ggaagagaaa   1380

tctcaaagca attaatttga gatgcaacag agaacgtatg ccacatagcc cctgcgaaga   1440

aaaggcatta tgtatctgtc cagaaaaatg tgcatgtcta agaaaaatgt ctaacctgtt   1500

gtctttctgt tactttcttt ctgggcaatc aatgacagca tctccccatt catctagaag   1560

aatgccacac acaaatatga ctcatttgat tatcctacag aaatctgttg tcaattcttt   1620

gtattcaata aacctcttct ttagcaagtt aaaaaaaaaa aaaaaaaaaa aaaaaaaaaa   1680

aaaa                                                                1684
```